(12) United States Patent
Froland et al.

(10) Patent No.: US 7,378,494 B2
(45) Date of Patent: May 27, 2008

(54) PITUITARY ADENYLATE CYCLASE ACTIVATING PEPTIDE (PACAP) RECEPTOR (VPAC2) AGONIST PEPTIDE

(75) Inventors: Wayne A. Froland, Alameda, CA (US); Drew N. Kelner, Newbury Park, CA (US); Michael L. Dumas, Richmond, CA (US); Clark Pan, Castro Valley, CA (US); James Whelan, Madison, CT (US); Yu-chang John Wang, Burlingame, CA (US); Wei Wang, Alameda, CA (US)

(73) Assignee: Bayer HealthCare AG, Leverkusen (DE)

( * ) Notice: Subject to any disclaimer, the term of this patent is extended or adjusted under 35 U.S.C. 154(b) by 626 days.

(21) Appl. No.: 10/618,126

(22) Filed: Jul. 11, 2003

(65) Prior Publication Data

US 2004/0058870 A1  Mar. 25, 2004

Related U.S. Application Data

(60) Provisional application No. 60/395,738, filed on Jul. 12, 2002.

(51) Int. Cl.
*C07K 14/705*  (2006.01)

(52) U.S. Cl. .................................................... 530/350
(58) Field of Classification Search ................... None
See application file for complete search history.

(56) References Cited

U.S. PATENT DOCUMENTS 6,972,319 B1 * 12/2005 Pan et al. .................. 530/324

* cited by examiner

*Primary Examiner*—Michael Pak
(74) *Attorney, Agent, or Firm*—Edwards Angell Palmer & Dodge, LLP; Ralph A. Loren, Esq.

(57) ABSTRACT

This invention provides novel peptides that function in vivo as agonists of the VPAC2 receptor. These insulin secretagogue polypeptides are shown to lower blood glucose in vivo more than controls upon glucose challenge. The polypeptides of this invention are also stable in formulation and have long half-lives. The peptides of the present invention provide a new therapy for patients with decreased endogenous insulin secretion, in particular type 2 diabetics. In particular, the invention is a polypeptide selected from a specific group of VPAC2-related polypeptides, or functional equivalents thereof. The invention is also directed to a method of treating a metabolic disease in a mammal comprising administering a therapeutically effective amount of the insulin secretagogue peptides to said mammal. Also disclosed are methods of making the peptides, both recombinant and synthetic.

1 Claim, 18 Drawing Sheets

| SEQ ID NO: | Sequence |
| --- | --- |
| 1 | HSDAVFTDQYTRLRKQVAAKKYLQSIKQKRY |
| 2 | Ac-HTDAVFTDQYTRLRKQVAAKKYLQSIKQKRY |
| 3 | HSDAVFTDQYTRLRKQMAAKKYLQSIKQKRY |
| 4 | HSDAVFTDQYTRLRKQVAAKKYLQSIKQK |
| 5 | HTEAVFTDQYTRLRKQVAAKKYLQSIKQKRY |
| 6 | HSDAVFTDQYTRLRKQLAVKKYLQDIKQGGT |
| 7 | HSDAVFTDQYTRLRKQMAAKKYLQSIKQKR |
| 8 | HSDAVFTDQYTRLRKQLAAKKYLQTIKQKRY |
| 9 | HSDAVFTDQYTRLRKQMAAKKYLQTIKQKRY |
| 10 | HSDAVFTDQYTRLRKQMAAHKYLQSIKQKRY |
| 11 | HSDAVFTDQYTRLRKQMAAKHYLQSIKQKRY |
| 12 | HSDAVFTDQYTRLRKQMAGKKYLQSIKQKR |
| 13 | HSDAVFTDQYTRLRKQMAKKKYLQSIKQKR |
| 14 | HSDAVFTDQYTRLRKQMARKKYLQSIKQKR |
| 15 | HSDAVFTDQYTRLRKQMASKKYLQSIKQKR |
| 16 | HSDAVFTDQYTRLRKQMAAKKYLQSIPQKR |
| 17 | HSDAVFTDQYTRLRKQMAAKKYLQSIQQKR |
| 18 | HSDAVFTDQYTRLRKQMAAKKYLQSIRQKR |
| 19 | HSDAVFTDQYTRLRKQMAAKKYLQSIKQRR |
| 20 | HSDAVFTDQYTRLRKQMAAKKYLQSIKQKA |
| 21 | HSDAVFTDQYTRLRKQMAAKKYLQSIKQKF |
| 22 | HSDAVFTDQYTRLRKQMAAKKYLQSIKQKH |
| 23 | HSDAVFTDQYTRLRKQMAAKKYLQSIKQKI |
| 24 | HSDAVFTDQYTRLRKQMAAKKYLQSIKQKK |
| 25 | HSDAVFTDQYTRLRKQMAAKKYLQSIKQKL |
| 26 | HSDAVFTDQYTRLRKQMAAKKYLQSIKQKM |
| 27 | HSDAVFTDQYTRLRKQMAAKKYLQSIKQKP |
| 28 | HSDAVFTDQYTRLRKQMAAKKYLQSIKQKQ |
| 29 | HSDAVFTDQYTRLRKQMAAKKYLQSIKQKS |
| 30 | HSDAVFTDQYTRLRKQMAAKKYLQSIKQKT |
| 31 | HSDAVFTDQYTRLRKQMAAKKYLQSIKQKV |
| 32 | HSDAVFTDQYTRLRKQMAAKKYLQSIKQKW |
| 33 | HSDAVFTDQYTRLRKQMAAKKYLQSIKQKY |
| 34 | HSDAVFTDQYTRLRKQMAGKKYLQSIKQRI |
| 35 | HSDAVFTDQYTRLRKQMAKKKYLQSIKQRI |
| 36 | HSDAVFTDQYTRLRKQMASKKYLQSIKQRI |
| 37 | HSDAVFTDQYTRLRKQMAAKKYLQSIPQRI |
| 38 | HSDAVFTDQYTRLRKQMASKKYLQSIRQRI |

FIG. 1a

| SEQ ID NO: | Sequenc |
|---|---|
| 39 | HSDAVFTDNYTRLRKQVAAKKYLQSIKQKRY |
| 40 | Ac-HTDAVFTDNYTRLRKQVAAKKYLQSIKQKRY |
| 41 | HSDAVFTDNYTRLRKQMAAKKYLQSIKQKRY |
| 42 | HSDAVFTDNYTRLRKQVAAKKYLQSIKQK |
| 43 | HTEAVFTDNYTRLRKQVAAKKYLQSIKQKRY |
| 44 | HSDAVFTDNYTRLRKQLAVKKYLQDIKQGGT |
| 45 | HSDAVFTDNYTRLRKQMAAKKYLQSIKQKR |
| 46 | HSDAVFTDNYTRLRKQLAAKKYLQTIKQKRY |
| 47 | HSDAVFTDNYTRLRKQMAAKKYLQTIKQKRY |
| 48 | HSDAVFTDNYTRLRKQMAAHKYLQSIKQKRY |
| 49 | HSDAVFTDNYTRLRKQMAAKHYLQSIKQKRY |
| 50 | HSDAVFTDNYTRLRKQMAGKKYLQSIKQKR |
| 51 | HSDAVFTDNYTRLRKQMAKKKYLQSIKQKR |
| 52 | HSDAVFTDNYTRLRKQMARKKYLQSIKQKR |
| 53 | HSDAVFTDNYTRLRKQMASKKYLQSIKQKR |
| 54 | HSDAVFTDNYTRLRKQMAAKKYLQSIPQKR |
| 55 | HSDAVFTDNYTRLRKQMAAKKYLQSIQQKR |
| 56 | HSDAVFTDNYTRLRKQMAAKKYLQSIRQKR |
| 57 | HSDAVFTDNYTRLRKQMAAKKYLQSIKQRR |
| 58 | HSDAVFTDNYTRLRKQMAAKKYLQSIKQKA |
| 59 | HSDAVFTDNYTRLRKQMAAKKYLQSIKQKF |
| 60 | HSDAVFTDNYTRLRKQMAAKKYLQSIKQKH |
| 61 | HSDAVFTDNYTRLRKQMAAKKYLQSIKQKI |
| 62 | HSDAVFTDNYTRLRKQMAAKKYLQSIKQKK |
| 63 | HSDAVFTDNYTRLRKQMAAKKYLQSIKQKL |
| 64 | HSDAVFTDNYTRLRKQMAAKKYLQSIKQKM |
| 65 | HSDAVFTDNYTRLRKQMAAKKYLQSIKQKP |
| 66 | HSDAVFTDNYTRLRKQMAAKKYLQSIKQKQ |
| 67 | HSDAVFTDNYTRLRKQMAAKKYLQSIKQKS |
| 68 | HSDAVFTDNYTRLRKQMAAKKYLQSIKQKT |
| 69 | HSDAVFTDNYTRLRKQMAAKKYLQSIKQKV |
| 70 | HSDAVFTDNYTRLRKQMAAKKYLQSIKQKW |
| 71 | HSDAVFTDNYTRLRKQMAAKKYLQSIKQKY |
| 72 | HSDAVFTDNYTRLRKQMAGKKYLQSIKQRI |
| 73 | HSDAVFTDNYTRLRKQMAKKKYLQSIKQRI |
| 74 | HSDAVFTDNYTRLRKQMASKKYLQSIKQRI |
| 75 | HSDAVFTDNYTRLRKQMAAKKYLQSIPQRI |
| 76 | HSDAVFTDNYTRLRKQMASKKYLQSIRQRI |

FIG. 1b

| SEQ ID NO: | Sequence |
|---|---|
| 77 | HSDAVFTDQYTRLRKQVAAKKYLQSIKNKRY |
| 78 | Ac-HTDAVFTDQYTRLRKQVAAKKYLQSIKNKRY |
| 79 | HSDAVFTDQYTRLRKQMAAKKYLQSIKNKRY |
| 80 | HSDAVFTDQYTRLRKQVAAKKYLQSIKNK |
| 81 | HTEAVFTDQYTRLRKQVAAKKYLQSIKNKRY |
| 82 | HSDAVFTDQYTRLRKQLAVKKYLQDIKNGGT |
| 83 | HSDAVFTDQYTRLRKQMAAKKYLQSIKNKR |
| 84 | HSDAVFTDQYTRLRKQLAAKKYLQTIKNKRY |
| 85 | HSDAVFTDQYTRLRKQMAAKKYLQTIKNKRY |
| 86 | HSDAVFTDQYTRLRKQMAAHKYLQSIKNKRY |
| 87 | HSDAVFTDQYTRLRKQMAAKHYLQSIKNKRY |
| 88 | HSDAVFTDQYTRLRKQMAGKKYLQSIKNKR |
| 89 | HSDAVFTDQYTRLRKQMAKKKYLQSIKNKR |
| 90 | HSDAVFTDQYTRLRKQMARKKYLQSIKNKR |
| 91 | HSDAVFTDQYTRLRKQMASKKYLQSIKNKR |
| 92 | HSDAVFTDQYTRLRKQMAAKKYLQSIPNKR |
| 93 | HSDAVFTDQYTRLRKQMAAKKYLQSIQNKR |
| 94 | HSDAVFTDQYTRLRKQMAAKKYLQSIRNKR |
| 95 | HSDAVFTDQYTRLRKQMAAKKYLQSIKNRR |
| 96 | HSDAVFTDQYTRLRKQMAAKKYLQSIKNKA |
| 97 | HSDAVFTDQYTRLRKQMAAKKYLQSIKNKF |
| 98 | HSDAVFTDQYTRLRKQMAAKKYLQSIKNKH |
| 99 | HSDAVFTDQYTRLRKQMAAKKYLQSIKNKI |
| 100 | HSDAVFTDQYTRLRKQMAAKKYLQSIKNKK |
| 101 | HSDAVFTDQYTRLRKQMAAKKYLQSIKNKL |
| 102 | HSDAVFTDQYTRLRKQMAAKKYLQSIKNKM |
| 103 | HSDAVFTDQYTRLRKQMAAKKYLQSIKNKP |
| 104 | HSDAVFTDQYTRLRKQMAAKKYLQSIKNKQ |
| 105 | HSDAVFTDQYTRLRKQMAAKKYLQSIKNKS |
| 106 | HSDAVFTDQYTRLRKQMAAKKYLQSIKNKT |
| 107 | HSDAVFTDQYTRLRKQMAAKKYLQSIKNKV |
| 108 | HSDAVFTDQYTRLRKQMAAKKYLQSIKNKW |
| 109 | HSDAVFTDQYTRLRKQMAAKKYLQSIKNKY |
| 110 | HSDAVFTDQYTRLRKQMAGKKYLQSIKNRI |
| 111 | HSDAVFTDQYTRLRKQMAKKKYLQSIKNRI |
| 112 | HSDAVFTDQYTRLRKQMASKKYLQSIKNRI |
| 113 | HSDAVFTDQYTRLRKQMAAKKYLQSIPNRI |
| 114 | HSDAVFTDQYTRLRKQMASKKYLQSIRNRI |

FIG. 1c

| SEQ ID NO: | Sequence |
|---|---|
| 115 | HSDAVFTDQYTRLRKQVAAKKYLQSIKQKRYC-PEG |
| 116 | Ac-HTDAVFTDQYTRLRKQVAAKKYLQSIKQKRYC-PEG |
| 117 | HSDAVFTDQYTRLRKQMAAKKYLQSIKQKRYC-PEG |
| 118 | HSDAVFTDQYTRLRKQVAAKKYLQSIKQKC-PEG |
| 119 | HTEAVFTDQYTRLRKQVAAKKYLQSIKQKRYC-PEG |
| 120 | HSDAVFTDQYTRLRKQLAVKKYLQDIKQGGTC-PEG |
| 121 | HSDAVFTDQYTRLRKQMAAKKYLQSIKQKRC-PEG |
| 122 | HSDAVFTDQYTRLRKQLAAKKYLQTIKQKRYC-PEG |
| 123 | HSDAVFTDQYTRLRKQMAAKKYLQTIKQKRYC-PEG |
| 124 | HSDAVFTDQYTRLRKQMAAHKYLQSIKQKRYC-PEG |
| 125 | HSDAVFTDQYTRLRKQMAAKHYLQSIKQKRYC-PEG |
| 126 | HSDAVFTDQYTRLRKQMAGKKYLQSIKQKRC-PEG |
| 127 | HSDAVFTDQYTRLRKQMAKKKYLQSIKQKRC-PEG |
| 128 | HSDAVFTDQYTRLRKQMARKKYLQSIKQKRC-PEG |
| 129 | HSDAVFTDQYTRLRKQMASKKYLQSIKQKRC-PEG |
| 130 | HSDAVFTDQYTRLRKQMAAKKYLQSIPQKRC-PEG |
| 131 | HSDAVFTDQYTRLRKQMAAKKYLQSIQQKRC-PEG |
| 132 | HSDAVFTDQYTRLRKQMAAKKYLQSIRQKRC-PEG |
| 133 | HSDAVFTDQYTRLRKQMAAKKYLQSIKQRRC-PEG |
| 134 | HSDAVFTDQYTRLRKQMAAKKYLQSIKQKAC-PEG |
| 135 | HSDAVFTDQYTRLRKQMAAKKYLQSIKQKFC-PEG |
| 136 | HSDAVFTDQYTRLRKQMAAKKYLQSIKQKHC-PEG |
| 137 | HSDAVFTDQYTRLRKQMAAKKYLQSIKQKIC-PEG |
| 138 | HSDAVFTDQYTRLRKQMAAKKYLQSIKQKKC-PEG |
| 139 | HSDAVFTDQYTRLRKQMAAKKYLQSIKQKLC-PEG |
| 140 | HSDAVFTDQYTRLRKQMAAKKYLQSIKQKMC-PEG |
| 141 | HSDAVFTDQYTRLRKQMAAKKYLQSIKQKPC-PEG |
| 142 | HSDAVFTDQYTRLRKQMAAKKYLQSIKQKQC-PEG |
| 143 | HSDAVFTDQYTRLRKQMAAKKYLQSIKQKSC-PEG |
| 144 | HSDAVFTDQYTRLRKQMAAKKYLQSIKQKTC-PEG |
| 145 | HSDAVFTDQYTRLRKQMAAKKYLQSIKQKVC-PEG |
| 146 | HSDAVFTDQYTRLRKQMAAKKYLQSIKQKWC-PEG |
| 147 | HSDAVFTDQYTRLRKQMAAKKYLQSIKQKYC-PEG |
| 148 | HSDAVFTDQYTRLRKQMAGKKYLQSIKQRIC-PEG |
| 149 | HSDAVFTDQYTRLRKQMAKKKYLQSIKQRIC-PEG |
| 150 | HSDAVFTDQYTRLRKQMASKKYLQSIKQRIC-PEG |
| 151 | HSDAVFTDQYTRLRKQMAAKKYLQSIPQRIC-PEG |
| 152 | HSDAVFTDQYTRLRKQMASKKYLQSIRQRIC-PEG |

FIG. 1d

BamHI      Factor Xa
GGATCC ATC GAA GGT CGT CAC TCC GAC GCT GTT TTC ACC GAC cag TAC
ACG CGT CTG CGT AAA CAG gtt GCT gca AAG AAA TAC CTG cag TCC ATC aag
cag aag cgt tac TAA TGA CTCGAG   (SEQ ID NO: 153)
         stop codons    XhoI

FIG. 2

| SEQ ID NO: | Sequence |
|---|---|
| 154 | CAC TCC GAC GCT GTT TTC ACC GAC CAG TAC ACG CGT CTG CGT AAA CAG GTT GCT GCA AAG AAA TAC CTG CAG TCC ATC AAG CAG AAG CGT TAC |
| 155 | CAC TCC GAC GCT GTT TTC ACC GAC CAG TAC ACG CGT CTG CGT AAA CAG ATG GCT GCA AAG AAA TAC CTG CAG TCC ATC AAG CAG AAG CGT TAC |
| 156 | CAC TCC GAC GCT GTT TTC ACC GAC CAG TAC ACG CGT CTG CGT AAA CAG GTT GCT GCA AAG AAA TAC CTG CAG TCC ATC AAG CAG AAG |
| 157 | CAC ACC GAA GCT GTT TTC ACC GAC CAG TACACG CGT CTG CGT AAA CAG GTT GCT GCA AAG AAA TAC CTG CAG TCC ATC AAG CAG AAG CGT TAC |
| 158 | CAC TCC GAC GCT GTT TTC ACC GAC CAG TAC ACG CGT CTG CGT AAA CAG CTG GCT GTT AAG AAA TAC CTG CAG GAC ATC AAG CAG GGC GGT ACC |
| 159 | CAC TCC GAC GCT GTT TTC ACC GAC CAG TAC ACG CGT CTG CGT AAA CAG ATG GCT GCA AAG AAA TAC CTG CAG TCC ATC AAG CAG AAG CGT |
| 160 | CAC TCC GAC GCT GTT TTC ACC GAC CAG TAC ACG CGT CTG CGT AAA CAG CTG GCT GCA AAG AAA TAC CTG CAG ACC ATC AAG CAG AAG CGT TAC |
| 161 | CAC TCC GAC GCT GTT TTC ACC GAC CAG TAC ACG CGT CTG CGT AAA CAG ATG GCT GCA AAG AAA TAC CTG CAG ACC ATC AAG CAG AAG CGT TAC |
| 162 | CAC TCC GAC GCT GTT TTC ACC GAC CAG TAC ACG CGT CTG CGT AAA CAG ATG GCT GCA CAC AAA TAC CTG CAG TCC ATC AAG CAG AAG CGT TAC |
| 163 | CAC TCC GAC GCT GTT TTC ACC GAC CAG TAC ACG CGT CTG CGT AAA CAG ATG GCT GCA AAG CAC TAC CTG CAG TCC ATC AAG CAG AAG CGT TAC |
| 164 | CAC TCC GAC GCT GTT TTC ACC GAC CAG TAC ACG CGT CTG CGT AAA CAG ATG GCT GGC AAG AAA TAC CTG CAG TCC ATC AAG CAG AAG CGT |
| 165 | CAC TCC GAC GCT GTT TTC ACC GAC CAG TAC ACG CGT CTG CGT AAA CAG ATG GCT AAA AAG AAA TAC CTG CAG TCC ATC AAG CAG AAG CGT |
| 166 | CAC TCC GAC GCT GTT TTC ACC GAC CAG TAC ACG CGT CTG CGT AAA CAG ATG GCT CGT AAG AAA TAC CTG CAG TCC ATC AAG CAG AAG CGT |
| 167 | CAC TCC GAC GCT GTT TTC ACC GAC CAG TAC ACG CGT CTG CGT AAA CAG ATG GCT TCC AAG AAA TAC CTG CAG TCC ATC AAG CAG AAG CGT |

Fig. 3a

| 168 | CAC TCC GAC GCT GTT TTC ACC GAC CAG TAC ACG CGT CTG CGT AAA CAG ATG GCT GCA AAG AAA TAC CTG CAG TCC ATC CCC CAG AAG CGT |
|---|---|
| 169 | CAC TCC GAC GCT GTT TTC ACC GAC CAG TAC ACG CGT CTG CGT AAA CAG ATG GCT GCA AAG AAA TAC CTG CAG TCC ATC CAG CAG AAG CGT |
| 170 | CAC TCC GAC GCT GTT TTC ACC GAC CAG TAC ACG CGT CTG CGT AAA CAG ATG GCT GCA AAG AAA TAC CTG CAG TCC ATC CGT CAG AAG CGT |
| 171 | CAC TCC GAC GCT GTT TTC ACC GAC CAG TAC ACG CGT CTG CGT AAA CAG ATG GCT GCA AAG AAA TAC CTG CAG TCC ATC AAG CAG CGT CGT |
| 172 | CAC TCC GAC GCT GTT TTC ACC GAC CAG TAC ACG CGT CTG CGT AAA CAG ATG GCT GCA AAG AAA TAC CTG CAG TCC ATC AAG CAG AAG GCA |
| 173 | CAC TCC GAC GCT GTT TTC ACC GAC CAG TAC ACG CGT CTG CGT AAA CAG ATG GCT GCA AAG AAA TAC CTG CAG TCC ATC AAG CAG AAG TTC |
| 174 | CAC TCC GAC GCT GTT TTC ACC GAC CAG TAC ACG CGT CTG CGT AAA CAG ATG GCT GCA AAG AAA TAC CTG CAG TCC ATC AAG CAG AAG CAC |
| 175 | CAC TCC GAC GCT GTT TTC ACC GAC CAG TAC ACG CGT CTG CGT AAA CAG ATG GCT GCA AAG AAA TAC CTG CAG TCC ATC AAG CAG AAG ATC |
| 176 | CAC TCC GAC GCT GTT TTC ACC GAC CAG TAC ACG CGT CTG CGT AAA CAG ATG GCT GCA AAG AAA TAC CTG CAG TCC ATC AAG CAG AAG AAG |
| 177 | CAC TCC GAC GCT GTT TTC ACC GAC CAG TAC ACG CGT CTG CGT AAA CAG ATG GCT GCA AAG AAA TAC CTG CAG TCC ATC AAG CAG AAG CTG |
| 178 | CAC TCC GAC GCT GTT TTC ACC GAC CAG TAC ACG CGT CTG CGT AAA CAG ATG GCT GCA AAG AAA TAC CTG CAG TCC ATC AAG CAG AAG ATG |
| 179 | CAC TCC GAC GCT GTT TTC ACC GAC CAG TAC ACG CGT CTG CGT AAA CAG ATG GCT GCA AAG AAA TAC CTG CAG TCC ATC AAG CAG AAG CCC |
| 180 | CAC TCC GAC GCT GTT TTC ACC GAC CAG TAC ACG CGT CTG CGT AAA CAG ATG GCT GCA AAG AAA TAC CTG CAG TCC ATC AAG CAG AAG CAG |
| 181 | CAC TCC GAC GCT GTT TTC ACC GAC CAG TAC ACG CGT CTG CGT AAA CAG ATG GCT GCA AAG AAA TAC CTG CAG TCC ATC AAG CAG AAG TCC |

Fig. 3b

| 182 | CAC TCC GAC GCT GTT TTC ACC GAC CAG TAC ACG CGT CTG CGT AAA CAG ATG GCT GCA AAG AAA TAC CTG CAG TCC ATC AAG CAG AAG ACC |
|---|---|
| 183 | CAC TCC GAC GCT GTT TTC ACC GAC CAG TAC ACG CGT CTG CGT AAA CAG ATG GCT GCA AAG AAA TAC CTG CAG TCC ATC AAG CAG AAG GTT |
| 184 | CAC TCC GAC GCT GTT TTC ACC GAC CAG TAC ACG CGT CTG CGT AAA CAG ATG GCT GCA AAG AAA TAC CTG CAG TCC ATC AAG CAG AAG TGG |
| 185 | CAC TCC GAC GCT GTT TTC ACC GAC CAG TAC ACG CGT CTG CGT AAA CAG ATG GCT GCA AAG AAA TAC CTG CAG TCC ATC AAG CAG AAG TAC |
| 186 | CAC TCC GAC GCT GTT TTC ACC GAC CAG TAC ACG CGT CTG CGT AAA CAG ATG GCT GGT AAG AAA TAC CTG CAG TCC ATC AAG CAG CGT ATC |
| 187 | CAC TCC GAC GCT GTT TTC ACC GAC CAG TAC ACG CGT CTG CGT AAA CAG ATG GCT AAA AAG AAA TAC CTG CAG TCC ATC AAG CAG CGT ATC |
| 188 | CAC TCC GAC GCT GTT TTC ACC GAC CAG TAC ACG CGT CTG CGT AAA CAG ATG GCT TCC AAG AAA TAC CTG CAG TCC ATC AAG CAG CGT ATC |
| 189 | CAC TCC GAC GCT GTT TTC ACC GAC CAG TAC ACG CGT CTG CGT AAA CAG ATG GCT GCA AAG AAA TAC CTG CAG TCC ATC CCC CAG CGT ATC |
| 190 | CAC TCC GAC GCT GTT TTC ACC GAC CAG TAC ACG CGT CTG CGT AAA CAG ATG GCT TCC AAG AAA TAC CTG CAG TCC ATC CGT CAG CGT ATC |
| 191 | CAC TCC GAC GCT GTT TTC ACC GAC AAC TAC ACG CGT CTG CGT AAA CAG GTT GCT GCA AAG AAA TAC CTG CAG TCC ATC AAG CAG AAG CGT TAC |
| 192 | CAC TCC GAC GCT GTT TTC ACC GAC AAC TAC ACG CGT CTG CGT AAA CAG ATG GCT GCA AAG AAA TAC CTG CAG TCC ATC AAG CAG AAG CGT TAC |
| 193 | CAC TCC GAC GCT GTT TTC ACC GAC AAC TAC ACG CGT CTG CGT AAA CAG GTT GCT GCA AAG AAA TAC CTG CAG TCC ATC AAG CAG AAG |
| 194 | CAC ACC GAA GCT GTT TTC ACC GAC AAC TAC ACG CGT CTG CGT AAA CAG GTT GCT GCA AAG AAA TAC CTG CAG TCC ATC AAG CAG AAG CGT TAC |
| 195 | CAC TCC GAC GCT GTT TTC ACC GAC AAC TAC ACG CGT CTG CGT AAA CAG CTG GCT GTT AAG AAA TAC CTG CAG GAC ATC AAG CAG GGC GGT ACC |

Fig. 3c

| 196 | CAC TCC GAC GCT GTT TTC ACC GAC AAC TAC ACG CGT CTG CGT AAA CAG ATG GCT GCA AAG AAA TAC CTG CAG TCC ATC AAG CAG AAG CGT |
|---|---|
| 197 | CAC TCC GAC GCT GTT TTC ACC GAC AAC TAC ACG CGT CTG CGT AAA CAG CTG GCT GCA AAG AAA TAC CTG CAG ACC ATC AAG CAG AAG CGT TAC |
| 198 | CAC TCC GAC GCT GTT TTC ACC GAC AAC TAC ACG CGT CTG CGT AAA CAG ATG GCT GCA AAG AAA TAC CTG CAG ACC ATC AAG CAG AAG CGT TAC |
| 199 | CAC TCC GAC GCT GTT TTC ACC GAC AAC TAC ACG CGT CTG CGT AAA CAG ATG GCT GCA CAC AAA TAC CTG CAG TCC ATC AAG CAG AAG CGT TAC |
| 200 | CAC TCC GAC GCT GTT TTC ACC GAC AAC TAC ACG CGT CTG CGT AAA CAG ATG GCT GCA AAG CAC TAC CTG CAG TCC ATC AAG CAG AAG CGT TAC |
| 201 | CAC TCC GAC GCT GTT TTC ACC GAC AAC TAC ACG CGT CTG CGT AAA CAG ATG GCT GGC AAG AAA TAC CTG CAG TCC ATC AAG CAG AAG CGT |
| 202 | CAC TCC GAC GCT GTT TTC ACC GAC AAC TAC ACG CGT CTG CGT AAA CAG ATG GCT AAA AAG AAA TAC CTG CAG TCC ATC AAG CAG AAG CGT |
| 203 | CAC TCC GAC GCT GTT TTC ACC GAC AAC TAC ACG CGT CTG CGT AAA CAG ATG GCT CGT AAG AAA TAC CTG CAG TCC ATC AAG CAG AAG CGT |
| 204 | CAC TCC GAC GCT GTT TTC ACC GAC AAC TAC ACG CGT CTG CGT AAA CAG ATG GCT TCC AAG AAA TAC CTG CAG TCC ATC AAG CAG AAG CGT |
| 205 | CAC TCC GAC GCT GTT TTC ACC GAC AAC TAC ACG CGT CTG CGT AAA CAG ATG GCT GCA AAG AAA TAC CTG CAG TCC ATC CCC CAG AAG CGT |
| 206 | CAC TCC GAC GCT GTT TTC ACC GAC AAC TAC ACG CGT CTG CGT AAA CAG ATG GCT GCA AAG AAA TAC CTG CAG TCC ATC CAG CAG AAG CGT |
| 207 | CAC TCC GAC GCT GTT TTC ACC GAC AAC TAC ACG CGT CTG CGT AAA CAG ATG GCT GCA AAG AAA TAC CTG CAG TCC ATC CGT CAG AAG CGT |
| 208 | CAC TCC GAC GCT GTT TTC ACC GAC AAC TAC ACG CGT CTG CGT AAA CAG ATG GCT GCA AAG AAA TAC CTG CAG TCC ATC AAG CAG CGT CGT |
| 209 | CAC TCC GAC GCT GTT TTC ACC GAC AAC TAC ACG CGT CTG CGT AAA CAG ATG GCT GCA AAG AAA TAC CTG CAG TCC ATC AAG CAG AAG GCA |

Fig. 3d

| 210 | CAC TCC GAC GCT GTT TTC ACC GAC AAC TAC ACG CGT CTG CGT AAA CAG ATG GCT GCA AAG AAA TAC CTG CAG TCC ATC AAG CAG AAG TTC |
|---|---|
| 211 | CAC TCC GAC GCT GTT TTC ACC GAC AAC TAC ACG CGT CTG CGT AAA CAG ATG GCT GCA AAG AAA TAC CTG CAG TCC ATC AAG CAG AAG CAC |
| 212 | CAC TCC GAC GCT GTT TTC ACC GAC AAC TAC ACG CGT CTG CGT AAA CAG ATG GCT GCA AAG AAA TAC CTG CAG TCC ATC AAG CAG AAG ATC |
| 213 | CAC TCC GAC GCT GTT TTC ACC GAC AAC TAC ACG CGT CTG CGT AAA CAG ATG GCT GCA AAG AAA TAC CTG CAG TCC ATC AAG CAG AAG AAG |
| 214 | CAC TCC GAC GCT GTT TTC ACC GAC AAC TAC ACG CGT CTG CGT AAA CAG ATG GCT GCA AAG AAA TAC CTG CAG TCC ATC AAG CAG AAG CTG |
| 215 | CAC TCC GAC GCT GTT TTC ACC GAC AAC TAC ACG CGT CTG CGT AAA CAG ATG GCT GCA AAG AAA TAC CTG CAG TCC ATC AAG CAG AAG ATG |
| 216 | CAC TCC GAC GCT GTT TTC ACC GAC AAC TAC ACG CGT CTG CGT AAA CAG ATG GCT GCA AAG AAA TAC CTG CAG TCC ATC AAG CAG AAG CCC |
| 217 | CAC TCC GAC GCT GTT TTC ACC GAC AAC TAC ACG CGT CTG CGT AAA CAG ATG GCT GCA AAG AAA TAC CTG CAG TCC ATC AAG CAG AAG CAG |
| 218 | CAC TCC GAC GCT GTT TTC ACC GAC AAC TAC ACG CGT CTG CGT AAA CAG ATG GCT GCA AAG AAA TAC CTG CAG TCC ATC AAG CAG AAG TCC |
| 219 | CAC TCC GAC GCT GTT TTC ACC GAC AAC TAC ACG CGT CTG CGT AAA CAG ATG GCT GCA AAG AAA TAC CTG CAG TCC ATC AAG CAG AAG ACC |
| 220 | CAC TCC GAC GCT GTT TTC ACC GAC AAC TAC ACG CGT CTG CGT AAA CAG ATG GCT GCA AAG AAA TAC CTG CAG TCC ATC AAG CAG AAG GTT |
| 221 | CAC TCC GAC GCT GTT TTC ACC GAC AAC TAC ACG CGT CTG CGT AAA CAG ATG GCT GCA AAG AAA TAC CTG CAG TCC ATC AAG CAG AAG TGG |
| 222 | CAC TCC GAC GCT GTT TTC ACC GAC AAC TAC ACG CGT CTG CGT AAA CAG ATG GCT GCA AAG AAA TAC CTG CAG TCC ATC AAG CAG AAG TAC |
| 223 | CAC TCC GAC GCT GTT TTC ACC GAC AAC TAC ACG CGT CTG CGT AAA CAG ATG GCT GGT AAG AAA TAC CTG CAG TCC ATC AAG CAG CGT ATC |

Fig. 3e

| | |
|---|---|
| 224 | CAC TCC GAC GCT GTT TTC ACC GAC AAC TAC ACG CGT CTG CGT AAA CAG ATG GCT AAA AAG AAA TAC CTG CAG TCC ATC AAG CAG CGT ATC |
| 225 | CAC TCC GAC GCT GTT TTC ACC GAC AAC TAC ACG CGT CTG CGT AAA CAG ATG GCT TCC AAG AAA TAC CTG CAG TCC ATC AAG CAG CGT ATC |
| 226 | CAC TCC GAC GCT GTT TTC ACC GAC AAC TAC ACG CGT CTG CGT AAA CAG ATG GCT GCA AAG AAA TAC CTG CAG TCC ATC CCC CAG CGT ATC |
| 227 | CAC TCC GAC GCT GTT TTC ACC GAC AAC TAC ACG CGT CTG CGT AAA CAG ATG GCT TCC AAG AAA TAC CTG CAG TCC ATC CGT CAG CGT ATC |
| 228 | CAC TCC GAC GCT GTT TTC ACC GAC CAG TAC ACG CGT CTG CGT AAA CAG GTT GCT GCA AAG AAA TAC CTG CAG TCC ATC AAG AAC AAG CGT TAC |
| 229 | CAC TCC GAC GCT GTT TTC ACC GAC CAG TAC ACG CGT CTG CGT AAA CAG ATG GCT GCA AAG AAA TAC CTG CAG TCC ATC AAG AAC AAG CGT TAC |
| 230 | CAC TCC GAC GCT GTT TTC ACC GAC CAG TAC ACG CGT CTG CGT AAA CAG GTT GCT GCA AAG AAA TAC CTG CAG TCC ATC AAG AAC AAG |
| 231 | CAC ACC GAA GCT GTT TTC ACC GAC CAG TAC ACG CGT CTG CGT AAA CAG GTT GCT GCA AAG AAA TAC CTG CAG TCC ATC AAG AAC AAG CGT TAC |
| 232 | CAC TCC GAC GCT GTT TTC ACC GAC CAG TAC ACG CGT CTG CGT AAA CAG CTG GCT GTT AAG AAA TAC CTG CAG GAC ATC AAG AAC GGC GGT ACC |
| 233 | CAC TCC GAC GCT GTT TTC ACC GAC CAG TAC ACG CGT CTG CGT AAA CAG ATG GCT GCA AAG AAA TAC CTG CAG TCC ATC AAG AAC AAG CGT |
| 234 | CAC TCC GAC GCT GTT TTC ACC GAC CAG TAC ACG CGT CTG CGT AAA CAG CTG GCT GCA AAG AAA TAC CTG CAG ACC ATC AAG AAC AAG CGT TAC |
| 235 | CAC TCC GAC GCT GTT TTC ACC GAC CAG TAC ACG CGT CTG CGT AAA CAG ATG GCT GCA AAG AAA TAC CTG CAG ACC ATC AAG AAC AAG CGT TAC |
| 236 | CAC TCC GAC GCT GTT TTC ACC GAC CAG TAC ACG CGT CTG CGT AAA CAG ATG GCT GCA CAC AAA TAC CTG CAG TCC ATC AAG AAC AAG CGT TAC |
| 237 | CAC TCC GAC GCT GTT TTC ACC GAC CAG TAC ACG CGT CTG CGT AAA CAG ATG GCT GCA AAG CAC TAC CTG CAG TCC ATC AAG AAC AAG CGT TAC |

Fig. 3f

| 238 | CAC TCC GAC GCT GTT TTC ACC GAC CAG TAC ACG CGT CTG CGT AAA CAG ATG GCT GGC AAG AAA TAC CTG CAG TCC ATC AAG AAC AAG CGT |
|---|---|
| 239 | CAC TCC GAC GCT GTT TTC ACC GAC CAG TAC ACG CGT CTG CGT AAA CAG ATG GCT AAA AAG AAA TAC CTG CAG TCC ATC AAG AAC AAG CGT |
| 240 | CAC TCC GAC GCT GTT TTC ACC GAC CAG TAC ACG CGT CTG CGT AAA CAG ATG GCT CGT AAG AAA TAC CTG CAG TCC ATC AAG AAC AAG CGT |
| 241 | CAC TCC GAC GCT GTT TTC ACC GAC CAG TAC ACG CGT CTG CGT AAA CAG ATG GCT TCC AAG AAA TAC CTG CAG TCC ATC AAG AAC AAG CGT |
| 242 | CAC TCC GAC GCT GTT TTC ACC GAC CAG TAC ACG CGT CTG CGT AAA CAG ATG GCT GCA AAG AAA TAC CTG CAG TCC ATC CCC AAC AAG CGT |
| 243 | CAC TCC GAC GCT GTT TTC ACC GAC CAG TAC ACG CGT CTG CGT AAA CAG ATG GCT GCA AAG AAA TAC CTG CAG TCC ATC CAG AAC AAG CGT |
| 244 | CAC TCC GAC GCT GTT TTC ACC GAC CAG TAC ACG CGT CTG CGT AAA CAG ATG GCT GCA AAG AAA TAC CTG CAG TCC ATC CGT AAC AAG CGT |
| 245 | CAC TCC GAC GCT GTT TTC ACC GAC CAG TAC ACG CGT CTG CGT AAA CAG ATG GCT GCA AAG AAA TAC CTG CAG TCC ATC AAG AAC CGT CGT |
| 246 | CAC TCC GAC GCT GTT TTC ACC GAC CAG TAC ACG CGT CTG CGT AAA CAG ATG GCT GCA AAG AAA TAC CTG CAG TCC ATC AAG AAC AAG GCA |
| 247 | CAC TCC GAC GCT GTT TTC ACC GAC CAG TAC ACG CGT CTG CGT AAA CAG ATG GCT GCA AAG AAA TAC CTG CAG TCC ATC AAG AAC AAG TTC |
| 248 | CAC TCC GAC GCT GTT TTC ACC GAC CAG TAC ACG CGT CTG CGT AAA CAG ATG GCT GCA AAG AAA TAC CTG CAG TCC ATC AAG AAC AAG CAC |
| 249 | CAC TCC GAC GCT GTT TTC ACC GAC CAG TAC ACG CGT CTG CGT AAA CAG ATG GCT GCA AAG AAA TAC CTG CAG TCC ATC AAG AAC AAG ATC |
| 250 | CAC TCC GAC GCT GTT TTC ACC GAC CAG TAC ACG CGT CTG CGT AAA CAG ATG GCT GCA AAG AAA TAC CTG CAG TCC ATC AAG AAC AAG AAG |
| 251 | CAC TCC GAC GCT GTT TTC ACC GAC CAG TAC ACG CGT CTG CGT AAA CAG ATG GCT GCA AAG AAA TAC CTG CAG TCC ATC AAG AAC AAG CTG |

Fig. 3g

| 252 | CAC TCC GAC GCT GTT TTC ACC GAC CAG TAC ACG CGT CTG CGT AAA CAG ATG GCT GCA AAG AAA TAC CTG CAG TCC ATC AAG AAC AAG ATG |
|---|---|
| 253 | CAC TCC GAC GCT GTT TTC ACC GAC CAG TAC ACG CGT CTG CGT AAA CAG ATG GCT GCA AAG AAA TAC CTG CAG TCC ATC AAG AAC AAG CCC |
| 254 | CAC TCC GAC GCT GTT TTC ACC GAC CAG TAC ACG CGT CTG CGT AAA CAG ATG GCT GCA AAG AAA TAC CTG CAG TCC ATC AAG AAC AAG CAG |
| 255 | CAC TCC GAC GCT GTT TTC ACC GAC CAG TAC ACG CGT CTG CGT AAA CAG ATG GCT GCA AAG AAA TAC CTG CAG TCC ATC AAG AAC AAG TCC |
| 256 | CAC TCC GAC GCT GTT TTC ACC GAC CAG TAC ACG CGT CTG CGT AAA CAG ATG GCT GCA AAG AAA TAC CTG CAG TCC ATC AAG AAC AAG ACC |
| 257 | CAC TCC GAC GCT GTT TTC ACC GAC CAG TAC ACG CGT CTG CGT AAA CAG ATG GCT GCA AAG AAA TAC CTG CAG TCC ATC AAG AAC AAG GTT |
| 258 | CAC TCC GAC GCT GTT TTC ACC GAC CAG TAC ACG CGT CTG CGT AAA CAG ATG GCT GCA AAG AAA TAC CTG CAG TCC ATC AAG AAC AAG TGG |
| 259 | CAC TCC GAC GCT GTT TTC ACC GAC CAG TAC ACG CGT CTG CGT AAA CAG ATG GCT GCA AAG AAA TAC CTG CAG TCC ATC AAG AAC AAG TAC |
| 260 | CAC TCC GAC GCT GTT TTC ACC GAC CAG TAC ACG CGT CTG CGT AAA CAG ATG GCT GGT AAG AAA TAC CTG CAG TCC ATC AAG AAC CGT ATC |
| 261 | CAC TCC GAC GCT GTT TTC ACC GAC CAG TAC ACG CGT CTG CGT AAA CAG ATG GCT AAA AAG AAA TAC CTG CAG TCC ATC AAG AAC CGT ATC |
| 262 | CAC TCC GAC GCT GTT TTC ACC GAC CAG TAC ACG CGT CTG CGT AAA CAG ATG GCT TCC AAG AAA TAC CTG CAG TCC ATC AAG AAC CGT ATC |
| 263 | CAC TCC GAC GCT GTT TTC ACC GAC CAG TAC ACG CGT CTG CGT AAA CAG ATG GCT GCA AAG AAA TAC CTG CAG TCC ATC CCC AAC CGT ATC |
| 264 | CAC TCC GAC GCT GTT TTC ACC GAC CAG TAC ACG CGT CTG CGT AAA CAG ATG GCT TCC AAG AAA TAC CTG CAG TCC ATC CGT AAC CGT ATC |

Fig. 3h

PITUITARY ADENYLATE CYCLASE ACTIVATING PEPTIDE (PACAP) RECEPTOR (VPAC2) AGONIST PEPTIDE

This application claims benefit of U.S. Provisional Application Ser. No. 60/395,738, filed Jul. 12, 2002, the contents of which are incorporated herein by reference in their entirety.

FIELD OF THE INVENTION

This invention relates to newly identified polypeptides and the use of such polypeptides for therapeutic purposes. More particularly, the polypeptides of the present invention are useful in stimulating the release of insulin from pancreatic β-cells in a glucose-dependent manner, thereby providing a treatment option for those individuals afflicted with metabolic disorders such as diabetes or impaired glucose tolerance, a prediabetic state.

BACKGROUND OF THE INVENTION

Diabetes is characterized by impaired glucose metabolism manifesting itself, among other things, by an elevated blood glucose level in the diabetic patient. Underlying defects lead to a classification of diabetes into two major groups: type 1 diabetes, or insulin dependent diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function and alterations in insulin action.

Type 1 diabetic patients are currently treated with insulin, while the majority of type 2 diabetic patients are treated with agents that stimulate β-cell function or with agents that enhance the tissue sensitivity of the patients towards insulin. Over time almost one-half of type 2 diabetic subjects lose their response to these agents and then must be placed on insulin therapy. The drugs presently used to treat type 2 diabetes are described below.

Alpha-glucosidase inhibitors (e.g., Precose®, Voglibose™, and Miglitol®) reduce the excursion of postprandial glucose by delaying the absorption of glucose from the gut. These drugs are safe and provide treatment for mild to moderately affected diabetic subjects. However, gastrointestinal side effects have been reported in the literature.

Insulin sensitizers are drugs that enhance the body's response to insulin. Thiozolidinediones such as Avandia™ (rosiglitazone) and Actos™ activate the peroxisome proliferator-activated receptor (PPAR) gamma subtype and modulate the activity of a set of genes that have not been well described. Rezulin™ (troglitazone), the first drug in this class, was withdrawn because elevated liver enzyme levels and drug induced hepatotoxicity. These hepatic effects do not appear to be a significant problem in patients using Avandia™ and Actos™. Even so, liver enzyme testing is recommended every 2 months in the first year of therapy and periodically thereafter. Avandia™ and Actos™ seem to be associated with fluid retention and edema. Avandia™ is not indicated for use with insulin because of concern about congestive heart failure. Another potential side effect is weight gain.

Insulin secretagogues (e.g., sulfonylureas (SFUs) and other agents that act by the ATP-dependent K+ channel) are another drug type presently used to treat type 2 diabetes. SFUs are standard therapy for type 2 diabetics that have mild to moderate fasting glycemia. The SFUs have limitations that include a potential for inducing hypoglycemia, weight gain, and high primary and secondary failure rates. Ten to 20% of initially treated patients fail to show a significant treatment effect (primary failure). Secondary failure is demonstrated by an additional 20-30% loss of treatment effect after six months on an SFU. Insulin treatment is required in 50% of the SFU responders after 5-7 years of therapy (Scheen, et al., Diabetes Res. Clin. Pract. 6:533-543, 1989).

Glucophage™ (metformin HCl) is a biguanide that lowers blood glucose by decreasing hepatic glucose output and increasing peripheral glucose uptake and utilization. The drug is effective at lowering blood glucose in mildly and moderately affected subjects and does not have the side effects of weight gain or the potential to induce hypoglycemia. However, Glucophage™ has a number of side effects including gastrointestinal disturbances and lactic acidosis. Glucophage™ is contraindicated in diabetics over the age of 70 and in subjects with impairment in renal or liver function. Finally, Glucophage™ has the same primary and secondary failure rates as the SFUs.

Insulin treatment is instituted after diet, exercise, and oral medications have failed to adequately control blood glucose. This treatment has the drawbacks that it is an injectable, that it can produce hypoglycemia, and that it causes weight gain.

Because of the problems with current treatments, new therapies to treat type 2 diabetes are needed. In particular, new treatments to retain normal (glucose-dependent) insulin secretion are needed. Such new drugs should have the following characteristics: dependent on glucose for promoting insulin secretion (i.e., produce insulin secretion only in the presence of elevated blood glucose); low primary and secondary failure rates; and preserve islet cell function. The strategy to develop the new therapy disclosed herein is based on the cyclic adenosine monophosphate (cAMP) signaling mechanism and its effects on insulin secretion.

Cyclic AMP is a major regulator of the insulin secretion process. Elevation of this signaling molecule promotes the closure of the K+ channels following the activation of protein kinase A pathway. Closure of the K+ channels causes cell depolarization and subsequent opening of Ca++ channels, which in turn leads to exocytosis of insulin granules. Little if any effects on insulin secretion occurs in the absence of low glucose concentrations (Weinhaus, et al., Diabetes 47:1426-1435, 1998). Secretagogues like pituitary adenylate cyclase activating peptide ("PACAP") and GLP-1 (glucagon-like peptide 1) use the cAMP system to regulate insulin secretion in a glucose-dependent fashion (Komatsu, et al., Diabetes 46:1928-1938, 1997; Filipsson, et al., Diabetes 50:1959-1969, 2001; Drucker, Endocrinology 142:521-527, 2001). Insulin secretagogues working through the elevation of cAMP such as GLP-1 and PACAP is also able to enhance insulin synthesis in addition to insulin release (Skoglund, et al., Diabetes 49:1156-1164, 2000; Borboni, et al., Endocrinology 140:5530-5537, 1999).

PACAP is a potent stimulator of glucose-dependent insulin secretion from pancreatic β-cells. Three different PACAP receptor types (PAC1, VPAC1, and VPAC2) have been described (Harmar, et al., Pharmacol. Reviews 50:265-270, 1998; Vaudry, et al., Pharmacol. Reviews 52:269-324, 2000). PACAP displays no receptor selectivities, having comparable activities and potencies at all three-receptors. PAC1 is located predominately in the CNS, whereas VPAC1 and VPAC2 are more widely distributed. VPAC1 is located in the CNS as well as in liver, lungs, and intestine. VPAC2 is located in the CNS, pancreas, skeletal muscle, heart, kidney, adipose tissue, testis, and stomach. Recent work argues that VPAC2 is responsible for the insulin secretion from β-cells (Inagaki, et al., Proc. Natl. Acad. Sci. USA 91:2679-2683, 1994; Tsutsumi, et al., Diabetes 51:1453-1460, 2002). This insulinotropic action of PACAP is mediated by the GTP binding protein Gs. Accumulation of intracellular cAMP in turn activates the nonselective cation channels in β-cells increasing [Ca++], and promotes exocytosis of insulin-containing secretory granules.

PACAP is the newest member of the superfamily of metabolic, neuroendocrine, and neurotransmitter peptide hormones that exert their action through the cAMP-mediated signal transduction pathway (Arimura, Regul. Peptides 37:287-303, 1992). The biologically active peptides are released from the biosynthetic precursor in two molecular forms, either as a 38-amino acid peptide (PACAP-38) and/or as a 27-amino acid peptide (PACAP-27) with an amidated carboxyl termini (Arimura, supra).

The highest concentrations of the two forms of the peptide are found in the brain and testis (Arimura, supra). The shorter form of the peptide, PACAP-27, shows 68% structural homology to vasoactive intestinal polypeptide (VIP). However, the distribution of PACAP and VIP in the central nervous system suggests that these structurally related peptides have distinct neurotransmitter functions (Koves, et al., Neuroendocrinology 54:159-169, 1991).

Recent studies have demonstrated diverse biological effects of PACAP-38, from a role in reproduction (McArdle, Endocrinology 135:815-817, 1994) to an ability to stimulate insulin secretion (Yada, et al., J. Biol. Chem. 269:1290-1293, 1994). In addition, PACAP appears to play a role in hormonal regulation of lipid and carbohydrate metabolism (Gray, et al., Mol. Endocrinol. 15:173947, 2001); circadian function (Harmar, et al., Cell 109: 497-508, 2002); and the immune system, growth, energy homeostasis, and male reproductive function (Asnicar, et al., Endrocrinol. 143: 3994-4006, 2002); regulation of appetite (Tachibana, et al., Neurosci. Lett. 339:203-206, 2003); as well as acute and chronic inflammatory diseases, septic shock, and autoimmune diseases (e.g., systemic lupus erythematosus) (Pozo, Trends Mol. Med. 9:211-217, 2003).

Vasoactive intestinal peptide (VIP) is a 28 amino acid peptide that was first isolated from hog upper small intestine (Said and Mutt, Science 169:1217-1218, 1970; U.S. Pat. No. 3,879,371). This peptide belongs to a family of structurally-related, small polypeptides that includes helodermin, secretin, the somatostatins, and glucagon. The biological effects of VIP are mediated by the activation of membrane-bound receptor proteins that are coupled to the intracellular cAMP signaling system. These receptors were originally known as VIP-R1 and VIP-R2, however, they were later found to be the same receptors as VPAC1 and VPAC2. VIP displays comparable activities and potencies at VPAC1 and VPAC2.

To improve the stability of VIP in human lung fluid, Bolin, et al., (Biopolymers 37:57-66, 1995) made a series of VIP variants designed to enhance the helical propensity of this peptide and reduce proteolytic degradation. Substitutions were focused on positions 8, 12, 17, and 25-28, which were implicated to be unimportant for receptor binding. Moreover, the "GGT" sequence was tagged onto the C-terminus of VIP muteins with the hope of more effectively capping the helix. Finally, to further stabilize the helix, several cyclic variants were synthesized (U.S. Pat. No. 5,677,419). Although these efforts were not directed toward receptor selectivity, they yielded two analogs that have greater than 100-fold VPAC2 selectivity (Gourlet, et al., Peptides 18:403-408, 1997; Xia et al., J. Pharmacol. Exp. Ther., 281:629-633, 1997).

GLP-1 is released from the intestinal L-cell after a meal and functions as an incretin hormone (i.e., it potentiates glucose-induced insulin release from the pancreatic β-cell). It is a 37-amino acid peptide that is differentially expressed by the glucagon gene, depending upon tissue type. The clinical data that support the beneficial effect of raising cAMP levels in β-cells have been collected with GLP-1. Infusions of GLP-1 in poorly controlled type 2 diabetics normalized their fasting blood glucose levels (Gutniak, et al., New Eng. J. Med. 326:1316-1322, 1992) and with longer infusions improved the β-cell function to those of normal subjects (Rachman, et al., Diabetes 45:1524-1530, 1996). A recent report has shown that GLP-1 improves the ability of β-cells to respond to glucose in subjects with impaired glucose tolerance (Byrne, et al., Diabetes 47:1259-1265, 1998). All of these effects, however, are short-lived because of the short half-life of the peptide.

Amylin Pharmaceuticals is conducting Phase III trials with Exendin 4™ (AC2993), a 39 amino acid peptide originally identified in Gila Monster. Amylin has reported that clinical studies demonstrated improved glycemic control in type 2 diabetic patients treated with Exendin 4™. However, the incidence of nausea and vomiting was significant.

Applicants disclosed novel polypeptides that function in vivo as agonists of the VPAC2 receptor in WO 01/23420, the specification of which is incorporated herein in its entirety, and in particular, Applicants disclosed a VPAC2 agonist identified as R3P66. The polypeptides described therein, including R3P66, however, are not suitable commercial candidates given stability issues associated with the polypeptides in formulation, as well as issues with the polypeptides' short half-life.

There exists a need for improved peptides that have the glucose-dependent insulin secretagogue activity of PACAP, GLP-1, or Exendin 4™, but with fewer side-effects, and preferably which are stable in formulation and have long plasma half-lives. Furthermore, tighter control of plasma glucose levels may prevent long-term diabetic complications. Thus, new diabetic drugs should provide an improved quality of life for patients.

SUMMARY OF THE INVENTION

This invention provides novel polypeptides that function in vivo as agonists of the VPAC2 receptor (hereafter, VPAC2) and are effective in the treatment of diseases and conditions that can be ameliorated by agents having VPAC2 agonist activity. Preferably, the polypeptides of this invention are selective VPAC2 agonists, having greater potency at VPAC2 than at VPAC1 and PAC1. For example, but not by way of limitation, these polypeptides stimulate insulin synthesis and release from pancreatic β-cells in a glucose-dependent fashion and subsequent plasma glucose reduction. These secretagogue polypeptides are shown to lower blood glucose in vivo more than vehicle control upon glucose challenge. Still more preferably, the polypeptides of this invention are stable in formulation and have long plasma half-lives and long duration of action in vivo when derivatized.

The polypeptides of the present invention provide a new therapy for patients with, for example, metabolic disorders such as those resulting from decreased endogenous insulin secretion, in particular type 2 diabetics, or for patients with impaired glucose tolerance, a prediabetic state that has a mild alteration in insulin secretion. In addition, the polypeptides of the present invention may be useful in the prevention and/or treatment of type 1 diabetes, gestational diabetes, maturity-onset diabetes of the young (MODY), latent autoimmune diabetes adult (LADA), and associated diabetic dyslipidemia and other diabetic complications, as well as hyperglycemia, hyperinsulinemia, impaired glucose tolerance, impaired fasting glucose, dyslipidemia, hypertriglyceridemia, Syndrome X, and insulin resistance.

The polypeptides of the present invention may also be utilized in the prevention and/or treatment of obesity (e.g., regulation of appetite and food intake), atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease; and for the prevention and/or treatment of lupus, polycystic ovary syndrome, carcinogenesis, and hyperplasia, asthma, male reproduction problems, ulcers, sleep disorders, disorders of lipid and carbohydrate metabolism, circadian dysfunction, growth disorders, disorders of energy homeostasis, immune diseases including autoimmune diseases (e.g., systemic lupus erythematosus), as well as acute and chronic inflammatory diseases, septic shock, and other conditions identified herein, or function otherwise as described later herein.

In particular, one aspect of the invention is a polypeptide selected from the group consisting of SEQ ID NOs: 1 through 152, and fragments, derivatives, and variants thereof that demonstrate at least one biological function that is substantially the same as the polypeptides of the listed SEQ ID NOs. (collectively, "polypeptides of this invention"), including functional equivalents thereof. A preferred embodiment of this invention is a polypeptide selected from the group consisting of SEQ ID NOs: 1 through 38 and SEQ ID NOs: 115 through 152, and fragments, derivatives, and variants thereof that demonstrate at least one biological function that is substantially the same as the polypeptides of the listed SEQ ID NOs. A more preferred embodiment of this invention is a polypeptide selected from the group consisting of SEQ ID NOs: 1 through 5 and SEQ ID NOs: 115 through 119, and fragments, derivatives and variants thereof that demonstrate at least one biological function that is substantially the same as the polypeptides of the listed SEQ ID NOs. A most preferred embodiment of this invention is a polypeptide selected from the group consisting of SEQ ID NOs: 1, 2, 115, and 116, and fragments, derivatives and variants thereof that demonstrate at least one biological function that is substantially the same as the polypeptides of the listed SEQ ID NOs.

Another embodiment of the invention is a polypeptide that encodes the polypeptides of the present invention, and the attendant vectors and host cells necessary to recombinantly express the polypeptides of this invention. These polynucleotide sequences include SEQ ID NOs: 154-264.

Antibodies and antibody fragments that selectively bind the polypeptides of this invention are also provided. Such antibodies are useful in detecting the polypeptides of this invention, and can be identified and made by procedures well known in the art. A polyclonal N-terminal IgG antibody and a monoclonal C-terminal Fab antibody have been generated which recognize polypeptides of this invention.

The invention is also directed to a method of treating diabetes, diabetes-related disorders, and/or other diseases or conditions affected by the polypeptides of this invention, preferably effected by the VPAC2 agonist function of the polypeptides of this invention, in a mammal, comprising administering a therapeutically effective amount of any of the polypeptides of the present invention or any polypeptide active at VPAC2 such as SEQ ID NOs: 1 through 152 to said mammal.

Also disclosed are methods of making the polypeptides of this invention, both recombinant and synthetic.

BRIEF DESCRIPTION OF THE DRAWING

FIGS. 1a-1d depict amino acid sequences of polypeptides of SEQ ID NOs: 1 through 152. SEQ ID NOs: 115-152 refer to peptides that are PEGylated at the C-terminal cysteine via a maleimide linkage. The PEG may be a 22 kD linear PEG or a 43 kD branched PEG.

FIG. 2 depicts a DNA sequence (SEQ ID NO: 153) cloned into pGEX-6P-1 to produced the amino acid sequence of SEQ ID NO: 1. The underlined restriction enzyme sites BamHI and Xho I allow in-frame cloning into the pGEX-6P-1 expression vector. The 12 mer DNA sequence that encodes the Factor Xa recognition site and the 2 stop codons are highlighted in bold. The middle non-highlighted sequence encodes SEQ ID NO: 1 (amino acid sequence). Mutated codons from VIP are depicted by small cap nucleotides.

FIGS. 3a-3h depict the nucleic acid sequences SEQ ID NOs: 154 through 264. These nucleic acid sequences encode the polypeptides of the present invention.

DETAILED DESCRIPTION OF THE INVENTION

Figure 4:
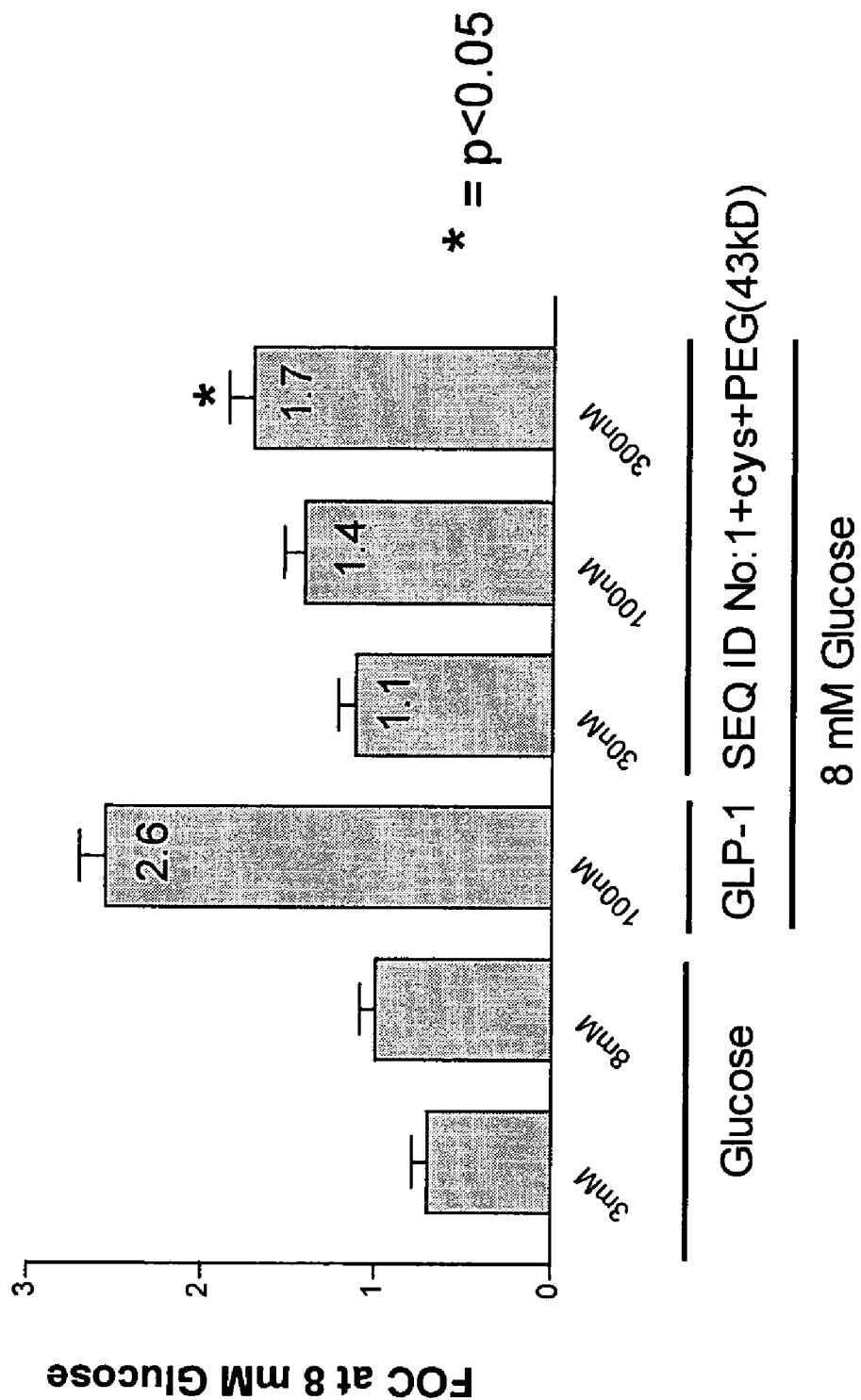
FIG. 4 is a bar chart illustrating insulin secretion of dispersed rat islet cells following exposure to a PEGylated peptide of the present invention.

This invention provides novel polypeptides, and fragments, derivatives, and variants thereof that demonstrate at least one biological function that is substantially the same as the polypeptides of FIGS. 1a-1d (collectively, polypeptides of this invention). The polypeptides of this invention function in vivo as VPAC2 agonists or otherwise in the prevention and/or treatment of such diseases or conditions as diabetes including both type 1 and type 2 diabetes, gestational diabetes, maturity-onset diabetes of the young (MODY) (Herman, et al., Diabetes 43:40, 1994); latent autoimmune diabetes adult (LADA) (Zimmet, et al., Diabetes Med. 11:299, 1994); and associated diabetic dyslipidemia and other diabetic complications, as well as hyperglycemia, hyperinsulinemia, impaired glucose tolerance, impaired fasting glucose, dyslipidemia, hypertriglyceridemia, Syndrome X, and insulin resistance.

In addition, the polypeptides of the present invention may also be utilized in the prevention and/or treatment of obesity (e.g., regulation of appetite and food intake), atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease; and for the prevention and/or treatment of lupus, polycystic ovary syndrome, carcinogenesis, and hyperplasia, asthma, male reproduction problems including human sperm motility, ulcers, sleep disorders, and other conditions identified herein, or function otherwise as described later herein.

Preferably, the polypeptides of this invention will stimulate insulin release from pancreatic β-cells in a glucose-dependent fashion. Still more preferably, the polypeptides of this invention are stable in both aqueous and non-aqueous formulations and exhibit a plasma half-life of greater than one hour.

The polypeptides of this invention are VPAC2 agonists. Preferably, they are selective VPAC2 agonists with at least 10-fold selectivity for VPAC2 over VPAC1 and/or PAC1. More preferably, they are selective VPAC2 agonists with at least 100-fold selectivity for VPAC2 over VPAC1 and/or PAC1. Most preferably, they stimulate insulin release into plasma in a glucose-dependent fashion without inducing a stasis or increase in the level of plasma glucose that is counterproductive to the treatment of, for example, type 2 diabetes. Additionally, it is preferable for the polypeptides of this invention to be selective agonists of the VPAC2 receptor, thereby causing, for example, an increase in insulin release into plasma, while being selective against other receptors that are responsible for such disagreeable or dangerous side effects as gastrointestinal water retention, and/or unwanted cardiovascular effects such as increased heart rate.

The polypeptides of this invention are also stable in aqueous and non-aqueous formulations. Preferably, the polypeptides of this invention will exhibit less than 10% degradation at 37-40° C. over a period of one week, when dissolved in water (at pH between 7-8) or non-aqueous organic solvent. Still more preferable, the polypeptides of this invention will exhibit less than 5% degradation at 37-40° C. over a period of one week, when dissolved in water (at pH between 7-8) or non-aqueous organic solvent. Furthermore, compositions and formulations of the present invention may comprise polypeptides of the present invention and about 2% to about 30% DMSO. In another embodiment of the present invention, the compositions and formulations may optionally include about 0.2% to about 3% (w/v) of additional solvents such as propylene glycol, dimethyl formamide, propylene carbonate, polyethylene glycol, and triglycerides.

Finally, it is preferable for derivatized polypeptides of this invention to exhibit a plasma half-life of at least one hour in rats after IV injection, more preferable the plasma half-life will be at least 2 hours, and still more preferable, the plasma half-life will be at least 3 hours.

The polypeptides of this invention provide a new therapy for patients with decreased endogenous insulin secretion or impaired glucose tolerance, in particular, type 2 diabetes. That is, the polypeptides of the present invention are long-acting VPAC2 agonists that may be used to maintain, improve, and restore glucose-stimulated insulin secretion. Furthermore, a selective peptide agonist of the VPAC2 receptor will enhance glucose-dependent insulin secretion in the pancreas without causing the side effects associated with non-selective activation of the other PACAP receptors.

Certain terms used throughout this specification will now be defined, and others will be defined as introduced. The single letter abbreviation for a particular amino acid, its corresponding amino acid, and three letter abbreviation are as follows: A, alanine (ala); C, cysteine (cys); D, aspartic acid (asp); E, glutamic acid (glu); F, phenylalanine (phe); G, glycine (gly); H, histidine (his); I, isoleucine (ile); K, lycine (lys); L, leucine (leu); M, methionine (met); N, asparagine (asn); P, proline (pro); Q, glutamine (gin); R, arginine (arg); S, serine (ser); T, threonine (thr); V, valine (val); W, tryptophan (trp); Y, tyrosine (tyr).

The term "polynucleotide encoding a polypeptide" encompasses a polynucleotide which includes only coding sequence for the polypeptide, as well as a polynucleotide which includes additional coding and/or non-coding sequence. The present invention further relates to polynucleotides which hybridize to the hereinabove-described sequences if there is at least about 70%, preferably at least about 90%, and more preferably at least about 95% identity between the sequences. The present invention particularly relates to polynucleotides encoding polypeptides which hybridize under stringent conditions to the hereinabove-described polynucleotides. As herein used, the term "stringent conditions" means "stringent hybridization conditions." Preferably, hybridization will occur only if there is at least about 90% and preferably about 95% through 97% identity between the sequences. The polynucleotides which hybridize to the hereinabove described polynucleotides in a preferred embodiment encode polypeptides which retain substantially the same biological function or activity as the mature polypeptide encoded by the cDNAs.

"Functional equivalent" and "substantially the same biological function or activity" each means that degree of biological activity that is within about 30% to about 100% or more of that biological activity demonstrated by the polypeptide to which it is being compared when the biological activity of each polypeptide is determined by the same procedure. For example, a polypeptide that is functionally equivalent to a polypeptide of FIG. 1 is one that, when tested in the cyclic AMP (cAMP) scintillation proximity assay of Example 7, demonstrates accumulation of cAMP in CHO cell line expressing the human VPAC2 receptor.

A polypeptide of this invention that is a VPAC2 agonist is one that demonstrates about 30% to about 100% or more of maximal PACAP-27 VPAC2 agonist activity when tested in the protocol of Example 7. The preferred polypeptides of this invention that are selective agonists for VPAC2 over PACAP, VPAC1, and PAC1 receptors are those polypeptides that demonstrate the ratio of VPAC2 agonist activity to VPAC1 activity of about 10:1 or greater, and more preferably, about 100:1 or greater, and/or demonstrate the ratio of VPAC2 agonist activity to PAC1 receptor activity of about 10:1 or greater, and more preferably, about 100:1 or greater when the polypeptide is tested in the protocol of Example 7, using cells that express the appropriate receptors.

"Stringent hybridization conditions" refers to an overnight incubation of the two polynucleotides (or fragments) to be hybridized at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/mL denatured, sheared salmon sperm DNA, followed by washing the filters in 0.1×SSC at about 65° C.

The terms "fragment," "derivative," and "variant," when referring to the polypeptides of FIG. 1, means fragments, derivatives, and variants of the polypeptides which retain substantially the same biological function or activity as such polypeptides, as described further below.

An analog includes a pro-polypeptide which includes within it, the amino acid sequence of the polypeptide of this invention. The active polypeptide of this invention can be cleaved from the additional amino acids that complete the pro-polypeptide molecule by natural, in vivo processes or by procedures well known in the art such as by enzymatic or chemical cleavage. For example, the 28-amino acid native peptide VIP is naturally expressed as a much larger polypeptide which is then processed in vivo to release the 28-amino acid active mature peptide.

A fragment is a portion of the polypeptide which retains substantially similar functional activity, as described in the in vivo models disclosed herein.

A derivative includes all modifications to the polypeptide which substantially preserve the functions disclosed herein and include additional structure and attendant function (e.g., PEGylated polypeptides which have greater half-life), fusion polypeptides which confer targeting specificity or an additional activity such as toxicity to an intended target, as described further below.

The polypeptides of the present invention may be recombinant polypeptides, natural purified polypeptides, or synthetic polypeptides.

The fragment, derivative, or variant of the polypeptides of the present invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (e.g., polyethyleneglycol), or (iv) one in which the additional amino acids are fused to the mature polypeptide, such as a leader or secretory sequence or a sequence which is employed for purification of the mature polypeptide or a propolypeptide sequence, or (v) one in which the polypeptide sequence is fused with a larger polypeptide (e.g., human albumin, an antibody or Fc, for increased duration of effect). Such fragments, derivatives, and variants and analogs are deemed to be within the scope of those skilled in the art from the teachings herein.

Preferably, the derivatives of the present invention will contain conservative amino acid substitutions (defined further below) made at one or more predicted, preferably nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-conservative substitutions would not be made for conserved amino acid residues or for amino acid residues residing within a conserved protein domain, such as residues 19 and 27 where such residues are essential for protein activity such as VPAC2 activity and/or VPAC2 selectivity. Fragments, or biologically active portions include polypeptide fragments suitable for use as a medicament, to generate antibodies, as a research reagent, and the like. Fragments include peptides comprising amino acid sequences sufficiently similar to or derived from the amino acid sequences of a polypeptide of this invention and exhibiting at least one activity of that polypeptide, but which include fewer amino acids than the full-length polypeptides disclosed herein. Typically, biologically active portions comprise a domain or motif with at least one activity of the polypeptide. A biologically active portion of a polypeptide can be a peptide which is, for example, five or more amino acids in length. Such biologically active portions can be prepared synthetically or by recombinant techniques and can be evaluated for one or more of the functional activities of a polypeptide of this invention by means disclosed herein and/or well known in the art.

Moreover, preferred derivatives of the present invention include mature polypeptides that have been fused with another compound, such as a compound to increase the half-life of the polypeptide and/or to reduce potential immunogenicity of the polypeptide (e.g., polyethylene glycol, "PEG"). In the case of PEGylation, the fusion of the polypeptide to PEG can be accomplished by any means known to one skilled in the art. For example, PEGylation can be accomplished by first introducing a cysteine mutation into the polypeptide to provide a linker upon which to attach the PEG, followed by site-specific derivatization with PEG-maleimide. The cysteine can be added to the C-terminus of the peptides, and is the preferred site in this invention. (see, e.g., Tsutsumi, et al., Proc. Natl. Acad. Sci. USA 97(15): 8548-53, 2000; Veronese, Biomaterials 22:405-417, 2001; Goodsoon & Katre, Bio/Technology 8:343-346, 1990). Variants of the polypeptides of this invention include polypeptides having an amino acid sequence sufficiently similar to the amino acid sequence of the SEQ ID NOs of FIG. 1 or a domain thereof. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Preferably, variants will be sufficiently similar to the amino acid sequence of the preferred polypeptides of this invention. Variants include variants of polypeptides encoded by a polynucleotide that hybridizes to a polynucleotide of this invention or a complement thereof under stringent conditions. Such variants generally retain the functional activity of the polypeptides of this invention. Libraries of fragments of the polynucleotides can be used to generate a variegated population of fragments for screening and subsequent selection. For example, a library of fragments can be generated by treating a double-stranded PCR fragment of a polynucleotide with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the polypeptide of this invention.

Variants include polypeptides that differ in amino acid sequence due to mutagenesis. Variants that function as VPAC2 agonists can be identified by screening combinatorial libraries of mutants, for example truncation mutants, of the polypeptides of this invention for VPAC2 agonist activity.

In one embodiment, a variegated library of analogs is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential variant amino acid sequences is expressible as individual polypeptides, or, alternatively, as a set of larger fusion proteins (for example, for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential variant sequences. Methods for synthesizing degenerate oligonucleotides are known in the art (see, e.g., Narang, Tetrahedron 39:3, 1983; Itakura, et al., Annu. Rev. Biochem. 53:323, 1984; Itakura, et al., Science 198:1056, 1984; Ike, et al., Nucleic Acid Res. 11:477, 1983).

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of R-agonist polypeptides. The most widely used techniques, which are amenable to high through-put analysis for screening large gene libraries typically include cloning the gene library into replicable expression vectors, transforming appropriate cells with the resulting library of vectors and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify the desired variants.

The invention also provides chimeric or fusion polypeptides. The targeting sequence is designed to localize the delivery of the polypeptide to the pancreas to minimize potential side effects. The polypeptides of this invention can be composed of amino acids joined to each other by peptide bonds or modified peptide bonds (i.e., peptide isosteres), and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., *Proteins, Structure and Molecular Properties*, 2nd ed., T. E. Creighton, W.H. Freeman and Company, New York (1993); *Posttranslational Covalent Modification of Proteins*, B. C. Johnson, ed., Academic Press, New York, pgs. 1-12 (1983); Seifter, et al., Meth. Enzymol 182:626-646, 1990; Rattan, et al., Ann. N.Y. Acad. Sci. 663:48-62, 1992).

The polypeptides of the present invention include the polypeptides of FIG. 1 (SEQ ID NOs: 1 through 152), as well as those sequences having insubstantial variations in sequence from them. An "insubstantial variation" would include any sequence addition, substitution, or deletion variant that maintains substantially at least one biological function of the polypeptides of this invention, preferably VPAC2 agonist activity, and more preferably selective VPAC2 agonist activity, and most preferably, the insulin secreting activity demonstrated herein. These functional equivalents may preferably include polypeptides which have at least about 90% identity to the polypeptides of FIG. 1, and more preferably at least 95% identity to the polypeptides of FIG. 1, and still more preferably at least 97% identity to the polypeptides of FIG. 1, and also include portions of such polypeptides having substantially the same biological activity. However, any polypeptide having insubstantial variation in amino acid sequence from the polypeptides of FIG. 1 that demonstrates functional equivalency as described further herein is included in the description of the present invention.

As known in the art "similarity" between two polypeptides is determined by comparing the amino acid sequence and its conserved amino acid substitutes of one polypeptide to the sequence of a second polypeptide. Such conservative substitutions include those described above and by Dayhoff (*The Atlas of Protein Sequence and Structure* 5, 1978), and by Argos (EMBO J. 8:779-785, 1989). For example, amino acids belonging to one of the following groups represent conservative changes:

ala, pro, gly, gin, asn, ser, thr;
cys, ser, tyr, thr;
val, ile, leu, met, ala, phe;
lys, arg, his;
phe, tyr, trp, his; and
asp, glu.

The present invention also relates to polynucleotides encoding the polypeptides of this invention, as well as vectors which include these polynucleotides, host cells which are genetically engineered with vectors of the invention, and the production of polypeptides of the invention by recombinant techniques. Host cells may be genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, or selecting transformants. The culture conditions, such as temperature, pH and the like, are those previously used with the host cell selected for expression, and will be apparent to the ordinarily skilled artisan. The polynucleotide of the present invention may be employed for producing a polypeptide by recombinant techniques. Thus, for example, the polynucleotide sequence may be included in any one of a variety of expression vehicles, in particular, vectors or plasmids for expressing a polypeptide. Such vectors include chromosomal, non-chromosomal, and synthetic DNA sequences (e.g., derivatives of SV40); bacterial plasmids; phage DNA; yeast plasmids; vectors derived from combinations of plasmids and phage DNA; viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include, but are not limited to, LTR or SV40 promoter, the E. coli lac or trp, the phage lambda $P_L$ promoter, and other promoters known to control expression of genes in prokaryotic or eukaryotic cells or their viruses. The expression vector may also contain a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli. The vector containing the appropriate DNA sequence as herein above described, as well as an appropriate promoter or control sequence, may be employed to transform an appropriate host to permit the host to express the protein. Representative examples of appropriate hosts, include, but are not limited to, bacterial cells, such as E. coli, Salmonella typhimurium, Streptomyces; fungal cells, such as yeast; insect cells, such as Drosophila S2 and Spodoptera Sf9; animal cells such as CHO, COS, or Bowes melanoma; adenoviruses; plant cells, etc. The selection of an appropriate host is deemed to be within the scope of those skilled in the art from the teachings herein.

The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9, pBS, phagescript, psiX174, pBluescript SK, pBsKS, pNH8a, pNH16a, pNH18a, pNH46a, pTRC99A, pKK223-3, pKK233-3, pDR540, and PRIT5. Eukaryotic: pWLneo, pSV2cat, pOG44, pXT1, pSG, pSVK3, pBPV, pMSG, and PSVL. However, any other plasmid or vector may be used as long as they are replicable and viable in the host. Promoter regions can be selected from any desired gene using CAT(chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$, and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

The present invention also relates to host cells containing the above-described construct. The host cell can be a higher eukaryotic cell such as a mammalian cell or a lower eukaryotic cell such as a yeast cell, or the host cell can be a prokaryotic cell such as a bacterial cell. Introduction of the construct into the host cell can be effected by calcium phosphate transfection, DEAE-Dextran mediated transfection, or electroporation (Davis, et al., Basic Methods in Molecular Biology, 1986). The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually from about 10 to about 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers. Generally, recombinant expression vectors will include origins of replication and selectable markers permitting transformation of the host cell (e.g., the ampicillin resistance gene of E. coli or S. cerevisiae TRP1 gene), and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics (e.g., stabilization or simplified purification of expressed recombinant product).

Useful expression vectors for bacterial use may be constructed by inserting a structural DNA sequence encoding a desired protein together with suitable translation, initiation, and termination signals in operable reading phase with a functional promoter. The vector may comprise one or more phenotypic selectable markers and an origin of replication to ensure maintenance of the vector and to, if desirable, provide amplification within the host. Suitable prokaryotic hosts for transformation include, for example, *E. coli, Bacillus subtilis, Salmonella typhimurium,* and various species within the genera *Pseudomonas, Streptomyces,* and *Staphylococcus,* although others may also be employed as a matter of choice. Useful expression vectors for bacterial use may comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega, Madison, Wis., USA). These pBR322 "backbone" sections may be combined with an appropriate promoter and the structural sequence to be expressed.

After transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents.

Various mammalian cell culture systems may also be employed to express recombinant protein. Examples of mammalian expression systems include the COS-7 lines of monkey kidney fibroblasts described by Gluzman, (Cell 23:175, 1981), and other cell lines capable of expressing a compatible vector, for example, the C127, 3T3, CHO, HeLa, and BHK cell lines. Mammalian expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required non-transcribed genetic elements.

The polypeptides of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography, and lectin chromatography. Protein refolding steps can be used, as necessary, in completing configuration of the mature protein. Finally, high performance liquid chromatography (HPLC) may be employed for final purification steps.

The polypeptides of this invention may be a product of chemical synthetic procedures, or produced by recombinant techniques from a prokaryotic or eukaryotic host (e.g., bacterial, yeast, higher plant, insect, and mammalian cells). Depending upon the host employed in a recombinant production procedure, the polypeptides of this invention may be glycosylated with mammalian or other eukaryotic carbohydrates, or may be non-glycosylated. Polypeptides of this invention may also include an initial methionine amino acid residue. An isolated or purified polypeptide of this invention, or biologically active portion thereof, is substantially free of other cellular material, or culture medium when produced by recombinant techniques, or substantially free of chemical precursors or other chemicals when chemically synthesized. Preferably, an isolated polypeptide of this invention is substantially free of cellular material and has less than about 30% (by dry weight) of non-polypeptide, or contaminating, material. When the polypeptide of this invention or a biologically active portion thereof is recombinantly produced, preferably culture medium represents less than about 30% of the volume of the polypeptide preparation. When this invention is produced by chemical synthesis, preferably the preparations contain less than about 30% by dry weight of chemical precursors or non-invention chemicals.

The polypeptides of this invention may be conveniently isolated as described in the specific examples below. A preparation of purified polypeptide is at least about 70% pure; preferably, the preparations are about 85% through about 99% pure. Purity of the preparations can be assessed by any means known in the art, such as SDS-polyacrylamide gel electrophoresis and Mass Spec/Liquid Chromatography.

Polynucleotide sequences encoding a polypeptide of this invention may be synthesized, in whole or in part, using chemical methods well known in the art (see, e.g., Caruthers, et al., Nucl. Acids Res. Symp. Ser. 215-223, 1980; Horn, et al., Nucl. Acids Res. Symp. Ser. 225-232, 1980). The polynucleotide that encodes the polypeptide may then be cloned into an expression vector to express the polypeptide.

As will be understood by those of skill in the art, it may be advantageous to produce the polypeptide-encoding nucleotide sequences possessing non-naturally occurring codons. For example, codons preferred by a particular prokaryotic or eukaryotic host can be selected to increase the rate of polypeptide expression or to produce an RNA transcript having desirable properties, such as a half-life which is longer than that of a transcript generated from the naturally occurring sequence.

The nucleotide sequences disclosed herein may be engineered using methods generally known in the art to alter the polypeptide-encoding sequences for a variety of reasons, including but not limited to, alterations which modify the closing, processing, and/or expression of the polypeptide or mRNA product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

Also provided are related compounds within the understanding of those with skill in the art, such as chemical mimetics, organomimetics, or peptidomimetics. As used herein, the terms "mimetic," "peptide mimetic," "peptidomimetic," "organomimetic," and "chemical mimetic" are intended to encompass peptide derivatives, peptide analogs, and chemical compounds having an arrangement of atoms in a three-dimensional orientation that is equivalent to that of a peptide of the present invention. It will be understood that the phrase "equivalent to" as used herein is intended to encompass compounds having substitution(s) of certain atoms, or chemical moieties in said peptide, having bond lengths, bond angles, and arrangements in the mimetic compound that produce the same or sufficiently similar arrangement or orientation of said atoms and moieties to have the biological function of the peptides of the invention. In the peptide mimetics of the invention, the three-dimensional arrangement of the chemical constituents is structurally and/or functionally equivalent to the three-dimensional arrangement of the peptide backbone and component amino acid sidechains in the peptide, resulting in such peptido-, organo-, and chemical mimetics of the peptides of the invention having substantial biological activity. These terms are used according to the understanding in the art, as illustrated, for example, by Fauchere, (Adv. Drug Res. 15:29, 1986); Veber & Freidinger, (TINS p. 392, 1985); and Evans, et al., (J. Med. Chem. 30:1229, 1987), incorporated herein by reference.

It is understood that a pharmacophore exists for the biological activity of each peptide of the invention. A pharmacophore is understood in the art as comprising an idealized, three-dimensional definition of the structural requirements for biological activity. Peptido-, organo-, and chemical mimetics may be designed to fit each pharmacophore with current computer modeling software (computer aided drug design). Said mimetics may be produced by structure-function analysis, based on the positional information from the substituent atoms in the peptides of the invention.

Peptides as provided by the invention can be advantageously synthesized by any of the chemical synthesis techniques known in the art, particularly solid-phase synthesis techniques, for example, using commercially-available automated peptide synthesizers. The mimetics of the present invention can be synthesized by solid phase or solution phase methods conventionally used for the synthesis of peptides (see, e.g., Merrifield, J. Amer. Chem. Soc. 85:2149-54, 1963; Carpino, Acc. Chem. Res. 6:191-98, 1973; Birr, Aspects of the Merrifield Peptide Synthesis, Springer-Verlag: Heidelberg, 1978; The Peptides: Analysis, Synthesis, Biology, Vols. 1, 2, 3, and 5, (Gross & Meinhofer, eds.), Academic Press: New York, 1979; Stewart, et al., Solid Phase Peptide Synthesis, 2nd. ed., Pierce Chem. Co.: Rockford, Ill., 1984; Kent, Ann. Rev. Biochem. 57:957-89, 1988; and Gregg, et al., Int. J. Peptide Protein Res. 55:161-214, 1990, which are incorporated herein by reference in their entirety.)

The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods, or the like. Cycles of deprotection, neutralization, and coupling of successive protected amino acid derivatives are used to link the amino acids from the C-terminus according to the amino acid sequence. For some synthetic peptides, an FMOC strategy using an acid-sensitive resin may be used. Preferred solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydryl-amine resin, and 4-(2',4'-dimethoxyphenyl-FMOC-amino-methyl)-phenoxyacetamidonorleucyl-MBHA resin (Rink amide MBHA resin). In addition, acid-sensitive resins also provide C-terminal acids, if desired. A particularly preferred protecting group for alpha amino acids is base-labile 9-fluorenylmethoxy-carbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys(Trit), FMOC-Ser(But), FMOC-Asn(Trit), FMOC-Leu, FMOC-Thr(Trit), FMOC-Val, FMOC-Gly, FMOC-Lys(Boc), FMOC-Gln(Trit), FMOC-Glu(OBut), FMOC-His(Trit), FMOC-Tyr(But), FMOC-Arg(PMC (2,2,5,7,8-pentamethyl-chroman-6-sulfonyl)), FMOC-Arg(BOC)$_2$, FMOC-Pro, and FMOC-Trp(BOC). The amino acid residues may be coupled by using a variety of coupling agents and chemistries known in the art, such as direct coupling with DIC (diisopropyl-carbodiimide), DCC (dicyclohexylcarbodiimide), BOP (benzotriazolyl-N-oxytrisdimethylaminophosphonium hexa-fluorophosphate), PyBOP (benzotriazole-1-yl-oxy-tris-pyrrolidinophosphonium hexafluoro-phosphate), PyBrOP (bromo-tris-pyrrolidinophosphonium hexafluoro-phosphate); via performed symmetrical anhydrides; via active esters such as pentafluorophenyl esters; or via performed HOBt (1-hydroxybenzotriazole) active esters or by using FMOC-amino acid fluoride and chlorides or by using FMOC-amino acid-N-carboxy anhydrides. Activation with HBTU (2-(1H-benzotriazole-1-yl), 1,1,3,3-tetramethyluronium hexafluorophosphate) or HATU (2-(1H-7-aza-benzotriazole-1-yl),1,1,3,3-tetramethyluronium hexafluoro-phosphate) in the presence of HOBt or HOAt (7-azahydroxybenztriazole) is preferred.

The solid phase method may be carried out manually, although automated synthesis on a commercially available peptide synthesizer (e.g., Applied Biosystems 431A or the like; Applied Biosystems, Foster City, Calif.) is preferred. In a typical synthesis, the first (C-terminal) amino acid is loaded on the chlorotrityl resin. Successive deprotection (with 20% piperidine/NMP (N-methylpyrrolidone)) and coupling cycles according to ABI FastMoc protocols (Applied Biosystems) may be used to generate the peptide sequence. Double and triple coupling, with capping by acetic anhydride, may also be used.

The synthetic mimetic peptide may be cleaved from the resin and deprotected by treatment with TFA (trifluoroacetic acid) containing appropriate scavengers. Many such cleavage reagents, such as Reagent K (0.75 g crystalline phenol, 0.25 mL ethanedithiol, 0.5 mL thioanisole, 0.5 mL deionized water, 10 mL TFA) and others, may be used. The peptide is separated from the resin by filtration and isolated by ether precipitation. Further purification may be achieved by conventional methods, such as gel filtration and reverse phase HPLC (high performance liquid chromatography). Synthetic mimetics according to the present invention may be in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization of the appropriate base.

Generally, those skilled in the art will recognize that peptides as described herein may be modified by a variety of chemical techniques to produce peptides having essentially the same activity as the unmodified peptide, and optionally having other desirable properties. For example, carboxylic acid groups of the peptide may be provided in the form of a salt of a pharmaceutically-acceptable cation. Amino groups within the peptide may be in the form of a pharmaceutically-acceptable acid addition salt, such as the HCl, HBr, acetic, benzoic, toluene sulfonic, maleic, tartaric, and other organic salts, or may be converted to an amide. Thiols may be protected with any one of a number of wellrecognized protecting groups, such as acetamide groups. Those skilled in the art will also recognize methods for introducing cyclic structures into the peptides of this invention so that the native binding configuration will be more nearly approximated. For example, a carboxyl terminal or amino terminal cysteine residue may be added to the peptide, so that when oxidized the peptide will contain a disulfide bond, thereby generating a cyclic peptide. Other peptide cyclizing methods include the formation of thioethers and carboxyl- and amino-terminal amides and esters.

Specifically, a variety of techniques are available for constructing peptide derivatives and analogs with the same or similar desired biological activity as the corresponding peptide compound but with more favorable activity than the peptide with respect to solubility, stability, and susceptibility to hydrolysis and proteolysis. Such derivatives and analogs include peptides modified at the N-terminal amino group, the C-terminal carboxyl group, and/or changing one or more of the amido linkages in the peptide to a non-amido linkage. It will be understood that two or more such modifications may be coupled in one peptide mimetic structure (e.g., modification at the C-terminal carboxyl group and inclusion of a —$CH_2$— carbamate linkage between two amino acids in the peptide).

Amino terminus modifications include alkylating, acetylating, adding a carbobenzoyl group, and forming a succinimide group. Specifically, the N-terminal amino group may be reacted to form an amide group of the formula RC(O)NH— where R is alkyl, preferably lower alkyl, and is added by reaction with an acid halide, RC(O)Cl or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide an N-alkyl amide group of the formula RC(O)NR—. Alternatively, the amino terminus may be covalently linked to succinimide group by reaction with succinic anhydride. An approximately equimolar amount or an excess of succinic anhydride (e.g., about 5 equivalents) is used and the terminal amino group is converted to the succinimide by methods well known in the art including the use of an excess (e.g., 10 equivalents) of a tertiary amine such as diisopropylethylamine in a suitable inert solvent (e.g., dichloromethane), as described in Wollenberg, et al., (U.S. Pat. No. 4,612,132), and is incorporated herein by reference in its entirety. It will also be understood that the succinic group may be substituted with, for example, a $C_2$-through $C_6$-alkyl or —SR substituents, which are prepared in a conventional manner to provide for substituted succinimide at the N-terminus of the peptide. Such alkyl substituents may be prepared by reaction of a lower olefin ($C_2$-through $C_6$-alkyl) with maleic anhydride in the manner described by Wollenberg, et al., supra., and —SR substituents may be prepared by reaction of RSH with maleic anhydride where R is as defined above. In another advantageous embodiment, the amino terminus may be derivatized to form a benzyloxycarbonyl-NH— or a substituted benzyloxycarbonyl-NH— group. This derivative may be produced by reaction with approximately an equivalent amount or an excess of benzyloxycarbonyl chloride (CBZ-Cl), or a substituted CBZ-Cl in a suitable inert diluent (e.g., dichloromethane) preferably containing a tertiary amine to scavenge the acid generated during the reaction. In yet another derivative, the N-terminus comprises a sulfonamide group by reaction with an equivalent amount or an excess (e.g., 5 equivalents) of R—$S(O)_2$Cl in a suitable inert diluent (dichloromethane) to convert the terminal amine into a sulfonamide, where R is alkyl and preferably lower alkyl. Preferably, the inert diluent contains excess tertiary amine (e.g., 10 equivalents) such as diisopropylethylamine, to scavenge the acid generated during reaction. Reaction conditions are otherwise conventional (e.g., room temperature for 30 minutes). Carbamate groups may be produced at the amino terminus by reaction with an equivalent amount or an excess (e.g., 5 equivalents) of R—OC(O)Cl or R—OC(O)O$C_6H_4$—p—$NO_2$ in a suitable inert diluent (e.g., dichloromethane) to convert the terminal amine into a carbamate, where R is alkyl, preferably lower alkyl. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes). Urea groups may be formed at the amino terminus by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

In preparing peptide mimetics wherein the C-terminal carboxyl group may be replaced by an ester (e.g., —C(O)OR where R is alkyl and preferably lower alkyl), resins used to prepare the peptide acids may be employed, and the side chain protected peptide may be cleaved with a base and the appropriate alcohol (e.g., methanol). Side chain protecting groups may be removed in the usual fashion by treatment with hydrogen fluoride to obtain the desired ester. In preparing peptide mimetics wherein the C-terminal carboxyl group is replaced by the amide —C(O)$NR_3R_4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)$NH_2$). Alternatively, use of the chloromethylated resin during peptide synthesis coupled with reaction with ammonia to cleave the side chain protected peptide from the support yields the free peptide amide, and reaction with an alkylamine or a dialkylamine yields a side chain protected alkylamide or dialkylamide (i.e., the C-terminus is —C(O)NR$R_1$, where R and $R_1$ are alkyl and preferably lower alkyl). Side chain protection is then removed in the usual fashion by treatment with hydrogen fluoride to give the free amides, alkylamides, or dialkylamides.

In another alternative embodiment, the C-terminal carboxyl group or a C-terminal ester may be induced to cyclize by displacement of the —OH or the ester (—OR) of the carboxyl group or ester, respectively, with the N-terminal amino group to form a cyclic peptide. For example, after synthesis and cleavage to give the peptide acid, the free acid is converted in solution to an activated ester by an appropriate carboxyl group activator such as dicyclohexylcarbodiimide (DCC), for example, in methylene chloride ($CH_2Cl_2$), dimethyl formamide (DMF), or mixtures thereof. The cyclic peptide is then formed by displacement of the activated ester with the N-terminal amine. Cyclization, rather than polymerization, may be enhanced by use of very dilute solutions according to methods well known in the art.

Peptide mimetics as understood in the art and provided by the invention are structurally similar to the peptide of the invention, but have one or more peptide linkages optionally replaced by a linkage selected from the group consisting of: —$CH_2NH$—, —$CH_2S$—, —$CH_2CH_2$—, —CH=CH— (in both cis and trans conformers), —$COCH_2$—, —CH(OH) $CH_2$—, and —$CH_2SO$—, by methods known in the art and further described in the following references: Spatola, Chemistry and Biochemistry of Amino Acids, Peptides, and Proteins, (Weinstein, ed.), Marcel Dekker: New York, p. 267, 1983; Spatola, Peptide Backbone Modifications 1:3, 1983; Morley, Trends Pharm. Sci. pp. 463-468, 1980; Hudson, et al., Int. J. Pept. Prot. Res. 14:177-185, 1979; Spatola, et al., Life Sci. 38:1243-1249, 1986; Hann, J. Chem. Soc. Perkin Trans. 1 307-314, 1982; Almquist, et al., J. Med. Chem. 23:1392-1398, 1980; Jennings-White, et al., Tetrahedron Lett. 23:2533, 1982; Szelke, et al., EP045665A; Holladay, et al., Tetrahedron Lett. 24:4401-4404, 1983; and Hruby, Life Sci. 31:189-199, 1982; each of which is incorporated herein by reference. Such peptide mimetics may have significant advantages over polypeptide embodiments, including, for example, more economical to produce, having greater chemical stability or enhanced pharmacological properties (such as half-life, absorption, potency, efficacy, etc.), reduced antigenicity, and other properties.

Mimetic analogs of the peptides of the invention may also be obtained using the principles of conventional or rational drug design (see, e.g., Andrews, et al., Proc. Alfred Benzon Symp. 28:145-165, 1990; McPherson, Eur. J. Biochem. 189:1-24, 1990; Hol, et al., in Molecular Recognition: Chemical and Biochemical Problems, (Roberts, ed.); Royal Society of Chemistry; pp. 84-93, 1989a; Hol, Arzneim-Forsch. 39:1016-1018, 1989b; Hol, Agnew Chem. Int. Ed. Engl. 25:767-778, 1986; the disclosures of which are herein incorporated by reference).

In accordance with the methods of conventional drug design, the desired mimetic molecules may be obtained by randomly testing molecules whose structures have an attribute in common with the structure of a "native" peptide. The quantitative contribution that results from a change in a particular group of a binding molecule may be determined by measuring the biological activity of the putative mimetic in comparison with the activity of the peptide. In a preferred embodiment of rational drug design, the mimetic is designed to share an attribute of the most stable three-dimensional conformation of the peptide. Thus, for example, the mimetic may be designed to possess chemical groups that are oriented in a way sufficient to cause ionic, hydrophobic, or van der Waals interactions that are similar to those exhibited by the peptides of the invention, as disclosed herein.

The preferred method for performing rational mimetic design employs a computer system capable of forming a representation of the three-dimensional structure of the peptide, such as those exemplified by Hol, 1989a; Hol, 1989b; and Hol, 1986. Molecular structures of the peptido-, organo-, and chemical mimetics of the peptides of the invention may be produced using computer-assisted design programs commercially available in the art. Examples of such programs include SYBYL 6.5®, HQSAR™, and ALCHEMY 2000™ (Tripos); GALAXY™ and AM2000™ (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.) and CHEMBUILDER3D™ (Interactive Simulations, Inc., San Diego, Calif.).

The peptido-, organo-, and chemical mimetics produced using the peptides disclosed herein using, for example, art-recognized molecular modeling programs may be produced using conventional chemical synthetic techniques, most preferably designed to accommodate high throughput screening, including combinatorial chemistry methods. Combinatorial methods useful in the production of the peptido-, organo-, and chemical mimetics of the invention include phage display arrays, solid-phase synthesis, and combinatorial chemistry arrays, as provided, for example, by SIDDCO (Tuscon, Ariz.); Tripos, Inc.; Calbiochem/Novabiochem (San Diego, Calif.); Symyx Technologies, Inc. (Santa Clara, Calif.); Medichem Research, Inc. (Lemont, Ill.); Pharm-Eco Laboratories, Inc. (Bethlehem, Pa.); or N.V. Organon (Oss, Netherlands). Combinatorial chemistry production of the peptido-, organo-, and chemical mimetics of the invention may be produced according to methods known in the art, including, but not limited to, techniques disclosed in Terrett, (Combinatorial Chemistry, Oxford University Press, London, 1998); Gallop, et al., J. Med. Chem. 37:1233-51, 1994; Gordon, et al., J. Med. Chem. 37:1385-1401, 1994; Look, et al., Bioorg. Med. Chem. Lett. 6:707-12, 1996; Ruhland, et al., J. Amer. Chem. Soc. 118: 253-4, 1996; Gordon, et al., Acc. Chem. Res. 29:144-54, 1996; Thompson & Ellman, Chem. Rev. 96:555-600, 1996; Fruchtel & Jung, Angew. Chem. Int. Ed. Engl. 35:17-42, 1996; Pavia, "The Chemical Generation of Molecular Diversity", Network Science Center, www.netsci.org, 1995; Adnan, et al., "Solid Support Combinatorial Chemistry in Lead Discovery and SAR Optimization," Id., 1995; Davies and Briant, "Combinatorial Chemistry Library Design using Pharmacophore Diversity," Id., 1995; Pavia, "Chemically Generated Screening Libraries: Present and Future," Id., 1996; and U.S. Pat. Nos. 5,880,972; 5,463,564; 5,331573; and 5,573,905.

The newly synthesized polypeptides may be substantially purified by preparative high performance liquid chromatography (see, e.g., Creighton, Proteins: Structures And Molecular Principles, WH Freeman and Co., New York, N.Y., 1983). The composition of a synthetic polypeptide of the present invention may be confirmed by amino acid analysis or sequencing by, for example, the Edman degradation procedure (Creighton, supra). Additionally, any portion of the amino acid sequence of the polypeptide may be altered during direct synthesis and/or combined using chemical methods with sequences from other proteins to produce a variant polypeptide or a fusion polypeptide.

A polypeptide of the invention may also be employed in accordance with the present invention by expression of such polypeptide in vivo, which is often referred to as "gene therapy." Thus, for example, cells may be engineered with a polynucleotide (DNA or RNA) encoding for the polypeptide ex vivo, the engineered cells may then be provided to a patient to be treated with the polypeptide. Such methods are well-known in the art. For example, cells may be engineered by procedures known in the art by use of a retroviral particle containing RNA encoding for the polypeptide of the present invention.

Local delivery of the insulin secretagogues using gene therapy may provide the therapeutic agent to the target area (e.g., pancreas). For instance a pancreas-specific promoter was used to create a β-cell pancreatic tumor mouse model (Hanahan, Nature 315(6015):115-22, 1985).

Both in vitro and in vivo gene therapy methodologies are contemplated. Several methods for transferring potentially therapeutic genes to defined cell populations are known (see, e.g., Mulligan, Science 260:926-31, 1993). These methods include, for example:

1) Direct gene transfer (see, e.g., Wolff, et al., Science 247:1465-68, 1990);
2) Liposome-mediated DNA transfer (see, e.g., Caplen, et al., Nature Med. 3:39-46, 1995; Crystal, Nature Med. 1:15-17, 1995; Gao and Huang, Biochem. Biophys. Res. Comm. 179:280-85 1991);
3) Retrovirus-mediated DNA transfer (see, e.g., Kay, et al., Science 262:117-19, 1993; Anderson, Science 256: 808-13, 1992).
4) DNA virus-mediated DNA transfer. Such DNA viruses include, for example, adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors) (see, e.g., Ali, et al., Gene Therapy 1:367-84, 1994; U.S. Pat. Nos. 4,797,368; 5,139,941; incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuitable for infecting non-dividing cells. In addition, retroviruses have the potential for oncogenicity. However, recent developments in the field of lentiviral vectors may circumvent some of these limitations (see, e.g., Naldini, et al., Science 272:263-67, 1996).

Retroviruses from which retroviral plasmid vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

Adenoviruses have the advantage that they have a broad host range, can infect quiescent or terminally differentiated cells, such as neurons or hepatocytes, and appear essentially non-oncogenic (see, e.g., Ali, et al., 1994). Adenoviruses do not appear to integrate into the host genome. Because they exist extrachromosomally, the risk of insertional mutagenesis is greatly reduced. Ali, et al., 1994.

Adeno-associated viruses exhibit similar advantages as adenoviral-based vectors. However, AAVs exhibit site-specific integration on human chromosome 19 (see, e.g., Ali, et al., 1994).

In a preferred embodiment, the DNA encoding the polypeptide insulin secretagogues of this invention is used in gene therapy for disorders such as diabetes and diabetes-related disorders.

According to this embodiment, gene therapy with DNA encoding polypeptide insulin secretagogues or muteins of this invention is provided to a patient in need thereof, concurrent with, or immediately after diagnosis.

The skilled artisan will appreciate that any suitable gene therapy vector containing polypeptide insulin secretagogues, DNA or DNA fragments, derivatives, or variants of polypeptide insulin secretagogues may be used in accordance with this embodiment. The techniques for constructing such a vector are well known in the art (see, e.g., Anderson, Nature 392:25-30, 1998; Verma, et al., Nature 389:239-242, 1998). Introduction of the polypeptide insulin secretagogues DNA-containing vector to the target site may be accomplished using known techniques.

The vector may include one or more promoters. Suitable promoters which may be employed include, but are not limited to, the retroviral LTR, the SV40 promoter; and the human cytomegalovirus (CMV) promoter (Miller, et al., Biotechniques 7(9):980-990, 1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters such as the adenoviral major late promoter; or heterologous promoters such as the cytomegalovirus (CMV) promoter; the respiratory syncytial virus (RSV) promoter; inducible promoters such as the MMT (metallothionein) promoter; heat shock promoters; the albumin promoter; the ApoAI promoter; human globin promoters; viral thymidinekinase promoters such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector may be employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller (Hum. Gene Ther. 1:5-14, 1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

A different approach to gene therapy is "transkaryotic therapy" wherein the patient's cells are treated ex vivo to induce the dormant chromosomal genes to produce the protein of interest after reintroduction to the patient. Transkaryotic therapy assumes the individual has a normal complement of genes necessary for activation. Transkaryotic therapy involves introducing a promoter or other exogenous regulatory sequence capable of activating the nascent genes, into the chromosomal DNA of the patients' cells ex vivo, culturing and selecting for active protein-producing cells, and then reintroducing the activated cells into the patient with the intent that they then become fully established. The "gene activated" cells then manufacture the protein of interest for some significant amount of time, perhaps for as long as the life of the patient (see, e.g., U.S. Pat. Nos. 5,641,670 and 5,733,761 and are hereby incorporated by reference in their entirety).

Also included in this invention are antibodies and antibodyfragments that selectively bind the polypeptides of this invention. Any type of antibody known in the art may be generated using methods well known in the art. For example, an antibody may be generated to bind specifically to an epitope of a polypeptide of this invention. "Antibody" as used herein includes intact immunoglobulin molecules, as well as fragments thereof, such as Fab, F(ab')$_2$, and Fv, which are capable of binding an epitope of a polypeptide of this invention. Typically, at least 6, 8, 10, or 12 contiguous amino acids are required to form an epitope. However, epitopes which involve non-contiguous amino acids may require more amino acids, for example, at least 15, 25, or 50 amino acids.

An antibody which specifically binds to an epitope of a polypeptide of this invention may be used therapeutically, as well as in immunochemical assays, such as Western blots, ELISAs, radioimmunoassays, immunohistochemical assays, immunoprecipitations, or other immunochemical assays known in the art. Various immunoassays may be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a polypeptide of this invention provides a detection signal at least 5-, 10-, or 20-fold higher than a detection signal provided with other proteins when used in an immunochemical assay. Preferably, antibodies which specifically bind to a polypeptide of this invention do not detect other proteins in immunochemical assays and can immunoprecipitate a polypeptide of this invention from solution.

Polypeptides of this invention may be used to immunize a mammal, such as a mouse, rat, rabbit, guinea pig, monkey, or human, to produce polyclonal antibodies. If desired, a polypeptide of this invention may be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g., lysolecithin, pluronic polyols, polyanions, peptides, oil emulsions, keyhole limpet hemocyanin, and dinitrophenol). Among adjuvants used in humans, BCG (bacilli Calmette-Guerin) and Corynebacterium parvum are especially useful.

Monoclonal antibodies which specifically bind to a polypeptide of this invention may be prepared using any technique which provides for the production of antibody molecules by continuous cell lines in culture. These techniques include, but are not limited to, the hybridoma technique, the human B cell hybridoma technique, and the EBV hybridoma technique (Kohler, et al., Nature 256:495-97, 1985; Kozbor, et al., J. Immunol. Methods 81:3142, 1985; Cote, et al., Proc. Natl. Acad. Sci. 80:2026-30, 1983; Cole, et al., Mol. Cell Biol. 62:109-20, 1984).

In addition, techniques developed for the production of "chimeric antibodies," the splicing of mouse antibody genes to human antibody genes to obtain a molecule with appropriate antigen specificity and biological activity, may be used (Morrison, et al., Proc. Natl. Acad. Sci. 81:6851-55, 1984; Neuberger, et al., Nature 312:604-08, 1984; Takeda, et al., Nature 314:452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences may be minimized by replacing residues which differ from those in the human sequences by site directed mutagenesis of individual residues or by grating of entire complementarity determining regions. Alternatively, humanized antibodies may be produced using recombinant methods (see, e.g., GB2188638B). Antibodies which specifically bind to a polypeptide of this invention may contain antigen binding sites which are either partially or fully humanized, as disclosed in U.S. Pat. No. 5,565,332.

Alternatively, techniques described for the production of single chain antibodies may be adapted using methods known in the art to produce single chain antibodies which specifically bind to a polypeptide of this invention. Antibodies with related specificity, but of distinct idiotypic composition, can be generated by chain shuffling from random combinatorial immunoglobin libraries (Burton, Proc. Natl. Acad. Sci. 88:11120-23, 1991).

Single-chain antibodies also may be constructed using a DNA amplification method, such as PCR, using hybridoma cDNA as a template (Thirion, et al., Eur. J. Cancer Prev. 5:507-11, 1996). Single-chain antibodies can be mono- or bispecific, and can be bivalent or tetravalent. Construction of tetravalent, bispecific single-chain antibodies is taught, for example, in Coloma & Morrison (Nat. Biotechnol. 15:159-63, 1997). Construction of bivalent, bispecific single-chain antibodies is taught in Mallender & Voss (J. Biol. Chem. 269:199-206, 1994).

Anucleotide sequence encoding a single-chain antibody may be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar, et al., Int. J. Cancer 61:497-501, 1995; Nicholls, et al., J. Immunol. Meth. 165:81-91, 1993).

Antibodies which specifically bind to a polypeptide of this invention may also be produced by inducing in vivo production in the lymphocyte population or by screening immunoglobulin libraries or panels of highly specific binding reagents as disclosed in the literature (Orlandi, et al., Proc. Natl. Acad. Sci. 86:38333-37, 1989; Winter, et al., Nature 349:293-99, 1991).

Other types of antibodies may be constructed and used therapeutically in methods of the invention. For example, chimeric antibodies may be constructed as disclosed in WO 93/03151. Binding proteins which are derived from immunoglobulins and which are multivalent and multispecific, such as the "diabodies" also can be prepared (see, e.g., WO 94/13804,).

Human antibodies with the ability to bind to the polypeptides of this invention may also be identified from the MorphoSys HuCAL® library as follows. A polypeptide of this invention may be coated on a microtiter plate and incubated with the MorphoSys HuCAL® Fab phage library. Those phage-linked Fabs not binding to the polypeptide of this invention can be washed away from the plate, leaving only phage which tightly bind to the polypeptide of this invention. The bound phage can be eluted, for example, by a change in pH or by elution with *E. coli* and amplified by infection of *E. coli* hosts. This panning process can be repeated once or twice to enrich for a population of antibodies that tightly bind to the polypeptide of this invention. The Fabs from the enriched pool are then expressed, purified, and screened in an ELISA assay.

Antibodies according to the invention may be purified by methods well known in the art. For example, antibodies may be affinity purified by passage over a column to which a polypeptide of this invention is bound. The bound antibodies can then be eluted from the column using a buffer with a high salt concentration.

The polypeptides of the present invention, as a result of the ability to stimulate insulin secretion from pancreatic islet cells in vitro, and by causing a decrease in blood glucose in vivo, may be employed in treatment diabetes, including both type 1 and type 2 diabetes (non-insulin dependent diabetes mellitus). Such treatment may also delay the onset of diabetes and diabetic complications. The polypeptides may be used to prevent subjects with impaired glucose tolerance from proceeding to develop type 2 diabetes. Other diseases and conditions that may be treated or prevented using compounds of the invention in methods of the invention include: Maturity-Onset Diabetes of the Young (MODY) (Herman, et al., Diabetes 43:40, 1994); Latent Autoimmune Diabetes Adult (LADA) (Zimmet, et al., Diabetes Med. 11:299, 1994); impaired glucose tolerance (IGT) (Expert Committee on Classification of Diabetes Mellitus, Diabetes Care 22 (Supp. 1):S5, 1999); impaired fasting glucose (IFG) (Charles, et al., Diabetes 40:796, 1991); gestational diabetes (Metzger, Diabetes, 40:197, 1991); and metabolic syndrome X.

The polypeptides of the present invention may also be effective in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease; and for the treatment of lupus, polycystic ovary syndrome, carcinogenesis, and hyperplasia, asthma, male reproduction problems, ulcers, sleep disorders, disorders of lipid and carbohydrate metabolism, circadian dysfunction, growth disorders, disorders of energy homeostasis, immune diseases including autoimmune diseases (e.g., systemic lupus erythematosus), as well as acute and chronic inflammatory diseases, and septic shock.

The compounds of the present invention may also be useful for treating physiological disorders related to, for example, cell differentiation to produce lipid accumulating cells, regulation of insulin sensitivity and blood glucose levels, which are involved in, for example, abnormal pancreatic β-cell function, insulin secreting tumors and/or autoimmune hypoglycemia due to autoantibodies to insulin, autoantibodies to the insulin receptor, or autoantibodies that are stimulatory to pancreatic β-cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Compounds of the invention may also be used in methods of the invention to treat secondary causes of diabetes (Expert Committee on Classification of Diabetes Mellitus, Diabetes Care 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenytoin, thyroid hormone, β-adrenergic agents, α-interferon and drugs used to treat HIV infection.

In addition, the polypeptides of the invention may be used for treatment of asthma (Bolin, et al., Biopolymer 37:57-66, 1995; U.S. Pat. No. 5,677,419; showing that polypeptide R3P0 is active in relaxing guinea pig tracheal smooth muscle); hypotension induction (VIP induces hypotension, tachycardia, and facial flushing in asthmatic patients (Morice, et al., Peptides 7:279-280, 1986; Morice, et al., Lancet 2:1225-1227, 1983); male reproduction problems (Siow, et al., Arch. Androl. 43(1):67-71, 1999); as an anti-apoptosis/neuroprotective agent (Brenneman, et al., Ann. N. Y. Acad. Sci. 865:207-12, 1998); cardioprotection during ischemic events (Kalfin, et al., J. Pharmacol. Exp. Ther. 1268(2):952-8, 1994; Das, et al., Ann. N. Y. Acad. Sci. 865:297-308, 1998), manipulation of the circadian clock and its associated disorders (Hamar, et al., Cell 109:497-508, 2002; Shen, et al., Proc. Natl. Acad. Sci. 97:11575-80, 2000), and finally as an anti-ulcer agent (Tuncel, et al., Ann. N. Y. Acad. Sci. 865:309-22, 1998).

The polypeptides of the present invention may be used alone or in combination with additional therapies and/or compounds known to those skilled in the art in the treatment of diabetes and related disorders. Alternatively, the methods and compounds described herein may be used, partially or completely, in combination therapy.

The polypeptides of the invention may also be administered in combination with other known therapies for the treatment of diabetes, including PPAR agonists, sulfonylurea drugs, non-sulfonylurea secretagogues, α-glucosidase inhibitors, insulin sensitizers, insulin secretagogues, hepatic glucose output lowering compounds, insulin and anti-obesity drugs. Such therapies may be administered prior to, concurrently with or following administration of the polypeptides of the invention. Insulin includes both long and short acting forms and formulations of insulin. PPAR agonist may include agonists of any of the PPAR subunits or combinations thereof. For example, PPAR agonist may include agonists of PPAR-α, PPAR-γ, PPAR-δ or any combination of two or three of the subunits of PPAR. PPAR agonists include, for example, rosiglitazone and pioglitazone. Sulfonylurea drugs include, for example, glyburide, glimepiride, chlorpropamide, and glipizide. α-glucosidase inhibitors that may be useful in treating diabetes when administered with a polypeptide of the invention include acarbose, miglitol and voglibose. Insulin sensitizers that may be useful in treating diabetes include thiazolidinediones and non-thiazolidinediones. Hepatic glucose output lowering compounds that may be useful in treating diabetes when administered with a polypeptide of the invention include metformin, such as Glucophage and Glucophage XR. Insulin secretagogues that may be useful in treating diabetes when administered with a polypeptide of the invention include sulfonylurea and non-sulfonylurea drugs: GLP-1, GIP, secretin, nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin. In one embodiment of the invention, polypeptides of the invention are used in combination with insulin secretagogues to increase the sensitivity of pancreatic β-cells to the insulin secretagogue.

Polypeptides of the invention may also be used in methods of the invention in combination with anti-obesity drugs. Anti-obesity drugs include β-3 agonists, CB-1 antagonists, appetite suppressants, such as, for example, sibutramine (Meridia), and lipase inhibitors, such as, for example, orlistat (Xenical).

Polypeptides of the invention may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Polypeptides of the invention may also be used in combination with anti-hypertensive drugs, such as, for example, β-blockers and ACE inhibitors.

Such co-therapies may be administered in any combination of two or more drugs (e.g., a compound of the invention in combination with an insulin sensitizer and an anti-obesity drug). Such co-therapies may be administered in the form of pharmaceutical compositions, as described above.

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

Based on well known assays used to determine the efficacy for treatment of conditions identified above in mammals, and by comparison of these results with the results of known medicaments that are used to treat these conditions, the effective dosage of the polypeptides of this invention can readily be determined for treatment of each desired indication. The amount of the active ingredient (e.g., polypeptides) to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.0001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific polypeptide employed, the age of the patient, the diet of the patient, time of administration, route of administration, rate of excretion of the drug, drug combinations, and the like. The desired mode of treatment and number of doses of a polypeptide of the present invention may be ascertained by those skilled in the art using conventional treatment tests.

The polypeptides of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a therapeutically effective amount of a polypeptide. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A therapeutically effective amount of a polypeptide is that amount which produces a result or exerts an influence on the particular condition being treated. The polypeptides described herein may be administered with a pharmaceutically-acceptable carrier using any effective conventional dosage unit forms, including, for example, immediate and timed release preparations, orally, parenterally, topically, or the like.

For oral administration, the polypeptides may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the polypeptides of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The polypeptides of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane4-methanol, ethers such as poly (ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug (e.g., polypeptide) with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC-CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The polypeptides described herein may be administered as the sole pharmaceutical agent or in combination with one or more other pharmaceutical agents where the combination causes no unacceptable adverse effects. For example, the polypeptides of this invention can be combined with known anti-obesity, or with known antidiabetic or other indication agents, and the like, as well as with admixtures and combinations thereof.

The polypeptides described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Polypeptides are known to undergo hydrolysis, deamidation, oxidation, racemization and isomerization in aqueous and non-aqueous environment. Degradation such as hydrolysis, deamidation or oxidation can readily detected by capillary electrophoresis. Enzymatic degradation notwithstanding, polypeptides having a prolonged plasma half-life, or biological resident time, should, at minimum, be stable in aqueous solution. It is essential that polypeptide exhibits less than 10% degradation over a period of one day at body temperature. It is still more preferable that the polypeptide exhibits less than 5% degradation over a period of one day at body temperature. Because of the life time treatment in chronic diabetic patient, much preferably these therapeutic agents are convenient to administer, furthermore infrequently if by parenteral route. Stability (i.e., less than a few percent of degradation) over a period of weeks at body temperature will allow less frequent dosing. Stability in the magnitude of years at refrigeration temperature will allow the manufacturer to present a liquid formulation, thus avoid the inconvenience of reconstitution. Additionally, stability in organic solvent would provide polypeptide be formulated into novel dosage forms such as implant.

Formulations suitable-for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000).

The following examples are presented to illustrate the invention described herein, but should not be construed as limiting the scope of the invention in any way.

Capsule Formulation

| A capsule formula is prepared from: | |
|---|---|
| Polypeptide of this invention | 10 mg |
| Starch | 109 mg |
| Magnesium stearate | 1 mg |

The components are blended, passed through an appropriate mesh sieve, and filled into hard gelatin capsules.

Tablet Formulation

| A tablet is prepared from: | |
|---|---|
| Polypeptide of this invention | 25 mg |
| Cellulose, microcrystaline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A mg/mL solution of the desired compound of this invention is made using sterile, injectable water, and the pH is adjusted if necessary. The solution is diluted for administration with sterile 5% dextrose and is administered as an IV infusion.

Intramuscular Suspension

The following intramuscular suspension is prepared:

| | |
|---|---|
| Polypeptide of this invention | 50 µg/mL |
| Sodium carboxymethylcellulose | 5 mg/mL |
| TWEEN 80 | 4 mg/mL |
| Sodium chloride | 9 mg/mL |
| Benzyl alcohol | 9 mg/mL |

The suspension is administered intramuscularly.

Hard Shell Capsules

A large number of unit capsules are prepared by filling standard two-piece hard galantine capsules each with powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into molten gelatin to form soft gelatin capsules containing the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin, and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

It should be apparent to one of ordinary skill in the art that changes and modifications can be made to this invention without departing from the spirit or scope of the invention as it is set forth herein.

EXAMPLES

In order that this invention may be better understood, the following examples are set forth. These examples are for the purpose of illustration only, and are not to be construed as limiting the scope of the invention in any manner. All publications mentioned herein are incorporated by reference in their entirety.

Example 1

Peptide Synthesis Methodology

The polypeptides of the present invention were designed to improve stability and prolong half-life of these peptides. Specifically, the non-mutated form of these peptides (see, e.g., WO 01/23420, incorporated herein in its entirety) demonstrated N-terminal hydrolysis, deamidation, as well as dimerization and trimerization in aqueous and non-aqueous environments. To improve stability and minimize hydrolysis, deamidation, and dimerization/trimerization, the asparagine residues (positions 9 and 28) were mutated to glutamine residues. In addition, valine at position 17, alanine at position 19, lysine at position 29, arginine at position 30, and tyrosine at position 31 were also mutated. Furthermore, as described below, the polypeptides of the present invention were also PEGylated to prolong half-life.

The following general procedure was followed to synthesize some of the polypeptides of the invention:

Peptide synthesis was carried out by the FMOC/t-Butyl strategy (Pennington & Dunn, Peptide Synthesis Protocols, Volume 35, 1994) under continuous flow conditions using Rapp-Polymere PEG-Polystyrene resins (Rapp-Polymere, Tubingen, Germany). At the completion of synthesis, peptides are cleaved from the resin and de-protected using TFA/DTT/H$_2$O/Triisopropyl silane (88/5/5/2). Peptides were precipitated from the cleavage cocktail using cold diethyl ether. The precipitate was washed three times with the cold ether, and then dissolved in 5% acetic acid prior to lyophilization. Peptides were checked by reversed phase chromatography on a YMC-Pack ODS-AQ column (YMC, Inc., Wilmington, N.C.) on a Waters ALLIANCE® system (Waters Corporation, Milford, Mass.) using water/acetonitrile with 3% TFA as a gradient from 0% to 100% acetonitrile, and by MALDI mass spectrometry on a VOYAGER DE™ MALDI Mass Spectrometer, (Model 5-2386-00, Per-Septive BioSystems, Framingham, Mass.). The peptide sample was added to the Matrix buffer (50/50 dH$_2$O/acetonitrile with 3% TFA) in a 1/1 ratio. Those peptides not meeting the purity criteria of >95% are purified by reversed phase chromatography on a Waters Delta Prep 4000 HPLC System (Waters Corporation, Milford, Mass.).

Example 2

Peptide PEGylation

The half-life of a peptide in vivo may be increased through attachment of a polyethylene glycol (PEG) moiety to the peptide thereby reducing clearance of the peptide by the kidney and decreasing protease degradation of the peptide. The use of a VPAC2 receptor agonist peptide is severely limited by its very short half-life in vivo; however, attachment of a PEG moiety to the peptide (PEGylation) prolonged the half-life of the peptide sufficiently to allow for once/day to once/week treatment.

PEGylation may be performed by any method known to those skilled in the art. However, in this example, PEGylation was performed by introducing a unique cysteine mutation into the peptide followed by PEGylating the cysteine via a stable thioether linkage between the sulfhydryl of the peptide and maleimide group of the methoxy-PEG-maleimide reagent (Nektar (Inhale/Shearwater), San Carlos, Calif.). It is preferable to introduce the unique cysteine at the C-terminus of the peptide to minimize potential reduction of activity by PEGylation.

Specifically, a 2-fold molar excess of mPEG-mal (MW 22 kD and 43 kD) reagent was added to 1 mg of peptide (e.g., SEQ ID NO:1 having a cysteine mutation at the C-terminus of the peptide) and dissolved in reaction buffer at pH 6 (0.1M Na phosphate/0.1M NaCl/0.1M EDTA). After 0.5 hour at room temperature, the reaction was terminated with 2-fold molar excess of DTT to mPEG-mal. The peptide-PEG-mal reaction mixture was applied to a cation exchange column to remove residual PEG reagents followed by gel filtration column to remove residual free peptide. The purity, mass, and number of PEGylated sites were determined by SDS-PAGE and MALDI-TOF mass spectrometry. When a 22 kD PEG was attached to peptides of the present invention, potent VPAC2 receptor activation was retained. Furthermore, VPAC2 versus VPAC1 and PAC1 selectivity of receptor activation was also retained. It is possible that PEGylation with a smaller PEG (e.g., a linear 22 kD PEG) will less likely reduce activity of the peptide, whereas a larger PEG (e.g., a branched 43 kD PEG) will more likely reduce activity. However, the larger PEG will increase plasma half-life further so that once a week injection may be possible (Harris, et al., Clin. Pharmacokinet. 40:539-551, 2001).

Example 3

Peptide Cloning

To express these peptides recombinantly, the DNA sequence encoding a peptide was cloned C-terminal to glutathione S-transferase (GST) with a single Factor Xa recognition site separating the monomeric peptide and GST. The gene encoding the Factor Xa recognition site fused to DNA sequence of the peptide to be produced was synthesized by hybridizing two overlapping single-stranded DNA fragments (70-90 mers) containing a Bam HI or Xho I restriction enzyme site immediately 5' to the DNA sequence of the gene to be cloned, followed by DNA synthesis of the opposite strands via the large fragment of DNA polymerase I (Life Technologies, Inc., Gaithersburg, Md.). The DNA sequence chosen for each gene was based on the reverse translation of the designed amino acid sequence of each peptide. In some cases, the gene encoding the peptide was generated by PCR mutagenesis (Picard, et al., Nucleic Acids Res 22:2587-91, 1994; Sambrook, et al., Molecular Cloning: A Laboratory Manual, 2nd ed., Cold Spring Harbor Laboratory Press, New York, 1989) of a gene already made by the method described above. The double-stranded product was then digested by Bam HI and Xho I and ligated into pGEX-6P-1 (Amersham Pharmacia Biotech, Piscataway, N.J.) which was also digested with Bam HI and Xho I. For example, to express SEQ ID NO: 1 as a fusion with GST, a designed DNA sequence (FIG. 2) was cloned into pGEX-6P-1.

Example 4

Peptide Recombinant Expression and Purification

BL21 cells (Stratagene, La Jolla, Calif.), transformed with the GST-peptide fusion-containing plasmids, were grown at 37° C. until the $OD_{600}$ reached 0.6 to 1.0, and then the cells were incubated with 1 mM IPTG (Life Technologies, Carlsbad, Calif.) for 2 hours at 37° C. Cells (2 L) were centrifuged at 7,700 g for 15 min., weighed, and stored at −20° C. for at least 3 hours. The frozen cell pellet was resuspended in 100 mL ice-cold PBS containing 250 µL protease inhibitor cocktail (Sigma Chemical, St. Louis, Mo.) per gram of cells, sonicated at 3× for 1 min. with 15 second breaks. The cells were then centrifuged at 10,000 g for 20 min. The supernatant was mixed with 2 mL of 50% Glutathione Sepharose 4B resin (Pharmacia) on a shaker overnight at 4° C. The supernatant/resin was centrifuged at 1,500 g for 15 min., packed into empty Poly-Prep Chromatography Columns (Bio-Rad, Hercules, Calif.), washed with 30 mL PBS followed by 10 mL Factor Xa buffer (1 mM $CaCl_2$, 100 mM NaCl, and 50 mM Tris-HCl, pH 8.0). The peptides were cleaved from the column by adding 60 units of Factor Xa (Pharmacia) in 1 mL Factor Xa buffer, incubated overnight at 4° C., and separated by C18 HPLC (Beckman System Gold), using a 2 mL loop and flow rate of 2 mL/min with the following program: 10 min. of Buffer A (0.1% $TFA/H_2O$), 30 min. of gradient to Buffer B (0.1% TFA/ACN), 10 min. of Buffer A, 10 min. of gradient, and 10 min. of Buffer A. Peak fractions (1 mL each) were collected and screened by 10-20% Tricine-SDS gel electrophoresis. Fractions containing the peptides of FIG. 1 were pooled and dried down. Typical yields were several hundred micrograms of free peptides per liter of *E. coli* culture. Recombinant peptides were shown to have the same activities as their synthetic versions.

Example 5

Insulin Secretion from Dispersed Rat Islet Cells

Insulin secretion of dispersed rat islets mediated by a number of peptides of the present invention was measured as follows. Islets of Langerhans, isolated from SD rats (200-250 g), were digested using collagenase. The dispersed islet cells were treated with trypsin, seeded into 96 V-bottom plates, and pelleted. The cells were then cultured overnight in media with or without peptides of this invention. The media was aspirated, and the cells were pre-incubated with Krebs-Ringer-HEPES buffer containing 3 mM glucose for 30 minutes at 37° C. The pre-incubation buffer was removed, and the cells were incubated at 37° C. with Krebs-Ringer-HEPES buffer containing the appropriate glucose concentration (e.g., 8 mM) with or without peptides for an appropriate time. In some studies, an appropriate concentration of GLP-1 was also included. A portion of the supernatant was removed and its insulin content was measured by SPA. The results were expressed as "fold over control" (FOC). At a concentration of 300 nM, the polypeptide having the amino acid sequence SEQ ID NO:1+cys+PEG(43 kD), increased insulin secretion from dispersed islet cells by approximately 1.7-fold (FIG. 3).

In this assay, an increase of insulin secretion from dispersed rat islet cells was defined as an increase of at least 1.4-fold. The VPAC2 receptor agonist component of the polypeptides of this invention produced an increase in insulin secretion from dispersed islet cells by at least 1.4-fold to about 1.7-fold.

Example 6

Effect of PEGylated Peptides on Intraperitoneal Glucose Tolerance in Rats

The in vivo activity of the PEGylated peptides of this invention when administered subcutaneously was examined in rats. Rats fasted overnight were given a subcutaneous injection of control or PEGylated peptide (1-100 µg/kg). Three hours later, basal blood glucose was measured, and the rats were given 2 g/kg of glucose intraperitoneally. Blood glucose was measured again after 15, 30, and 60 min. The representative PEGylated peptide of this invention significantly reduced blood glucose levels relative to the vehicle following the IPGTT (Intraperitoneal Glucose Tolerance Test), with 17%-28% reduction in the glucose AUC (FIG. 4). This demonstrates that the PEGylated peptide has prolonged glucose lowering activity in vivo. In addition to the glucose lowering activity of the PEGylated peptides of the present invention, it also indicates prolonged peptide half-life in vivo. PACAP-27 has a very short half-life in vivo (<10 min.). The ability of the PEGylated peptides of the invention to lower blood glucose 3 hours following peptide administration is a clear indication that the peptide is present in the circulation at this time point and hence, has prolonged half-life relative to PACAP-27.

Example 7

Cyclic AMP SPA

CHO cells expressing the VPAC2 peptide were plated in 96-well plates at $8\times10^4$ cells/well and grown at 37° C. for 24 hours in αMEM, nucleosides, glutamine (Gibco/BRL, Rockville, Md.), 5% FBS, 100 µg/mL Pen/Strep, 0.4 mg/mL hygromycin, and 1.5 mg/mL Geneticin (Gibco/BRL). The media was removed and the plates were washed with PBS. The cells were incubated with a peptide (in 10 mM Hepes, 150 mM NaCL, 5 mM KCL, 2.5 mM $CaCl_2$, 1.2 mM $KH_2PO_4$, 1.2 mM $MgSO_4$, 25 mM $NaHCO_3$ (pH 7.4) with 1% BSA and 100 µM IBMX) for 15 min. at 37° C. Cyclic AMP in the cell extracts was quantitated using the cAMP SPA direct screening assay system (Amersham Pharmacia Biotech Inc., Piscataway, N.J.,). The amount of cAMP present in the lysates was determined following instructions provided with this kit. The amount of cAMP (in pmol) produced at each concentration of peptide was plotted and analyzed by nonlinear regression using Prizm software to determine the $EC_{50}$ for each peptide.

The polypeptides of this invention are designed based on VIP, which has been shown to lack activity at PAC1 (Vaudry, et al., Pharmacol. Rev. 52:269-324, 2000). Therefore, it is believed that the polypeptides of this invention do not possess appreciable activity at PAC1.

The results of this assay with representative polypeptides of this invention are shown in Table 1 below. Peptides identified as P5, P7, P8, P12, and P12+PEG are all potent agonists of the VPAC2 receptor, activating the receptor to 100% the maximal level of receptor activation achieved by the endogenous peptide, PACAP-27. Furthermore, the peptides identified as P5, P7, P8, P12, and P12+PEG are selective VPAC2 receptor agonists, possessing very weak agonist activity on VPAC1. PACAP-27 is a potent agonist of VPAC1.

TABLE 1

| Peptide | SEQ ID NO. | VPAC2 EC$_{50}$ (nM) | VPAC1 EC$_{50}$ (nM) |
|---|---|---|---|
| PACAP-27 | SEQ ID NO: 116 | 0.09 | 0.35 |
| P5 | SEQ ID NO: 1 | 0.33 | 232.5 |
| P7 | SEQ ID NO: 5 | 7.81 | >1000 |
| P8 | SEQ ID NO: 2 | 0.19 | 130.5 |
| P12 | SEQ ID NO: 1 + Cys at C-terminus | 0.38 | >1000 |
| P12 | plus 22 kD PEG | 1.32 | >1000 |
| P12 | plus 43 kD PEG | 4.19 | >1000 |

Example 8

Pharmaceutical Composition—IV and SC Formulations

A sterile IV injectable formulation is prepared with 4 mg of a polypeptide of SEQ ID NO: 1, or a derivatized polypeptide having equivalent of 4 mg polypeptide content, and 1L sterile saline, using any manufacturing process well known in the art. Higher concentrations of polypeptide may be used for SC formulation. In the case of the polypeptide identified as SEQ ID NO: 1, or a derivatized polypeptide, 4 mg is dissolved in 100 mL saline or DMSO and sterile vials after aseptic filtration, are filled with the composition.

Example 9

Stability of the Formulations Comprising the Peptides of this Invention

Figure 5:
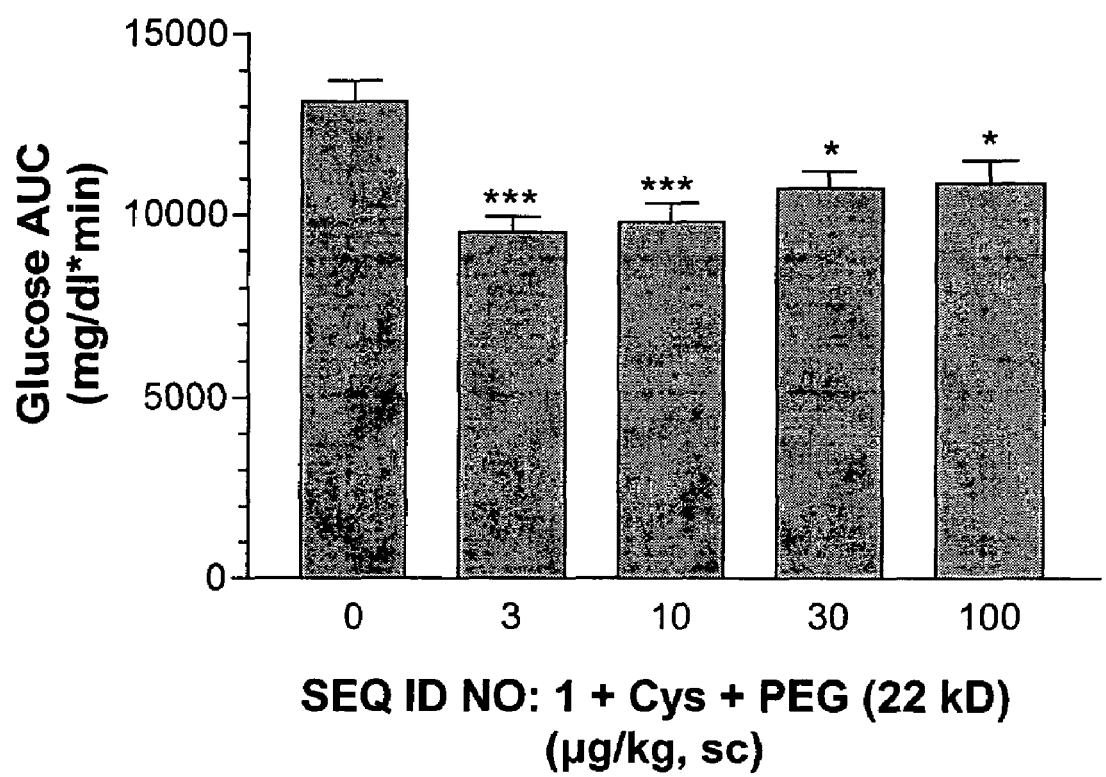
FIG. 5 is a bar chart demonstrating enhanced glucose disposal in the rat by subcutaneous (SC) route of administration of a PEGylated peptide of this invention.
Figure 6:
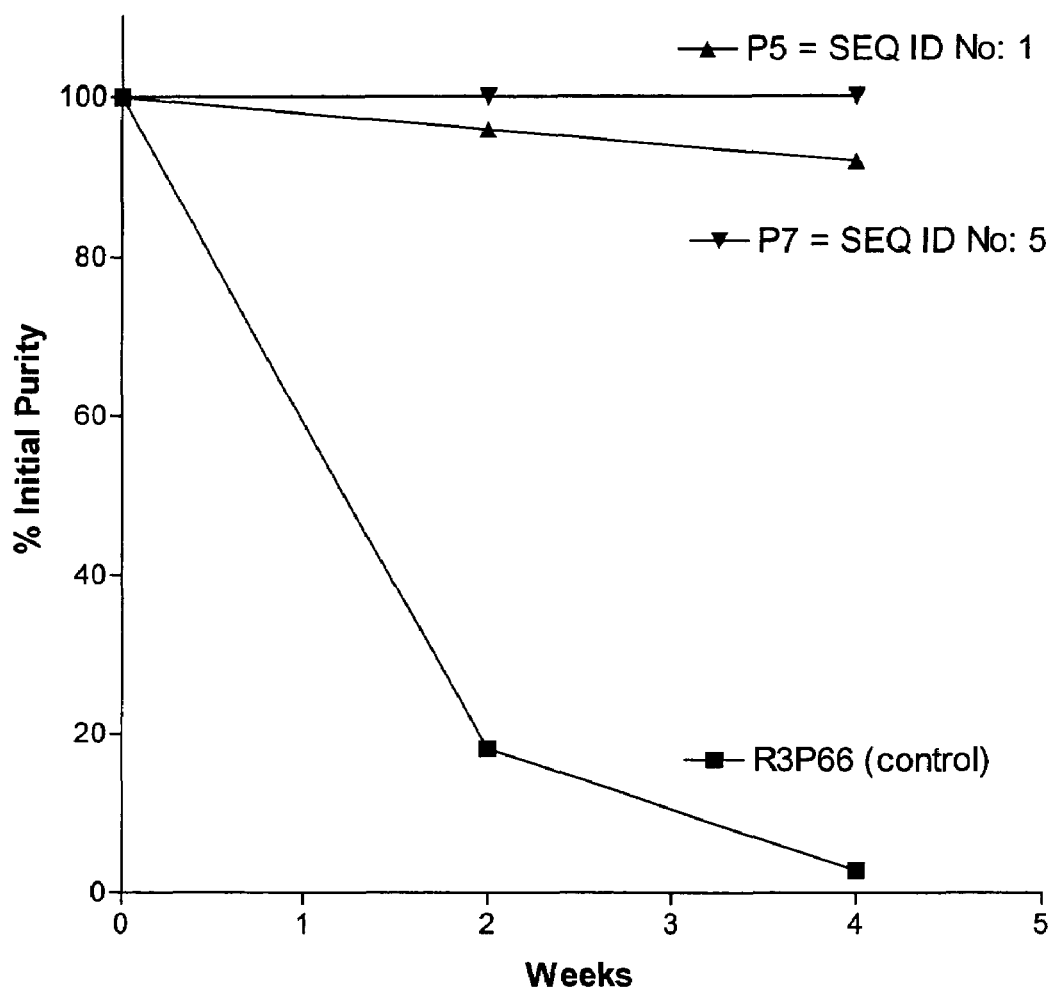
FIG. 6 depicts stability trends of three VPAC2 analogues (P5, P7, and the control, R3P66) at 1 mg/mL in an aqueous solution containing 150 mM NaCl and 20 mM phosphate at pH 8.0 during incubation at 40° C. The samples were analyzed by capillary electrophoresis to determine the purity of the peptide. The purity at 2- and 4-week time points was normalized by the percent purity at initial.

The formulations described in Example 8 were placed in constant stability chamber. Samples were removed periodically for analysis by capillary electrophoresis which is the most sensitive method to detect degradation of polypeptide in these formulations. The area of various peaks was summed and the area for peak of the parent polypeptide is divided by the total peak area (FIGS. 5 and 6). The quotient is the % purity. Since there are impurities present in the fresh polypeptide, the purity change is normalized by dividing the purity at different time point by the initial purity.

Example 10

Generation of Peptide Specific Antibodies and Peptide Measurement by ELISA

Polyclonal antibodies specific to the polypeptides of the present invention were generated by synthesizing a specific fragment of a polypeptide of this invention using an ABI 433A peptide synthesizer. The peptide was then cleaved from the resin, and purified on a Beckman System Gold Analytical and Preparative HPLC system. A Perspective MALDI mass spectrophotometer system was used to identify the correct product. The peptide was dried using a lyophilizer. The peptide (2 mg) was then conjugated to keyhole limpet hemocyanin (KLH) via the free sulphydryl group on the Cys.

Female New Zealand White rabbits were immunized on Day 0, 14, 35, 56, and 77. On Day 0, each rabbit was injected subcutaneous with 250 µg peptide and complete Freund's adjuvant. Subsequent immunizations utilized 125 µg peptide per rabbit. Bleeds were started on Day 21 and continued at 21-day intervals thereafter. Purification of anti-peptide antibodies was performed by passing the crude serum over a specific peptide affinity purification column. The antibody titer was determined by ELISA.

Figure 7:
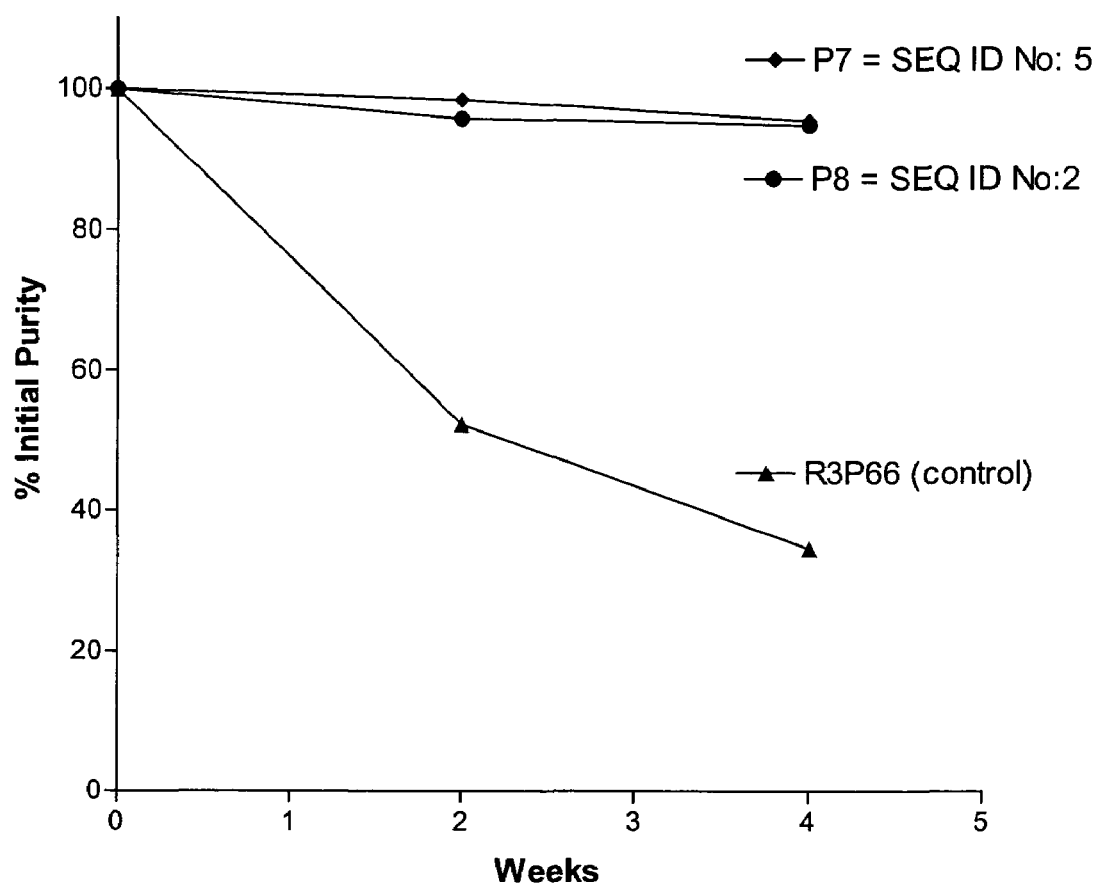
FIG. 7 depicts stability trends of three VPAC2 analogues (P7, P8, and the control, R3P66) at 2 mg/mL in dimethylsulfoxide (DMSO) during incubation at 40° C. The samples were analyzed by capillary electrophoresis to determine the purity of the peptide. The purity at 2- and 4-week time points was normalized by the percent purity at initial.
Figure 8:
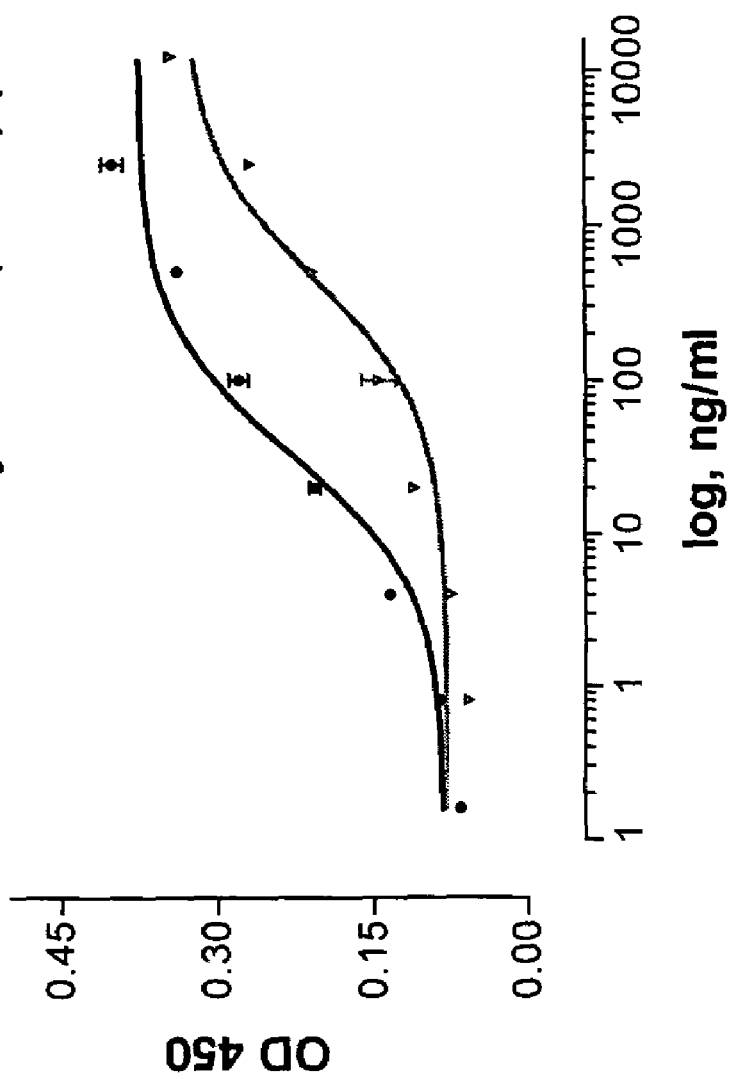
FIG. 8 illustrates the selective recognition of a full-length PEGylated peptide over a similar PEGylated peptide in which there is a single amino acid deletion at the N-terminus.

A 96-well Immulon 4HBX plate was coated with a C-terminal Morphosys F(ab) antibody, specific to the peptides of the present invention, and allowed to incubate overnight at 4° C. The plate was then blocked to prevent non-specific binding. Then, peptide standards (2500 ng/mL-160 pg/mL) were diluted in 33% plasma and the samples were diluted 1:3 in buffer followed by incubation for 1.5 hours at room temperature. After washing, a polyclonal N-terminal antibody specific to the peptides of this invention was incubated on the plate for one hour. This was followed by the addition of horseradish peroxidase (HRP)-donkey-anti-rabbit antibody and the samples and standards were incubated for another hour. Detection was assessed following incubation with 3,3',5,5'-tetramethylbenzidine (TMB) solution, and the plate is read at OD$_{450}$ (FIG. 7).

Demonstration of the activity of the polypeptides of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia; atherosclerotic disease and related disorders such as hypertriglyceridemia and hypercholesteremia; and obesity, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test polypeptide once daily for 14 days. At this point, the animals are bled again by eye or tail vein and blood glucose levels were determined. In each case, glucose levels are measured with a Glucometer Elite XL (Bayer Corporation, Elkhart, Ind.).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test polypeptide once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test polypeptide for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test polypeptide for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver, et al., (Proc. Natl. Acad. Sci. USA 98:5306-5311, 2001).

Method for Measuring an Effect on Cardiovascular Parameters

Cardiovascular parameters (e.g., heart rate and blood pressure) are also evaluated. SHR rats are orally dosed once daily with vehicle or test polypeptide for 2 weeks. Blood pressure and heart rate are determined using a tail-cuff method as described by Grinsell, et al., (Am. J. Hypertens.

13:370-375, 2000). In monkeys, blood pressure and heart rate are monitored as described by Shen, et al., (J. Pharmacol. Exp. Therap. 278:1435-1443, 1996).

Evaluation of Compound's Efficacy on the Reduction of Food Intake (Suppression of Appetite) in Lean Overnight Fasted Rats Fasted-Refed Acute Feeding Assay The purpose of this protocol is to determine the effect of a single dose of an unknown compound on food consumption of lean overnight fasted rats. The fasted-refed rat model is frequently used in the field of obesity to identify compounds with potential for anorectic effects. This animal model has been successfully used in the identification and characterization of the efficacy profile of compounds that are or have been used in the management of body weight in obese humans (see, e.g., Balvet, et al., Gen. Pharmacol. 13:293-297, 1982; Grignaschi, et al., Br. J. Pharmacol. 127:1190-1194, 1999; McTavish and Heel, Drug 43:713-733, 1992; Rowland, et al., Life Sci. 36:2295-2300, 1985).

A typical study includes 60-80 male rats (n=10/treatment group) with an average body weight of approximately 280 g. Rats are kept in standard animal rooms under controlled temperature and humidity and a 12/12 light dark cycle. Rats are single-housed in suspended cages with a mesh floor. Water and food are continuously available unless the animals are being fasted for the study.

The vehicle test: The rats are grouped based upon their performance on a vehicle test. The vehicle test is performed between 2 and 7 days before the efficacy test. The rats are fasted overnight during the dark phase (total of approx. 16-18 hrs). The animal is dosed with 0.5 mL deionized water. One hour after dosing, pre-weighed food jars are returned to the animal home cage. The rats are allowed one hour of feeding time. After 1 hour, the spillage is returned to the food jar and the amount of food consumed is determined. The rats are assigned to groups so that the mean and standard error of the mean of 1-hour food consumption are similar between groups.

The efficacy test: The rats are fasted overnight during the dark phase (total of approx. 16-18 hr). The animal is treated with an assigned dose of polypeptide. One hour after dosing, pre-weighed food jars are returned to the cage. Food intake is recorded 30, 60, 90, 180, and 240 minutes post-food return. At each time point, spillage is returned to the food jar and then the food jars are weighed. The amount of food consumed is determined for each time point. Difference between treatment group is determined using appropriate statistical analysis.

Evaluation of Compound's Efficacy on the Reduction of Body Weight and Food and Water Consumption in Obese Zucker fa/fa Rats Chronic Feeding Assay The purpose of this protocol is to determine the effect of chronic administration of an unknown compound on body weight and food and water consumption in obese Zucker fa/fa rats. Obese Zucker fa/fa rats are frequently used in the determination of compound efficacy in the reduction of body weight. This animal model has been successfully used in the identification and characterization of the efficacy profile of compounds that are or have been used in the management of body weight in obese humans (see, e.g., Al-Barazanji, et al., Obes Res. 8:317-323, 2000; Assimacopoulos-Jeannet, et al., Am. J. Physiol. 260(2 Pt 2):R278-283, 1991; Dryden, et al., Horm. Metab. Res. 31:363-366, 1999; Edwards and Stevens, Pharmacol. Biochem. Behav. 47:865-872, 1994; Grinker, et al., Pharmacol. Biochem. Behav. 12:265-275, 1980).

A typical study includes 60-80 male Zucker fa/fa (n=10/treatment group) with an average body weight of approximately 550 g. Rats are kept in standard animal rooms under controlled temperature and humidity and a 12/12 light dark cycle. Water and food are continuously available. Rats are single-housed in large rat shoeboxes containing grid floor. Animals are adapted to the grid floors and sham-dosed with study vehicle for at least four days before the recording of two-days baseline measurement of body weight and 24-hr food and water consumption. Rats are assigned to one of 6-8 treatment groups based upon their body weight on baseline. The groups are set up so that the mean and standard error of the mean of body weight were similar.

Animals are orally gavaged daily before the dark phase of the LD/cycle for a pre-determined number of days (typically 6-14 days) with their assigned dose of polypeptide. At this time, body weight, food and water consumption are measured. On the final day, animals are euthanized by $CO_2$ inhalation, and the body weight is measured.

The efficacy of polypeptides of this invention on the reduction or control of body weight may be determined by using this chronic feeding assay.

All publications and patents mentioned in the above specification are incorporated herein by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims. Those skilled in the art will recognize, or be able to ascertain using no more than routine experimentation, many equivalents to the specific embodiments of the invention described herein. Such equivalents are intended to be encompassed by the following claims.

We claim:

1. A polypeptide having Vasoactive intestinal peptide receptor type 2 (VPAC2), agonist activity, said polypeptide consisting of the amino acid sequence of SEQ ID NO: 115, functionally equivalent fragments, derivatives, and variants thereof having at least 90% identity to the amino acid sequence of SEQ ID NO:115.

* * * * *

SEQUENCE LISTING

<160> NUMBER OF SEQ ID NOS: 264

<210> SEQ ID NO 1
<211> LENGTH: 31
<212> TYPE: PRT
<213> ORGANISM: Homo sapiens

```
<400> SEQUENCE: 1

His Ser Asp Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Arg Tyr
            20                  25                  30

<210> SEQ ID NO 2
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Histidine at position 1 is acetylated.

<400> SEQUENCE: 2

His Thr Asp Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Arg Tyr
            20                  25                  30

<210> SEQ ID NO 3
<211> LENGTH: 31
<212> TYPE: PRT
<213> ORGANISM: Homo sapiens

<400> SEQUENCE: 3

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Arg Tyr
            20                  25                  30

<210> SEQ ID NO 4
<211> LENGTH: 29
<212> TYPE: PRT
<213> ORGANISM: Homo sapiens

<400> SEQUENCE: 4

His Ser Asp Ala Val Phe Thr Asp Gln Tyr Thr Arg Leu Arg Lys Gln
1               5                   10                  15

Val Ala Ala Lys Lys Tyr Leu Gln Ser Ile Lys Gln Lys
            20                  25

<210> SEQ ID NO 5
<211> LENGTH: 31
<212> TYPE: PRT
<213> ORGANISM: Homo sapiens

<400> SEQUENCE: 5

His Thr Glu Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Arg Tyr
            20                  25                  30

<210> SEQ ID NO 6
<211> LENGTH: 31
<212> TYPE: PRT
<213> ORGANISM: Homo sapiens

<400> SEQUENCE: 6

His Ser Asp Ala Val Phe Thr Asp Gln Tyr Thr Arg Leu Arg Lys Gln
1               5                   10                  15
```

-continued

Leu Ala Val Lys Lys Tyr Leu Gln Asp Ile Lys Gln Gly Gly Thr
            20                  25                  30

<210> SEQ ID NO 7
<211> LENGTH: 30
<212> TYPE: PRT
<213> ORGANISM: Homo sapiens

<400> SEQUENCE: 7

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Arg
            20                  25                  30

<210> SEQ ID NO 8
<211> LENGTH: 31
<212> TYPE: PRT
<213> ORGANISM: Homo sapiens

<400> SEQUENCE: 8

His Ser Asp Ala Val Phe Thr Asp Gln Tyr Thr Arg Leu Arg Lys Gln
1               5                   10                  15

Leu Ala Ala Lys Lys Tyr Leu Gln Thr Ile Lys Gln Lys Arg Tyr
            20                  25                  30

<210> SEQ ID NO 9
<211> LENGTH: 31
<212> TYPE: PRT
<213> ORGANISM: Homo sapiens

<400> SEQUENCE: 9

His Ser Asp Ala Val Phe Thr Asp Gln Tyr Thr Arg Leu Arg Lys Gln
1               5                   10                  15

Met Ala Ala Lys Lys Tyr Leu Gln Thr Ile Lys Gln Lys Arg Tyr
            20                  25                  30

<210> SEQ ID NO 10
<211> LENGTH: 31
<212> TYPE: PRT
<213> ORGANISM: Homo sapiens

<400> SEQUENCE: 10

His Ser Asp Ala Val Phe Thr Asp Gln Tyr Thr Arg Leu Arg Lys Gln
1               5                   10                  15

Met Ala Ala His Lys Tyr Leu Gln Ser Ile Lys Gln Lys Arg Tyr
            20                  25                  30

<210> SEQ ID NO 11
<211> LENGTH: 31
<212> TYPE: PRT
<213> ORGANISM: Homo sapiens

<400> SEQUENCE: 11

His Ser Asp Ala Val Phe Thr Asp Gln Tyr Thr Arg Leu Arg Lys Gln
1               5                   10                  15

Met Ala Ala Lys His Tyr Leu Gln Ser Ile Lys Gln Lys Arg Tyr
            20                  25                  30

<210> SEQ ID NO 12
<211> LENGTH: 30
<212> TYPE: PRT
<213> ORGANISM: Homo sapiens

```
<400> SEQUENCE: 12

His Ser Asp Ala Val Phe Thr Asp Gln Tyr Thr Arg Leu Arg Lys Gln
1               5                   10                  15

Met Ala Gly Lys Lys Tyr Leu Gln Ser Ile Lys Gln Lys Arg
            20                  25                  30

<210> SEQ ID NO 13
<211> LENGTH: 30
<212> TYPE: PRT
<213> ORGANISM: Homo sapiens

<400> SEQUENCE: 13

His Ser Asp Ala Val Phe Thr Asp Gln Tyr Thr Arg Leu Arg Lys Gln
1               5                   10                  15

Met Ala Lys Lys Lys Tyr Leu Gln Ser Ile Lys Gln Lys Arg
            20                  25                  30

<210> SEQ ID NO 14
<211> LENGTH: 30
<212> TYPE: PRT
<213> ORGANISM: Homo sapiens

<400> SEQUENCE: 14

His Ser Asp Ala Val Phe Thr Asp Gln Tyr Thr Arg Leu Arg Lys Gln
1               5                   10                  15

Met Ala Arg Lys Lys Tyr Leu Gln Ser Ile Lys Gln Lys Arg
            20                  25                  30

<210> SEQ ID NO 15
<211> LENGTH: 30
<212> TYPE: PRT
<213> ORGANISM: Homo sapiens

<400> SEQUENCE: 15

His Ser Asp Ala Val Phe Thr Asp Gln Tyr Thr Arg Leu Arg Lys Gln
1               5                   10                  15

Met Ala Ser Lys Lys Tyr Leu Gln Ser Ile Lys Gln Lys Arg
            20                  25                  30

<210> SEQ ID NO 16
<211> LENGTH: 30
<212> TYPE: PRT
<213> ORGANISM: Homo sapiens

<400> SEQUENCE: 16

His Ser Asp Ala Val Phe Thr Asp Gln Tyr Thr Arg Leu Arg Lys Gln
1               5                   10                  15

Met Ala Ala Lys Lys Tyr Leu Gln Ser Ile Pro Gln Lys Arg
            20                  25                  30

<210> SEQ ID NO 17
<211> LENGTH: 30
<212> TYPE: PRT
<213> ORGANISM: Homo sapiens

<400> SEQUENCE: 17

His Ser Asp Ala Val Phe Thr Asp Gln Tyr Thr Arg Leu Arg Lys Gln
1               5                   10                  15

Met Ala Ala Lys Lys Tyr Leu Gln Ser Ile Gln Gln Lys Arg
            20                  25                  30
```

```
<210> SEQ ID NO 18
<211> LENGTH: 30
<212> TYPE: PRT
<213> ORGANISM: Homo sapiens

<400> SEQUENCE: 18

His Ser Asp Ala Val Phe Thr Asp Gln Tyr Thr Arg Leu Arg Lys Gln
1               5                   10                  15

Met Ala Ala Lys Lys Tyr Leu Gln Ser Ile Arg Gln Lys Arg
            20                  25                  30

<210> SEQ ID NO 19
<211> LENGTH: 30
<212> TYPE: PRT
<213> ORGANISM: Homo sapiens

<400> SEQUENCE: 19

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Arg Arg
            20                  25                  30

<210> SEQ ID NO 20
<211> LENGTH: 30
<212> TYPE: PRT
<213> ORGANISM: Homo sapiens

<400> SEQUENCE: 20

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Ala
            20                  25                  30

<210> SEQ ID NO 21
<211> LENGTH: 30
<212> TYPE: PRT
<213> ORGANISM: Homo sapiens

<400> SEQUENCE: 21

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Phe
            20                  25                  30

<210> SEQ ID NO 22
<211> LENGTH: 30
<212> TYPE: PRT
<213> ORGANISM: Homo sapiens

<400> SEQUENCE: 22

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys His
            20                  25                  30

<210> SEQ ID NO 23
<211> LENGTH: 30
<212> TYPE: PRT
<213> ORGANISM: Homo sapiens

<400> SEQUENCE: 23

His Ser Asp Ala Val Phe Thr Asp Gln Tyr Thr Arg Leu Arg Lys Gln
1               5                   10                  15
```

Met Ala Ala Lys Lys Tyr Leu Gln Ser Ile Lys Gln Lys Ile
            20                  25                  30

<210> SEQ ID NO 24
<211> LENGTH: 30
<212> TYPE: PRT
<213> ORGANISM: Homo sapiens

<400> SEQUENCE: 24

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Lys
            20                  25                  30

<210> SEQ ID NO 25
<211> LENGTH: 30
<212> TYPE: PRT
<213> ORGANISM: Homo sapiens

<400> SEQUENCE: 25

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Leu
            20                  25                  30

<210> SEQ ID NO 26
<211> LENGTH: 30
<212> TYPE: PRT
<213> ORGANISM: Homo sapiens

<400> SEQUENCE: 26

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Met
            20                  25                  30

<210> SEQ ID NO 27
<211> LENGTH: 30
<212> TYPE: PRT
<213> ORGANISM: Homo sapiens

<400> SEQUENCE: 27

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Pro
            20                  25                  30

<210> SEQ ID NO 28
<211> LENGTH: 30
<212> TYPE: PRT
<213> ORGANISM: Homo sapiens

<400> SEQUENCE: 28

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Gln
            20                  25                  30

<210> SEQ ID NO 29
<211> LENGTH: 30
<212> TYPE: PRT
<213> ORGANISM: Homo sapiens

```
<400> SEQUENCE: 29

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Ser
            20                  25                  30

<210> SEQ ID NO 30
<211> LENGTH: 30
<212> TYPE: PRT
<213> ORGANISM: Homo sapiens

<400> SEQUENCE: 30

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Thr
            20                  25                  30

<210> SEQ ID NO 31
<211> LENGTH: 30
<212> TYPE: PRT
<213> ORGANISM: Homo sapiens

<400> SEQUENCE: 31

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Val
            20                  25                  30

<210> SEQ ID NO 32
<211> LENGTH: 30
<212> TYPE: PRT
<213> ORGANISM: Homo sapiens

<400> SEQUENCE: 32

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Trp
            20                  25                  30

<210> SEQ ID NO 33
<211> LENGTH: 30
<212> TYPE: PRT
<213> ORGANISM: Homo sapiens

<400> SEQUENCE: 33

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Tyr
            20                  25                  30

<210> SEQ ID NO 34
<211> LENGTH: 30
<212> TYPE: PRT
<213> ORGANISM: Homo sapiens

<400> SEQUENCE: 34

His Ser Asp Ala Val Phe Thr Asp Gln Tyr Thr Arg Leu Arg Lys Gln
1               5                   10                  15

Met Ala Gly Lys Lys Tyr Leu Gln Ser Ile Lys Gln Arg Ile
            20                  25                  30
```

```
<210> SEQ ID NO 35
<211> LENGTH: 30
<212> TYPE: PRT
<213> ORGANISM: Homo sapiens

<400> SEQUENCE: 35

His Ser Asp Ala Val Phe Thr Asp Gln Tyr Thr Arg Leu Arg Lys Gln
1               5                   10                  15

Met Ala Lys Lys Lys Tyr Leu Gln Ser Ile Lys Gln Arg Ile
            20                  25                  30

<210> SEQ ID NO 36
<211> LENGTH: 30
<212> TYPE: PRT
<213> ORGANISM: Homo sapiens

<400> SEQUENCE: 36

His Ser Asp Ala Val Phe Thr Asp Gln Tyr Thr Arg Leu Arg Lys Gln
1               5                   10                  15

Met Ala Ser Lys Lys Tyr Leu Gln Ser Ile Lys Gln Arg Ile
            20                  25                  30

<210> SEQ ID NO 37
<211> LENGTH: 30
<212> TYPE: PRT
<213> ORGANISM: Homo sapiens

<400> SEQUENCE: 37

His Ser Asp Ala Val Phe Thr Asp Gln Tyr Thr Arg Leu Arg Lys Gln
1               5                   10                  15

Met Ala Ala Lys Lys Tyr Leu Gln Ser Ile Pro Gln Arg Ile
            20                  25                  30

<210> SEQ ID NO 38
<211> LENGTH: 30
<212> TYPE: PRT
<213> ORGANISM: Homo sapiens

<400> SEQUENCE: 38

His Ser Asp Ala Val Phe Thr Asp Gln Tyr Thr Arg Leu Arg Lys Gln
1               5                   10                  15

Met Ala Ser Lys Lys Tyr Leu Gln Ser Ile Arg Gln Arg Ile
            20                  25                  30

<210> SEQ ID NO 39
<211> LENGTH: 31
<212> TYPE: PRT
<213> ORGANISM: Homo sapiens

<400> SEQUENCE: 39

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Gln Lys Arg Tyr
            20                  25                  30

<210> SEQ ID NO 40
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Histidine at position 1 is acetylated.
```

<400> SEQUENCE: 40

His Thr Asp Ala Val Phe Thr Asp Asn Tyr Thr Arg Leu Arg Lys Gln
1               5                   10                  15

Val Ala Ala Lys Lys Tyr Leu Gln Ser Ile Lys Gln Lys Arg Tyr
            20                  25                  30

<210> SEQ ID NO 41
<211> LENGTH: 31
<212> TYPE: PRT
<213> ORGANISM: Homo sapiens

<400> SEQUENCE: 41

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Arg Tyr
            20                  25                  30

<210> SEQ ID NO 42
<211> LENGTH: 29
<212> TYPE: PRT
<213> ORGANISM: Homo sapiens

<400> SEQUENCE: 42

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Gln Lys
            20                  25

<210> SEQ ID NO 43
<211> LENGTH: 31
<212> TYPE: PRT
<213> ORGANISM: Homo sapiens

<400> SEQUENCE: 43

His Thr Glu Ala Val Phe Thr Asp Asn Tyr Thr Arg Leu Arg Lys Gln
1               5                   10                  15

Val Ala Ala Lys Lys Tyr Leu Gln Ser Ile Lys Gln Lys Arg Tyr
            20                  25                  30

<210> SEQ ID NO 44
<211> LENGTH: 31
<212> TYPE: PRT
<213> ORGANISM: Homo sapiens

<400> SEQUENCE: 44

His Ser Asp Ala Val Phe Thr Asp Asn Tyr Thr Arg Leu Arg Lys Gln
1               5                   10                  15

Leu Ala Val Lys Lys Tyr Leu Gln Asp Ile Lys Gln Gly Gly Thr
            20                  25                  30

<210> SEQ ID NO 45
<211> LENGTH: 30
<212> TYPE: PRT
<213> ORGANISM: Homo sapiens

<400> SEQUENCE: 45

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Arg
            20                  25                  30

```
<210> SEQ ID NO 46
<211> LENGTH: 31
<212> TYPE: PRT
<213> ORGANISM: Homo sapiens

<400> SEQUENCE: 46

His Ser Asp Ala Val Phe Thr Asp Asn Tyr Thr Arg Leu Arg Lys Gln
1               5                   10                  15

Leu Ala Ala Lys Lys Tyr Leu Gln Thr Ile Lys Gln Lys Arg Tyr
            20                  25                  30

<210> SEQ ID NO 47
<211> LENGTH: 31
<212> TYPE: PRT
<213> ORGANISM: Homo sapiens

<400> SEQUENCE: 47

His Ser Asp Ala Val Phe Thr Asp Asn Tyr Thr Arg Leu Arg Lys Gln
1               5                   10                  15

Met Ala Ala Lys Lys Tyr Leu Gln Thr Ile Lys Gln Lys Arg Tyr
            20                  25                  30

<210> SEQ ID NO 48
<211> LENGTH: 31
<212> TYPE: PRT
<213> ORGANISM: Homo sapiens

<400> SEQUENCE: 48

His Ser Asp Ala Val Phe Thr Asp Asn Tyr Thr Arg Leu Arg Lys Gln
1               5                   10                  15

Met Ala Ala His Lys Tyr Leu Gln Ser Ile Lys Gln Lys Arg Tyr
            20                  25                  30

<210> SEQ ID NO 49
<211> LENGTH: 31
<212> TYPE: PRT
<213> ORGANISM: Homo sapiens

<400> SEQUENCE: 49

His Ser Asp Ala Val Phe Thr Asp Asn Tyr Thr Arg Leu Arg Lys Gln
1               5                   10                  15

Met Ala Ala Lys His Tyr Leu Gln Ser Ile Lys Gln Lys Arg Tyr
            20                  25                  30

<210> SEQ ID NO 50
<211> LENGTH: 30
<212> TYPE: PRT
<213> ORGANISM: Homo sapiens

<400> SEQUENCE: 50

His Ser Asp Ala Val Phe Thr Asp Asn Tyr Thr Arg Leu Arg Lys Gln
1               5                   10                  15

Met Ala Gly Lys Lys Tyr Leu Gln Ser Ile Lys Gln Lys Arg
            20                  25                  30

<210> SEQ ID NO 51
<211> LENGTH: 30
<212> TYPE: PRT
<213> ORGANISM: Homo sapiens

<400> SEQUENCE: 51

His Ser Asp Ala Val Phe Thr Asp Asn Tyr Thr Arg Leu Arg Lys Gln
1               5                   10                  15
```

Met Ala Lys Lys Lys Tyr Leu Gln Ser Ile Lys Gln Lys Arg
            20                  25                  30

<210> SEQ ID NO 52
<211> LENGTH: 30
<212> TYPE: PRT
<213> ORGANISM: Homo sapiens

<400> SEQUENCE: 52

His Ser Asp Ala Val Phe Thr Asp Asn Tyr Thr Arg Leu Arg Lys Gln
1               5                   10                  15

Met Ala Arg Lys Lys Tyr Leu Gln Ser Ile Lys Gln Lys Arg
            20                  25                  30

<210> SEQ ID NO 53
<211> LENGTH: 30
<212> TYPE: PRT
<213> ORGANISM: Homo sapiens

<400> SEQUENCE: 53

His Ser Asp Ala Val Phe Thr Asp Asn Tyr Thr Arg Leu Arg Lys Gln
1               5                   10                  15

Met Ala Ser Lys Lys Tyr Leu Gln Ser Ile Lys Gln Lys Arg
            20                  25                  30

<210> SEQ ID NO 54
<211> LENGTH: 30
<212> TYPE: PRT
<213> ORGANISM: Homo sapiens

<400> SEQUENCE: 54

His Ser Asp Ala Val Phe Thr Asp Asn Tyr Thr Arg Leu Arg Lys Gln
1               5                   10                  15

Met Ala Ala Lys Lys Tyr Leu Gln Ser Ile Pro Gln Lys Arg
            20                  25                  30

<210> SEQ ID NO 55
<211> LENGTH: 30
<212> TYPE: PRT
<213> ORGANISM: Homo sapiens

<400> SEQUENCE: 55

His Ser Asp Ala Val Phe Thr Asp Asn Tyr Thr Arg Leu Arg Lys Gln
1               5                   10                  15

Met Ala Ala Lys Lys Tyr Leu Gln Ser Ile Gln Gln Lys Arg
            20                  25                  30

<210> SEQ ID NO 56
<211> LENGTH: 30
<212> TYPE: PRT
<213> ORGANISM: Homo sapiens

<400> SEQUENCE: 56

His Ser Asp Ala Val Phe Thr Asp Asn Tyr Thr Arg Leu Arg Lys Gln
1               5                   10                  15

Met Ala Ala Lys Lys Tyr Leu Gln Ser Ile Arg Gln Lys Arg
            20                  25                  30

<210> SEQ ID NO 57
<211> LENGTH: 30
<212> TYPE: PRT
<213> ORGANISM: Homo sapiens

```
<400> SEQUENCE: 57

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Arg Arg
            20                  25                  30

<210> SEQ ID NO 58
<211> LENGTH: 30
<212> TYPE: PRT
<213> ORGANISM: Homo sapiens

<400> SEQUENCE: 58

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Ala
            20                  25                  30

<210> SEQ ID NO 59
<211> LENGTH: 30
<212> TYPE: PRT
<213> ORGANISM: Homo sapiens

<400> SEQUENCE: 59

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Phe
            20                  25                  30

<210> SEQ ID NO 60
<211> LENGTH: 30
<212> TYPE: PRT
<213> ORGANISM: Homo sapiens

<400> SEQUENCE: 60

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys His
            20                  25                  30

<210> SEQ ID NO 61
<211> LENGTH: 30
<212> TYPE: PRT
<213> ORGANISM: Homo sapiens

<400> SEQUENCE: 61

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Ile
            20                  25                  30

<210> SEQ ID NO 62
<211> LENGTH: 30
<212> TYPE: PRT
<213> ORGANISM: Homo sapiens

<400> SEQUENCE: 62

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Lys
            20                  25                  30
```

```
<210> SEQ ID NO 63
<211> LENGTH: 30
<212> TYPE: PRT
<213> ORGANISM: Homo sapiens

<400> SEQUENCE: 63

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Leu
            20                  25                  30

<210> SEQ ID NO 64
<211> LENGTH: 30
<212> TYPE: PRT
<213> ORGANISM: Homo sapiens

<400> SEQUENCE: 64

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Met
            20                  25                  30

<210> SEQ ID NO 65
<211> LENGTH: 30
<212> TYPE: PRT
<213> ORGANISM: Homo sapiens

<400> SEQUENCE: 65

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Pro
            20                  25                  30

<210> SEQ ID NO 66
<211> LENGTH: 30
<212> TYPE: PRT
<213> ORGANISM: Homo sapiens

<400> SEQUENCE: 66

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Gln
            20                  25                  30

<210> SEQ ID NO 67
<211> LENGTH: 30
<212> TYPE: PRT
<213> ORGANISM: Homo sapiens

<400> SEQUENCE: 67

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Ser
            20                  25                  30

<210> SEQ ID NO 68
<211> LENGTH: 30
<212> TYPE: PRT
<213> ORGANISM: Homo sapiens

<400> SEQUENCE: 68

His Ser Asp Ala Val Phe Thr Asp Asn Tyr Thr Arg Leu Arg Lys Gln
1               5                   10                  15
```

Met Ala Ala Lys Lys Tyr Leu Gln Ser Ile Lys Gln Lys Thr
            20                  25                  30

<210> SEQ ID NO 69
<211> LENGTH: 30
<212> TYPE: PRT
<213> ORGANISM: Homo sapiens

<400> SEQUENCE: 69

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Val
            20                  25                  30

<210> SEQ ID NO 70
<211> LENGTH: 30
<212> TYPE: PRT
<213> ORGANISM: Homo sapiens

<400> SEQUENCE: 70

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Trp
            20                  25                  30

<210> SEQ ID NO 71
<211> LENGTH: 30
<212> TYPE: PRT
<213> ORGANISM: Homo sapiens

<400> SEQUENCE: 71

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Gln Lys Tyr
            20                  25                  30

<210> SEQ ID NO 72
<211> LENGTH: 30
<212> TYPE: PRT
<213> ORGANISM: Homo sapiens

<400> SEQUENCE: 72

His Ser Asp Ala Val Phe Thr Asp Asn Tyr Thr Arg Leu Arg Lys Gln
1               5                   10                  15

Met Ala Gly Lys Lys Tyr Leu Gln Ser Ile Lys Gln Arg Ile
            20                  25                  30

<210> SEQ ID NO 73
<211> LENGTH: 30
<212> TYPE: PRT
<213> ORGANISM: Homo sapiens

<400> SEQUENCE: 73

His Ser Asp Ala Val Phe Thr Asp Asn Tyr Thr Arg Leu Arg Lys Gln
1               5                   10                  15

Met Ala Lys Lys Lys Tyr Leu Gln Ser Ile Lys Gln Arg Ile
            20                  25                  30

<210> SEQ ID NO 74
<211> LENGTH: 30
<212> TYPE: PRT
<213> ORGANISM: Homo sapiens -continued

<400> SEQUENCE: 74

His Ser Asp Ala Val Phe Thr Asp Asn Tyr Thr Arg Leu Arg Lys Gln
1               5                   10                  15

Met Ala Ser Lys Lys Tyr Leu Gln Ser Ile Lys Gln Arg Ile
            20                  25                  30

<210> SEQ ID NO 75
<211> LENGTH: 30
<212> TYPE: PRT
<213> ORGANISM: Homo sapiens

<400> SEQUENCE: 75

His Ser Asp Ala Val Phe Thr Asp Asn Tyr Thr Arg Leu Arg Lys Gln
1               5                   10                  15

Met Ala Ala Lys Lys Tyr Leu Gln Ser Ile Pro Gln Arg Ile
            20                  25                  30

<210> SEQ ID NO 76
<211> LENGTH: 30
<212> TYPE: PRT
<213> ORGANISM: Homo sapiens

<400> SEQUENCE: 76

His Ser Asp Ala Val Phe Thr Asp Asn Tyr Thr Arg Leu Arg Lys Gln
1               5                   10                  15

Met Ala Ser Lys Lys Tyr Leu Gln Ser Ile Arg Gln Arg Ile
            20                  25                  30

<210> SEQ ID NO 77
<211> LENGTH: 31
<212> TYPE: PRT
<213> ORGANISM: Homo sapiens

<400> SEQUENCE: 77

His Ser Asp Ala Val Phe Thr Asp Gln Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 78
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Histidine at position 1 is acetylated.

<400> SEQUENCE: 78

His Thr Asp Ala Val Phe Thr Asp Gln Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 79
<211> LENGTH: 31
<212> TYPE: PRT
<213> ORGANISM: Homo sapiens

<400> SEQUENCE: 79

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Arg Tyr
            20                  25                  30

<210> SEQ ID NO 80
<211> LENGTH: 29
<212> TYPE: PRT
<213> ORGANISM: Homo sapiens

<400> SEQUENCE: 80

His Ser Asp Ala Val Phe Thr Asp Gln Tyr Thr Arg Leu Arg Lys Gln
1               5                   10                  15

Val Ala Ala Lys Lys Tyr Leu Gln Ser Ile Lys Asn Lys
            20                  25

<210> SEQ ID NO 81
<211> LENGTH: 31
<212> TYPE: PRT
<213> ORGANISM: Homo sapiens

<400> SEQUENCE: 81

His Thr Glu Ala Val Phe Thr Asp Gln Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 82
<211> LENGTH: 31
<212> TYPE: PRT
<213> ORGANISM: Homo sapiens

<400> SEQUENCE: 82

His Ser Asp Ala Val Phe Thr Asp Gln Tyr Thr Arg Leu Arg Lys Gln
1               5                   10                  15

Leu Ala Val Lys Lys Tyr Leu Gln Asp Ile Lys Asn Gly Gly Thr
            20                  25                  30

<210> SEQ ID NO 83
<211> LENGTH: 30
<212> TYPE: PRT
<213> ORGANISM: Homo sapiens

<400> SEQUENCE: 83

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Arg
            20                  25                  30

<210> SEQ ID NO 84
<211> LENGTH: 31
<212> TYPE: PRT
<213> ORGANISM: Homo sapiens

<400> SEQUENCE: 84

His Ser Asp Ala Val Phe Thr Asp Gln Tyr Thr Arg Leu Arg Lys Gln
1               5                   10                  15

Leu Ala Ala Lys Lys Tyr Leu Gln Thr Ile Lys Asn Lys Arg Tyr
            20                  25                  30

<210> SEQ ID NO 85
<211> LENGTH: 31
<212> TYPE: PRT
<213> ORGANISM: Homo sapiens

<400> SEQUENCE: 85

His Ser Asp Ala Val Phe Thr Asp Gln Tyr Thr Arg Leu Arg Lys Gln
1               5                   10                  15

Met Ala Ala Lys Lys Tyr Leu Gln Thr Ile Lys Asn Lys Arg Tyr
            20                  25                  30

<210> SEQ ID NO 86
<211> LENGTH: 31
<212> TYPE: PRT
<213> ORGANISM: Homo sapiens

<400> SEQUENCE: 86

His Ser Asp Ala Val Phe Thr Asp Gln Tyr Thr Arg Leu Arg Lys Gln
1               5                   10                  15

Met Ala Ala His Lys Tyr Leu Gln Ser Ile Lys Asn Lys Arg Tyr
            20                  25                  30

<210> SEQ ID NO 87
<211> LENGTH: 31
<212> TYPE: PRT
<213> ORGANISM: Homo sapiens

<400> SEQUENCE: 87

His Ser Asp Ala Val Phe Thr Asp Gln Tyr Thr Arg Leu Arg Lys Gln
1               5                   10                  15

Met Ala Ala Lys His Tyr Leu Gln Ser Ile Lys Asn Lys Arg Tyr
            20                  25                  30

<210> SEQ ID NO 88
<211> LENGTH: 30
<212> TYPE: PRT
<213> ORGANISM: Homo sapiens

<400> SEQUENCE: 88

His Ser Asp Ala Val Phe Thr Asp Gln Tyr Thr Arg Leu Arg Lys Gln
1               5                   10                  15

Met Ala Gly Lys Lys Tyr Leu Gln Ser Ile Lys Asn Lys Arg
            20                  25                  30

<210> SEQ ID NO 89
<211> LENGTH: 30
<212> TYPE: PRT
<213> ORGANISM: Homo sapiens

<400> SEQUENCE: 89

His Ser Asp Ala Val Phe Thr Asp Gln Tyr Thr Arg Leu Arg Lys Gln
1               5                   10                  15

Met Ala Lys Lys Lys Tyr Leu Gln Ser Ile Lys Asn Lys Arg
            20                  25                  30

<210> SEQ ID NO 90
<211> LENGTH: 30
<212> TYPE: PRT
<213> ORGANISM: Homo sapiens

<400> SEQUENCE: 90

His Ser Asp Ala Val Phe Thr Asp Gln Tyr Thr Arg Leu Arg Lys Gln
1               5                   10                  15

Met Ala Arg Lys Lys Tyr Leu Gln Ser Ile Lys Asn Lys Arg
            20                  25                  30

```
<210> SEQ ID NO 91
<211> LENGTH: 30
<212> TYPE: PRT
<213> ORGANISM: Homo sapiens

<400> SEQUENCE: 91

His Ser Asp Ala Val Phe Thr Asp Gln Tyr Thr Arg Leu Arg Lys Gln
1               5                   10                  15

Met Ala Ser Lys Lys Tyr Leu Gln Ser Ile Lys Asn Lys Arg
            20                  25                  30

<210> SEQ ID NO 92
<211> LENGTH: 30
<212> TYPE: PRT
<213> ORGANISM: Homo sapiens

<400> SEQUENCE: 92

His Ser Asp Ala Val Phe Thr Asp Gln Tyr Thr Arg Leu Arg Lys Gln
1               5                   10                  15

Met Ala Ala Lys Lys Tyr Leu Gln Ser Ile Pro Asn Lys Arg
            20                  25                  30

<210> SEQ ID NO 93
<211> LENGTH: 30
<212> TYPE: PRT
<213> ORGANISM: Homo sapiens

<400> SEQUENCE: 93

His Ser Asp Ala Val Phe Thr Asp Gln Tyr Thr Arg Leu Arg Lys Gln
1               5                   10                  15

Met Ala Ala Lys Lys Tyr Leu Gln Ser Ile Gln Asn Lys Arg
            20                  25                  30

<210> SEQ ID NO 94
<211> LENGTH: 30
<212> TYPE: PRT
<213> ORGANISM: Homo sapiens

<400> SEQUENCE: 94

His Ser Asp Ala Val Phe Thr Asp Gln Tyr Thr Arg Leu Arg Lys Gln
1               5                   10                  15

Met Ala Ala Lys Lys Tyr Leu Gln Ser Ile Arg Asn Lys Arg
            20                  25                  30

<210> SEQ ID NO 95
<211> LENGTH: 30
<212> TYPE: PRT
<213> ORGANISM: Homo sapiens

<400> SEQUENCE: 95

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Arg Arg
            20                  25                  30

<210> SEQ ID NO 96
<211> LENGTH: 30
<212> TYPE: PRT
<213> ORGANISM: Homo sapiens

<400> SEQUENCE: 96

His Ser Asp Ala Val Phe Thr Asp Gln Tyr Thr Arg Leu Arg Lys Gln
1               5                   10                  15
```

Met Ala Ala Lys Lys Tyr Leu Gln Ser Ile Lys Asn Lys Ala
        20                  25                  30

<210> SEQ ID NO 97
<211> LENGTH: 30
<212> TYPE: PRT
<213> ORGANISM: Homo sapiens

<400> SEQUENCE: 97

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Phe
        20                  25                  30

<210> SEQ ID NO 98
<211> LENGTH: 30
<212> TYPE: PRT
<213> ORGANISM: Homo sapiens

<400> SEQUENCE: 98

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys His
        20                  25                  30

<210> SEQ ID NO 99
<211> LENGTH: 30
<212> TYPE: PRT
<213> ORGANISM: Homo sapiens

<400> SEQUENCE: 99

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Ile
        20                  25                  30

<210> SEQ ID NO 100
<211> LENGTH: 30
<212> TYPE: PRT
<213> ORGANISM: Homo sapiens

<400> SEQUENCE: 100

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Lys
        20                  25                  30

<210> SEQ ID NO 101
<211> LENGTH: 30
<212> TYPE: PRT
<213> ORGANISM: Homo sapiens

<400> SEQUENCE: 101

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Leu
        20                  25                  30

<210> SEQ ID NO 102
<211> LENGTH: 30
<212> TYPE: PRT
<213> ORGANISM: Homo sapiens

<400> SEQUENCE: 102

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Met
            20                  25                  30

<210> SEQ ID NO 103
<211> LENGTH: 30
<212> TYPE: PRT
<213> ORGANISM: Homo sapiens

<400> SEQUENCE: 103

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Pro
            20                  25                  30

<210> SEQ ID NO 104
<211> LENGTH: 30
<212> TYPE: PRT
<213> ORGANISM: Homo sapiens

<400> SEQUENCE: 104

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Gln
            20                  25                  30

<210> SEQ ID NO 105
<211> LENGTH: 30
<212> TYPE: PRT
<213> ORGANISM: Homo sapiens

<400> SEQUENCE: 105

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Ser
            20                  25                  30

<210> SEQ ID NO 106
<211> LENGTH: 30
<212> TYPE: PRT
<213> ORGANISM: Homo sapiens

<400> SEQUENCE: 106

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Thr
            20                  25                  30

<210> SEQ ID NO 107
<211> LENGTH: 30
<212> TYPE: PRT
<213> ORGANISM: Homo sapiens

<400> SEQUENCE: 107

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Val
            20                  25                  30

<210> SEQ ID NO 108
<211> LENGTH: 30
<212> TYPE: PRT
<213> ORGANISM: Homo sapiens

<400> SEQUENCE: 108

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Trp
            20                  25                  30

<210> SEQ ID NO 109
<211> LENGTH: 30
<212> TYPE: PRT
<213> ORGANISM: Homo sapiens

<400> SEQUENCE: 109

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Asn Lys Tyr
            20                  25                  30

<210> SEQ ID NO 110
<211> LENGTH: 30
<212> TYPE: PRT
<213> ORGANISM: Homo sapiens

<400> SEQUENCE: 110

His Ser Asp Ala Val Phe Thr Asp Gln Tyr Thr Arg Leu Arg Lys Gln
1               5                   10                  15

Met Ala Gly Lys Lys Tyr Leu Gln Ser Ile Lys Asn Arg Ile
            20                  25                  30

<210> SEQ ID NO 111
<211> LENGTH: 30
<212> TYPE: PRT
<213> ORGANISM: Homo sapiens

<400> SEQUENCE: 111

His Ser Asp Ala Val Phe Thr Asp Gln Tyr Thr Arg Leu Arg Lys Gln
1               5                   10                  15

Met Ala Lys Lys Lys Tyr Leu Gln Ser Ile Lys Asn Arg Ile
            20                  25                  30

<210> SEQ ID NO 112
<211> LENGTH: 30
<212> TYPE: PRT
<213> ORGANISM: Homo sapiens

<400> SEQUENCE: 112

His Ser Asp Ala Val Phe Thr Asp Gln Tyr Thr Arg Leu Arg Lys Gln
1               5                   10                  15

Met Ala Ser Lys Lys Tyr Leu Gln Ser Ile Lys Asn Arg Ile
            20                  25                  30

<210> SEQ ID NO 113
<211> LENGTH: 30
<212> TYPE: PRT
<213> ORGANISM: Homo sapiens

<400> SEQUENCE: 113

His Ser Asp Ala Val Phe Thr Asp Gln Tyr Thr Arg Leu Arg Lys Gln
1               5                   10                  15

```
Met Ala Ala Lys Lys Tyr Leu Gln Ser Ile Pro Asn Arg Ile
            20                  25                  30

<210> SEQ ID NO 114
<211> LENGTH: 30
<212> TYPE: PRT
<213> ORGANISM: Homo sapiens

<400> SEQUENCE: 114

His Ser Asp Ala Val Phe Thr Asp Gln Tyr Thr Arg Leu Arg Lys Gln
1               5                   10                  15

Met Ala Ser Lys Lys Tyr Leu Gln Ser Ile Arg Asn Arg Ile
            20                  25                  30

<210> SEQ ID NO 115
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 115

His Ser Asp Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Arg Tyr Cys
            20                  25                  30

<210> SEQ ID NO 116
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Histidine at position 1 is acetylated; and
      cysteine at position 32 is PEGylated.

<400> SEQUENCE: 116

His Thr Asp Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Arg Tyr Cys
            20                  25                  30

<210> SEQ ID NO 117
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 117

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Arg Tyr Cys
            20                  25                  30

<210> SEQ ID NO 118
<211> LENGTH: 30
<212> TYPE: PRT
<213> ORGANISM: Homo sapiens
```

```
<220> FEATURE:
<221> NAME/KEY: MISC_FEATURE
<222> LOCATION: (1)..(30)
<223> OTHER INFORMATION: Cysteine at position 30 is PEGylated.

<400> SEQUENCE: 118

His Ser Asp Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Cys
            20                  25                  30

<210> SEQ ID NO 119
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 119

His Thr Glu Ala Val Phe Thr Asp Gln Tyr Thr Arg Leu Arg Lys Gln
1               5                   10                  15

Val Ala Ala Lys Lys Tyr Leu Gln Ser Ile Lys Gln Lys Arg Tyr Cys
            20                  25                  30

<210> SEQ ID NO 120
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 120

His Ser Asp Ala Val Phe Thr Asp Gln Tyr Thr Arg Leu Arg Lys Gln
1               5                   10                  15

Leu Ala Val Lys Lys Tyr Leu Gln Asp Ile Lys Gln Gly Gly Thr Cys
            20                  25                  30

<210> SEQ ID NO 121
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 121

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Arg Cys
            20                  25                  30

<210> SEQ ID NO 122
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.
```

```
<400> SEQUENCE: 122

His Ser Asp Ala Val Phe Thr Asp Gln Tyr Thr Arg Leu Arg Lys Gln
1               5                   10                  15

Leu Ala Ala Lys Lys Tyr Leu Gln Thr Ile Lys Gln Lys Arg Tyr Cys
            20                  25                  30

<210> SEQ ID NO 123
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 123

His Ser Asp Ala Val Phe Thr Asp Gln Tyr Thr Arg Leu Arg Lys Gln
1               5                   10                  15

Met Ala Ala Lys Lys Tyr Leu Gln Thr Ile Lys Gln Lys Arg Tyr Cys
            20                  25                  30

<210> SEQ ID NO 124
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 124

His Ser Asp Ala Val Phe Thr Asp Gln Tyr Thr Arg Leu Arg Lys Gln
1               5                   10                  15

Met Ala Ala His Lys Tyr Leu Gln Ser Ile Lys Gln Lys Arg Tyr Cys
            20                  25                  30

<210> SEQ ID NO 125
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Cysteine at position 32 is PEGylated.

<400> SEQUENCE: 125

His Ser Asp Ala Val Phe Thr Asp Gln Tyr Thr Arg Leu Arg Lys Gln
1               5                   10                  15

Met Ala Ala Lys His Tyr Leu Gln Ser Ile Lys Gln Lys Arg Tyr Cys
            20                  25                  30

<210> SEQ ID NO 126
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 126

His Ser Asp Ala Val Phe Thr Asp Gln Tyr Thr Arg Leu Arg Lys Gln
1               5                   10                  15

Met Ala Gly Lys Lys Tyr Leu Gln Ser Ile Lys Gln Lys Arg Cys
            20                  25                  30
```

```
<210> SEQ ID NO 127
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 127

His Ser Asp Ala Val Phe Thr Asp Gln Tyr Thr Arg Leu Arg Lys Gln
1               5                   10                  15

Met Ala Lys Lys Lys Tyr Leu Gln Ser Ile Lys Gln Lys Arg Cys
            20                  25                  30

<210> SEQ ID NO 128
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 128

His Ser Asp Ala Val Phe Thr Asp Gln Tyr Thr Arg Leu Arg Lys Gln
1               5                   10                  15

Met Ala Arg Lys Lys Tyr Leu Gln Ser Ile Lys Gln Lys Arg Cys
            20                  25                  30

<210> SEQ ID NO 129
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 129

His Ser Asp Ala Val Phe Thr Asp Gln Tyr Thr Arg Leu Arg Lys Gln
1               5                   10                  15

Met Ala Ser Lys Lys Tyr Leu Gln Ser Ile Lys Gln Lys Arg Cys
            20                  25                  30

<210> SEQ ID NO 130
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 130

His Ser Asp Ala Val Phe Thr Asp Gln Tyr Thr Arg Leu Arg Lys Gln
1               5                   10                  15

Met Ala Ala Lys Lys Tyr Leu Gln Ser Ile Pro Gln Lys Arg Cys
            20                  25                  30

<210> SEQ ID NO 131
<211> LENGTH: 31
<212> TYPE: PRT
<213> ORGANISM: Homo sapiens
```

```
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 131

His Ser Asp Ala Val Phe Thr Asp Gln Tyr Thr Arg Leu Arg Lys Gln
1               5                   10                  15

Met Ala Ala Lys Lys Tyr Leu Gln Ser Ile Gln Gln Lys Arg Cys
            20                  25                  30

<210> SEQ ID NO 132
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 132

His Ser Asp Ala Val Phe Thr Asp Gln Tyr Thr Arg Leu Arg Lys Gln
1               5                   10                  15

Met Ala Ala Lys Lys Tyr Leu Gln Ser Ile Arg Gln Lys Arg Cys
            20                  25                  30

<210> SEQ ID NO 133
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 133

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Arg Arg Cys
            20                  25                  30

<210> SEQ ID NO 134
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 134

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Ala Cys
            20                  25                  30

<210> SEQ ID NO 135
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.
```

```
<400> SEQUENCE: 135

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Phe Cys
            20                  25                  30

<210> SEQ ID NO 136
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 136

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys His Cys
            20                  25                  30

<210> SEQ ID NO 137
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 137

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Ile Cys
            20                  25                  30

<210> SEQ ID NO 138
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 138

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Lys Cys
            20                  25                  30

<210> SEQ ID NO 139
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 139

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Leu Cys
            20                  25                  30
```

```
<210> SEQ ID NO 140
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 140

His Ser Asp Ala Val Phe Thr Asp Gln Tyr Thr Arg Leu Arg Lys Gln
1               5                   10                  15
Met Ala Ala Lys Lys Tyr Leu Gln Ser Ile Lys Gln Lys Met Cys
            20                  25                  30

<210> SEQ ID NO 141
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 141

His Ser Asp Ala Val Phe Thr Asp Gln Tyr Thr Arg Leu Arg Lys Gln
1               5                   10                  15
Met Ala Ala Lys Lys Tyr Leu Gln Ser Ile Lys Gln Lys Pro Cys
            20                  25                  30

<210> SEQ ID NO 142
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 142

His Ser Asp Ala Val Phe Thr Asp Gln Tyr Thr Arg Leu Arg Lys Gln
1               5                   10                  15
Met Ala Ala Lys Lys Tyr Leu Gln Ser Ile Lys Gln Lys Gln Cys
            20                  25                  30

<210> SEQ ID NO 143
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 143

His Ser Asp Ala Val Phe Thr Asp Gln Tyr Thr Arg Leu Arg Lys Gln
1               5                   10                  15
Met Ala Ala Lys Lys Tyr Leu Gln Ser Ile Lys Gln Lys Ser Cys
            20                  25                  30

<210> SEQ ID NO 144
<211> LENGTH: 31
<212> TYPE: PRT
<213> ORGANISM: Homo sapiens
```

```
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 144

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Thr Cys
            20                  25                  30

<210> SEQ ID NO 145
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 145

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Val Cys
            20                  25                  30

<210> SEQ ID NO 146
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 146

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Trp Cys
            20                  25                  30

<210> SEQ ID NO 147
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 147

His Ser Asp Ala Val Phe Thr Asp Gln Tyr Thr Arg Leu Arg Lys Gln
1               5                   10                  15

Met Ala Ala Lys Lys Tyr Leu Gln Ser Ile Lys Gln Lys Tyr Cys
            20                  25                  30

<210> SEQ ID NO 148
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.
```

```
<400> SEQUENCE: 148

His Ser Asp Ala Val Phe Thr Asp Gln Tyr Thr Arg Leu Arg Lys Gln
1               5                   10                  15

Met Ala Gly Lys Lys Tyr Leu Gln Ser Ile Lys Gln Arg Ile Cys
            20                  25                  30

<210> SEQ ID NO 149
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 149

His Ser Asp Ala Val Phe Thr Asp Gln Tyr Thr Arg Leu Arg Lys Gln
1               5                   10                  15

Met Ala Lys Lys Lys Tyr Leu Gln Ser Ile Lys Gln Arg Ile Cys
            20                  25                  30

<210> SEQ ID NO 150
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 150

His Ser Asp Ala Val Phe Thr Asp Gln Tyr Thr Arg Leu Arg Lys Gln
1               5                   10                  15

Met Ala Ser Lys Lys Tyr Leu Gln Ser Ile Lys Gln Arg Ile Cys
            20                  25                  30

<210> SEQ ID NO 151
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 151

His Ser Asp Ala Val Phe Thr Asp Gln Tyr Thr Arg Leu Arg Lys Gln
1               5                   10                  15

Met Ala Ala Lys Lys Tyr Leu Gln Ser Ile Pro Gln Arg Ile Cys
            20                  25                  30

<210> SEQ ID NO 152
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Cysteine at position 31 is PEGylated.

<400> SEQUENCE: 152

His Ser Asp Ala Val Phe Thr Asp Gln Tyr Thr Arg Leu Arg Lys Gln
1               5                   10                  15

Met Ala Ser Lys Lys Tyr Leu Gln Ser Ile Arg Gln Arg Ile Cys
            20                  25                  30
```

<210> SEQ ID NO 153
<211> LENGTH: 123
<212> TYPE: DNA
<213> ORGANISM: Homo sapiens

<400> SEQUENCE: 153
ggatccatcg aaggtcgtca ctccgacgct gttttcaccg accagtacac gcgtctgcgt     60
aaacaggttg ctgcaaagaa atacctgcag tccatcaagc agaagcgtta ctaatgactc    120
gag                                                                  123

<210> SEQ ID NO 154
<211> LENGTH: 93
<212> TYPE: DNA
<213> ORGANISM: Homo sapiens

<400> SEQUENCE: 154
cactccgacg ctgttttcac cgaccagtac acgcgtctgc gtaaacaggt tgctgcaaag     60
aaatacctgc agtccatcaa gcagaagcgt tac                                  93

<210> SEQ ID NO 155
<211> LENGTH: 93
<212> TYPE: DNA
<213> ORGANISM: Homo sapiens

<400> SEQUENCE: 155
cactccgacg ctgttttcac cgaccagtac acgcgtctgc gtaaacagat ggctgcaaag     60
aaatacctgc agtccatcaa gcagaagcgt tac                                  93

<210> SEQ ID NO 156
<211> LENGTH: 87
<212> TYPE: DNA
<213> ORGANISM: Homo sapiens

<400> SEQUENCE: 156
cactccgacg ctgttttcac cgaccagtac acgcgtctgc gtaaacaggt tgctgcaaag     60
aaatacctgc agtccatcaa gcagaag                                         87

<210> SEQ ID NO 157
<211> LENGTH: 93
<212> TYPE: DNA
<213> ORGANISM: Homo sapiens

<400> SEQUENCE: 157
cacaccgaag ctgttttcac cgaccagtac acgcgtctgc gtaaacaggt tgctgcaaag     60
aaatacctgc agtccatcaa gcagaagcgt tac                                  93

<210> SEQ ID NO 158
<211> LENGTH: 93
<212> TYPE: DNA
<213> ORGANISM: Homo sapiens

<400> SEQUENCE: 158
cactccgacg ctgttttcac cgaccagtac acgcgtctgc gtaaacagct ggctgttaag     60
aaatacctgc aggacatcaa gcagggcggt acc                                  93

<210> SEQ ID NO 159
<211> LENGTH: 90
<212> TYPE: DNA
<213> ORGANISM: Homo sapiens

```
<400> SEQUENCE: 159
cactccgacg ctgttttcac cgaccagtac acgcgtctgc gtaaacagat ggctgcaaag      60
aaatacctgc agtccatcaa gcagaagcgt                                      90

<210> SEQ ID NO 160
<211> LENGTH: 93
<212> TYPE: DNA
<213> ORGANISM: Homo sapiens

<400> SEQUENCE: 160
cactccgacg ctgttttcac cgaccagtac acgcgtctgc gtaaacagct ggctgcaaag      60
aaatacctgc agaccatcaa gcagaagcgt tac                                  93

<210> SEQ ID NO 161
<211> LENGTH: 93
<212> TYPE: DNA
<213> ORGANISM: Homo sapiens

<400> SEQUENCE: 161
cactccgacg ctgttttcac cgaccagtac acgcgtctgc gtaaacagat ggctgcaaag      60
aaatacctgc agaccatcaa gcagaagcgt tac                                  93

<210> SEQ ID NO 162
<211> LENGTH: 93
<212> TYPE: DNA
<213> ORGANISM: Homo sapiens

<400> SEQUENCE: 162
cactccgacg ctgttttcac cgaccagtac acgcgtctgc gtaaacagat ggctgcacac      60
aaatacctgc agtccatcaa gcagaagcgt tac                                  93

<210> SEQ ID NO 163
<211> LENGTH: 93
<212> TYPE: DNA
<213> ORGANISM: Homo sapiens

<400> SEQUENCE: 163
cactccgacg ctgttttcac cgaccagtac acgcgtctgc gtaaacagat ggctgcaaag      60
cactacctgc agtccatcaa gcagaagcgt tac                                  93

<210> SEQ ID NO 164
<211> LENGTH: 90
<212> TYPE: DNA
<213> ORGANISM: Homo sapiens

<400> SEQUENCE: 164
cactccgacg ctgttttcac cgaccagtac acgcgtctgc gtaaacagat ggctggcaag      60
aaatacctgc agtccatcaa gcagaagcgt                                      90

<210> SEQ ID NO 165
<211> LENGTH: 90
<212> TYPE: DNA
<213> ORGANISM: Homo sapiens

<400> SEQUENCE: 165
cactccgacg ctgttttcac cgaccagtac acgcgtctgc gtaaacagat ggctaaaaag      60
aaatacctgc agtccatcaa gcagaagcgt                                      90
```

<210> SEQ ID NO 166
<211> LENGTH: 90
<212> TYPE: DNA
<213> ORGANISM: Homo sapiens

<400> SEQUENCE: 166
cactccgacg ctgttttcac cgaccagtac acgcgtctgc gtaaacagat ggctcgtaag    60
aaatacctgc agtccatcaa gcagaagcgt                                    90

<210> SEQ ID NO 167
<211> LENGTH: 90
<212> TYPE: DNA
<213> ORGANISM: Homo sapiens

<400> SEQUENCE: 167
cactccgacg ctgttttcac cgaccagtac acgcgtctgc gtaaacagat ggcttccaag    60
aaatacctgc agtccatcaa gcagaagcgt                                    90

<210> SEQ ID NO 168
<211> LENGTH: 90
<212> TYPE: DNA
<213> ORGANISM: Homo sapiens

<400> SEQUENCE: 168
cactccgacg ctgttttcac cgaccagtac acgcgtctgc gtaaacagat ggctgcaaag    60
aaatacctgc agtccatccc ccagaagcgt                                    90

<210> SEQ ID NO 169
<211> LENGTH: 90
<212> TYPE: DNA
<213> ORGANISM: Homo sapiens

<400> SEQUENCE: 169
cactccgacg ctgttttcac cgaccagtac acgcgtctgc gtaaacagat ggctgcaaag    60
aaatacctgc agtccatcca gcagaagcgt                                    90

<210> SEQ ID NO 170
<211> LENGTH: 90
<212> TYPE: DNA
<213> ORGANISM: Homo sapiens

<400> SEQUENCE: 170
cactccgacg ctgttttcac cgaccagtac acgcgtctgc gtaaacagat ggctgcaaag    60
aaatacctgc agtccatccg tcagaagcgt                                    90

<210> SEQ ID NO 171
<211> LENGTH: 90
<212> TYPE: DNA
<213> ORGANISM: Homo sapiens

<400> SEQUENCE: 171
cactccgacg ctgttttcac cgaccagtac acgcgtctgc gtaaacagat ggctgcaaag    60
aaatacctgc agtccatcaa gcagcgtcgt                                    90

<210> SEQ ID NO 172
<211> LENGTH: 90
<212> TYPE: DNA
<213> ORGANISM: Homo sapiens

<400> SEQUENCE: 172
cactccgacg ctgttttcac cgaccagtac acgcgtctgc gtaaacagat ggctgcaaag    60
aaatacctgc agtccatcaa gcagaaggca                                     90

<210> SEQ ID NO 173
<211> LENGTH: 90
<212> TYPE: DNA
<213> ORGANISM: Homo sapiens

<400> SEQUENCE: 173
cactccgacg ctgttttcac cgaccagtac acgcgtctgc gtaaacagat ggctgcaaag    60
aaatacctgc agtccatcaa gcagaagttc                                     90

<210> SEQ ID NO 174
<211> LENGTH: 90
<212> TYPE: DNA
<213> ORGANISM: Homo sapiens

<400> SEQUENCE: 174
cactccgacg ctgttttcac cgaccagtac acgcgtctgc gtaaacagat ggctgcaaag    60
aaatacctgc agtccatcaa gcagaagcac                                     90

<210> SEQ ID NO 175
<211> LENGTH: 90
<212> TYPE: DNA
<213> ORGANISM: Homo sapiens

<400> SEQUENCE: 175
cactccgacg ctgttttcac cgaccagtac acgcgtctgc gtaaacagat ggctgcaaag    60
aaatacctgc agtccatcaa gcagaagatc                                     90

<210> SEQ ID NO 176
<211> LENGTH: 90
<212> TYPE: DNA
<213> ORGANISM: Homo sapiens

<400> SEQUENCE: 176
cactccgacg ctgttttcac cgaccagtac acgcgtctgc gtaaacagat ggctgcaaag    60
aaatacctgc agtccatcaa gcagaagaag                                     90

<210> SEQ ID NO 177
<211> LENGTH: 90
<212> TYPE: DNA
<213> ORGANISM: Homo sapiens

<400> SEQUENCE: 177
cactccgacg ctgttttcac cgaccagtac acgcgtctgc gtaaacagat ggctgcaaag    60
aaatacctgc agtccatcaa gcagaagctg                                     90

<210> SEQ ID NO 178
<211> LENGTH: 90
<212> TYPE: DNA
<213> ORGANISM: Homo sapiens

<400> SEQUENCE: 178
cactccgacg ctgttttcac cgaccagtac acgcgtctgc gtaaacagat ggctgcaaag    60
aaatacctgc agtccatcaa gcagaagatg                                     90

<210> SEQ ID NO 179
<211> LENGTH: 90
<212> TYPE: DNA
<213> ORGANISM: Homo sapiens

<400> SEQUENCE: 179
cactccgacg ctgttttcac cgaccagtac acgcgtctgc gtaaacagat ggctgcaaag      60
aaatacctgc agtccatcaa gcagaagccc                                      90

<210> SEQ ID NO 180
<211> LENGTH: 90
<212> TYPE: DNA
<213> ORGANISM: Homo sapiens

<400> SEQUENCE: 180
cactccgacg ctgttttcac cgaccagtac acgcgtctgc gtaaacagat ggctgcaaag      60
aaatacctgc agtccatcaa gcagaagcag                                      90

<210> SEQ ID NO 181
<211> LENGTH: 90
<212> TYPE: DNA
<213> ORGANISM: Homo sapiens

<400> SEQUENCE: 181
cactccgacg ctgttttcac cgaccagtac acgcgtctgc gtaaacagat ggctgcaaag      60
aaatacctgc agtccatcaa gcagaagtcc                                      90

<210> SEQ ID NO 182
<211> LENGTH: 90
<212> TYPE: DNA
<213> ORGANISM: Homo sapiens

<400> SEQUENCE: 182
cactccgacg ctgttttcac cgaccagtac acgcgtctgc gtaaacagat ggctgcaaag      60
aaatacctgc agtccatcaa gcagaagacc                                      90

<210> SEQ ID NO 183
<211> LENGTH: 90
<212> TYPE: DNA
<213> ORGANISM: Homo sapiens

<400> SEQUENCE: 183
cactccgacg ctgttttcac cgaccagtac acgcgtctgc gtaaacagat ggctgcaaag      60
aaatacctgc agtccatcaa gcagaaggtt                                      90

<210> SEQ ID NO 184
<211> LENGTH: 90
<212> TYPE: DNA
<213> ORGANISM: Homo sapiens

<400> SEQUENCE: 184
cactccgacg ctgttttcac cgaccagtac acgcgtctgc gtaaacagat ggctgcaaag      60
aaatacctgc agtccatcaa gcagaagtgg                                      90

<210> SEQ ID NO 185
<211> LENGTH: 90
<212> TYPE: DNA
<213> ORGANISM: Homo sapiens

<400> SEQUENCE: 185
cactccgacg ctgttttcac cgaccagtac acgcgtctgc gtaaacagat ggctgcaaag    60
aaatacctgc agtccatcaa gcagaagtac    90

<210> SEQ ID NO 186
<211> LENGTH: 90
<212> TYPE: DNA
<213> ORGANISM: Homo sapiens

<400> SEQUENCE: 186
cactccgacg ctgttttcac cgaccagtac acgcgtctgc gtaaacagat ggctggtaag    60
aaatacctgc agtccatcaa gcagcgtatc    90

<210> SEQ ID NO 187
<211> LENGTH: 90
<212> TYPE: DNA
<213> ORGANISM: Homo sapiens

<400> SEQUENCE: 187
cactccgacg ctgttttcac cgaccagtac acgcgtctgc gtaaacagat ggctaaaaag    60
aaatacctgc agtccatcaa gcagcgtatc    90

<210> SEQ ID NO 188
<211> LENGTH: 90
<212> TYPE: DNA
<213> ORGANISM: Homo sapiens

<400> SEQUENCE: 188
cactccgacg ctgttttcac cgaccagtac acgcgtctgc gtaaacagat ggcttccaag    60
aaatacctgc agtccatcaa gcagcgtatc    90

<210> SEQ ID NO 189
<211> LENGTH: 90
<212> TYPE: DNA
<213> ORGANISM: Homo sapiens

<400> SEQUENCE: 189
cactccgacg ctgttttcac cgaccagtac acgcgtctgc gtaaacagat ggctgcaaag    60
aaatacctgc agtccatccc ccagcgtatc    90

<210> SEQ ID NO 190
<211> LENGTH: 90
<212> TYPE: DNA
<213> ORGANISM: Homo sapiens

<400> SEQUENCE: 190
cactccgacg ctgttttcac cgaccagtac acgcgtctgc gtaaacagat ggcttccaag    60
aaatacctgc agtccatccg tcagcgtatc    90

<210> SEQ ID NO 191
<211> LENGTH: 93
<212> TYPE: DNA
<213> ORGANISM: Homo sapiens

<400> SEQUENCE: 191
cactccgacg ctgttttcac cgacaactac acgcgtctgc gtaaacaggt tgctgcaaag    60
aaatacctgc agtccatcaa gcagaagcgt tac    93

<210> SEQ ID NO 192
<211> LENGTH: 93
<212> TYPE: DNA
<213> ORGANISM: Homo sapiens

<400> SEQUENCE: 192
cactccgacg ctgttttcac cgacaactac acgcgtctgc gtaaacagat ggctgcaaag    60
aaatacctgc agtccatcaa gcagaagcgt tac                                 93

<210> SEQ ID NO 193
<211> LENGTH: 87
<212> TYPE: DNA
<213> ORGANISM: Homo sapiens

<400> SEQUENCE: 193
cactccgacg ctgttttcac cgacaactac acgcgtctgc gtaaacaggt tgctgcaaag    60
aaatacctgc agtccatcaa gcagaag                                        87

<210> SEQ ID NO 194
<211> LENGTH: 93
<212> TYPE: DNA
<213> ORGANISM: Homo sapiens

<400> SEQUENCE: 194
cacaccgaag ctgttttcac cgacaactac acgcgtctgc gtaaacaggt tgctgcaaag    60
aaatacctgc agtccatcaa gcagaagcgt tac                                 93

<210> SEQ ID NO 195
<211> LENGTH: 93
<212> TYPE: DNA
<213> ORGANISM: Homo sapiens

<400> SEQUENCE: 195
cactccgacg ctgttttcac cgacaactac acgcgtctgc gtaaacagct ggctgttaag    60
aaatacctgc aggacatcaa gcagggcggt acc                                 93

<210> SEQ ID NO 196
<211> LENGTH: 90
<212> TYPE: DNA
<213> ORGANISM: Homo sapiens

<400> SEQUENCE: 196
cactccgacg ctgttttcac cgacaactac acgcgtctgc gtaaacagat ggctgcaaag    60
aaatacctgc agtccatcaa gcagaagcgt                                     90

<210> SEQ ID NO 197
<211> LENGTH: 93
<212> TYPE: DNA
<213> ORGANISM: Homo sapiens

<400> SEQUENCE: 197
cactccgacg ctgttttcac cgacaactac acgcgtctgc gtaaacagct ggctgcaaag    60
aaatacctgc agaccatcaa gcagaagcgt tac                                 93

<210> SEQ ID NO 198
<211> LENGTH: 93
<212> TYPE: DNA
<213> ORGANISM: Homo sapiens

<400> SEQUENCE: 198
cactccgacg ctgttttcac cgacaactac acgcgtctgc gtaaacagat ggctgcaaag    60
aaatacctgc agaccatcaa gcagaagcgt tac                                 93

<210> SEQ ID NO 199
<211> LENGTH: 93
<212> TYPE: DNA
<213> ORGANISM: Homo sapiens

<400> SEQUENCE: 199
cactccgacg ctgttttcac cgacaactac acgcgtctgc gtaaacagat ggctgcacac    60
aaatacctgc agtccatcaa gcagaagcgt tac                                 93

<210> SEQ ID NO 200
<211> LENGTH: 93
<212> TYPE: DNA
<213> ORGANISM: Homo sapiens

<400> SEQUENCE: 200
cactccgacg ctgttttcac cgacaactac acgcgtctgc gtaaacagat ggctgcaaag    60
cactacctgc agtccatcaa gcagaagcgt tac                                 93

<210> SEQ ID NO 201
<211> LENGTH: 93
<212> TYPE: DNA
<213> ORGANISM: Homo sapiens

<400> SEQUENCE: 201
cactccgacg ctgttttcac cgacaactac acgcgtctgc gtaaacagat ggctgcaaag    60
cactacctgc agtccatcaa gcagaagcgt tac                                 93

<210> SEQ ID NO 202
<211> LENGTH: 90
<212> TYPE: DNA
<213> ORGANISM: Homo sapiens

<400> SEQUENCE: 202
cactccgacg ctgttttcac cgacaactac acgcgtctgc gtaaacagat ggctaaaaag    60
aaatacctgc agtccatcaa gcagaagcgt                                     90

<210> SEQ ID NO 203
<211> LENGTH: 90
<212> TYPE: DNA
<213> ORGANISM: Homo sapiens

<400> SEQUENCE: 203
cactccgacg ctgttttcac cgacaactac acgcgtctgc gtaaacagat ggctcgtaag    60
aaatacctgc agtccatcaa gcagaagcgt                                     90

<210> SEQ ID NO 204
<211> LENGTH: 90
<212> TYPE: DNA
<213> ORGANISM: Homo sapiens

<400> SEQUENCE: 204
cactccgacg ctgttttcac cgacaactac acgcgtctgc gtaaacagat ggcttccaag    60
aaatacctgc agtccatcaa gcagaagcgt                                     90

```
<210> SEQ ID NO 205
<211> LENGTH: 90
<212> TYPE: DNA
<213> ORGANISM: Homo sapiens

<400> SEQUENCE: 205
cactccgacg ctgttttcac cgacaactac acgcgtctgc gtaaacagat ggctgcaaag      60
aaatacctgc agtccatccc ccagaagcgt                                      90

<210> SEQ ID NO 206
<211> LENGTH: 90
<212> TYPE: DNA
<213> ORGANISM: Homo sapiens

<400> SEQUENCE: 206
cactccgacg ctgttttcac cgacaactac acgcgtctgc gtaaacagat ggctgcaaag      60
aaatacctgc agtccatcca gcagaagcgt                                      90

<210> SEQ ID NO 207
<211> LENGTH: 90
<212> TYPE: DNA
<213> ORGANISM: Homo sapiens

<400> SEQUENCE: 207
cactccgacg ctgttttcac cgacaactac acgcgtctgc gtaaacagat ggctgcaaag      60
aaatacctgc agtccatccg tcagaagcgt                                      90

<210> SEQ ID NO 208
<211> LENGTH: 90
<212> TYPE: DNA
<213> ORGANISM: Homo sapiens

<400> SEQUENCE: 208
cactccgacg ctgttttcac cgacaactac acgcgtctgc gtaaacagat ggctgcaaag      60
aaatacctgc agtccatcaa gcagcgtcgt                                      90

<210> SEQ ID NO 209
<211> LENGTH: 90
<212> TYPE: DNA
<213> ORGANISM: Homo sapiens

<400> SEQUENCE: 209
cactccgacg ctgttttcac cgacaactac acgcgtctgc gtaaacagat ggctgcaaag      60
aaatacctgc agtccatcaa gcagaaggca                                      90

<210> SEQ ID NO 210
<211> LENGTH: 90
<212> TYPE: DNA
<213> ORGANISM: Homo sapiens

<400> SEQUENCE: 210
cactccgacg ctgttttcac cgacaactac acgcgtctgc gtaaacagat ggctgcaaag      60
aaatacctgc agtccatcaa gcagaagttc                                      90

<210> SEQ ID NO 211
<211> LENGTH: 90
<212> TYPE: DNA
<213> ORGANISM: Homo sapiens
```

<400> SEQUENCE: 211
cactccgacg ctgttttcac cgacaactac acgcgtctgc gtaaacagat ggctgcaaag    60
aaatacctgc agtccatcaa gcagaagcac    90

<210> SEQ ID NO 212
<211> LENGTH: 90
<212> TYPE: DNA
<213> ORGANISM: Homo sapiens

<400> SEQUENCE: 212
cactccgacg ctgttttcac cgacaactac acgcgtctgc gtaaacagat ggctgcaaag    60
aaatacctgc agtccatcaa gcagaagatc    90

<210> SEQ ID NO 213
<211> LENGTH: 90
<212> TYPE: DNA
<213> ORGANISM: Homo sapiens

<400> SEQUENCE: 213
cactccgacg ctgttttcac cgacaactac acgcgtctgc gtaaacagat ggctgcaaag    60
aaatacctgc agtccatcaa gcagaagaag    90

<210> SEQ ID NO 214
<211> LENGTH: 90
<212> TYPE: DNA
<213> ORGANISM: Homo sapiens

<400> SEQUENCE: 214
cactccgacg ctgttttcac cgacaactac acgcgtctgc gtaaacagat ggctgcaaag    60
aaatacctgc agtccatcaa gcagaagctg    90

<210> SEQ ID NO 215
<211> LENGTH: 90
<212> TYPE: DNA
<213> ORGANISM: Homo sapiens

<400> SEQUENCE: 215
cactccgacg ctgttttcac cgacaactac acgcgtctgc gtaaacagat ggctgcaaag    60
aaatacctgc agtccatcaa gcagaagatg    90

<210> SEQ ID NO 216
<211> LENGTH: 90
<212> TYPE: DNA
<213> ORGANISM: Homo sapiens

<400> SEQUENCE: 216
cactccgacg ctgttttcac cgacaactac acgcgtctgc gtaaacagat ggctgcaaag    60
aaatacctgc agtccatcaa gcagaagccc    90

<210> SEQ ID NO 217
<211> LENGTH: 90
<212> TYPE: DNA
<213> ORGANISM: Homo sapiens

<400> SEQUENCE: 217
cactccgacg ctgttttcac cgacaactac acgcgtctgc gtaaacagat ggctgcaaag    60
aaatacctgc agtccatcaa gcagaagcag    90

<210> SEQ ID NO 218
<211> LENGTH: 90
<212> TYPE: DNA
<213> ORGANISM: Homo sapiens

<400> SEQUENCE: 218
cactccgacg ctgttttcac cgacaactac acgcgtctgc gtaaacagat ggctgcaaag        60
aaatacctgc agtccatcaa gcagaagtcc                                         90

<210> SEQ ID NO 219
<211> LENGTH: 90
<212> TYPE: DNA
<213> ORGANISM: Homo sapiens

<400> SEQUENCE: 219
cactccgacg ctgttttcac cgacaactac acgcgtctgc gtaaacagat ggctgcaaag        60
aaatacctgc agtccatcaa gcagaagacc                                         90

<210> SEQ ID NO 220
<211> LENGTH: 90
<212> TYPE: DNA
<213> ORGANISM: Homo sapiens

<400> SEQUENCE: 220
cactccgacg ctgttttcac cgacaactac acgcgtctgc gtaaacagat ggctgcaaag        60
aaatacctgc agtccatcaa gcagaaggtt                                         90

<210> SEQ ID NO 221
<211> LENGTH: 90
<212> TYPE: DNA
<213> ORGANISM: Homo sapiens

<400> SEQUENCE: 221
cactccgacg ctgttttcac cgacaactac acgcgtctgc gtaaacagat ggctgcaaag        60
aaatacctgc agtccatcaa gcagaagtgg                                         90

<210> SEQ ID NO 222
<211> LENGTH: 90
<212> TYPE: DNA
<213> ORGANISM: Homo sapiens

<400> SEQUENCE: 222
cactccgacg ctgttttcac cgacaactac acgcgtctgc gtaaacagat ggctgcaaag        60
aaatacctgc agtccatcaa gcagaagtac                                         90

<210> SEQ ID NO 223
<211> LENGTH: 90
<212> TYPE: DNA
<213> ORGANISM: Homo sapiens

<400> SEQUENCE: 223
cactccgacg ctgttttcac cgacaactac acgcgtctgc gtaaacagat ggctggtaag        60
aaatacctgc agtccatcaa gcagcgtatc                                         90

<210> SEQ ID NO 224
<211> LENGTH: 90
<212> TYPE: DNA
<213> ORGANISM: Homo sapiens

```
<400> SEQUENCE: 224
cactccgacg ctgttttcac cgacaactac acgcgtctgc gtaaacagat ggctaaaaag      60
aaatacctgc agtccatcaa gcagcgtatc                                      90

<210> SEQ ID NO 225
<211> LENGTH: 90
<212> TYPE: DNA
<213> ORGANISM: Homo sapiens

<400> SEQUENCE: 225
cactccgacg ctgttttcac cgacaactac acgcgtctgc gtaaacagat ggcttccaag      60
aaatacctgc agtccatcaa gcagcgtatc                                      90

<210> SEQ ID NO 226
<211> LENGTH: 90
<212> TYPE: DNA
<213> ORGANISM: Homo sapiens

<400> SEQUENCE: 226
cactccgacg ctgttttcac cgacaactac acgcgtctgc gtaaacagat ggctgcaaag      60
aaatacctgc agtccatccc ccagcgtatc                                      90

<210> SEQ ID NO 227
<211> LENGTH: 90
<212> TYPE: DNA
<213> ORGANISM: Homo sapiens

<400> SEQUENCE: 227
cactccgacg ctgttttcac cgacaactac acgcgtctgc gtaaacagat ggcttccaag      60
aaatacctgc agtccatccg tcagcgtatc                                      90

<210> SEQ ID NO 228
<211> LENGTH: 93
<212> TYPE: DNA
<213> ORGANISM: Homo sapiens

<400> SEQUENCE: 228
cactccgacg ctgttttcac cgaccagtac acgcgtctgc gtaaacaggt tgctgcaaag      60
aaatacctgc agtccatcaa gaacaagcgt tac                                  93

<210> SEQ ID NO 229
<211> LENGTH: 93
<212> TYPE: DNA
<213> ORGANISM: Homo sapiens

<400> SEQUENCE: 229
cactccgacg ctgttttcac cgaccagtac acgcgtctgc gtaaacagat ggctgcaaag      60
aaatacctgc agtccatcaa gaacaagcgt tac                                  93

<210> SEQ ID NO 230
<211> LENGTH: 87
<212> TYPE: DNA
<213> ORGANISM: Homo sapiens

<400> SEQUENCE: 230
cactccgacg ctgttttcac cgaccagtac acgcgtctgc gtaaacaggt tgctgcaaag      60
aaatacctgc agtccatcaa gaacaag                                         87
```

<210> SEQ ID NO 231
<211> LENGTH: 93
<212> TYPE: DNA
<213> ORGANISM: Homo sapiens

<400> SEQUENCE: 231
cacaccgaag ctgttttcac cgaccagtac acgcgtctgc gtaaacaggt tgctgcaaag    60
aaatacctgc agtccatcaa gaacaagcgt tac                                 93

<210> SEQ ID NO 232
<211> LENGTH: 93
<212> TYPE: DNA
<213> ORGANISM: Homo sapiens

<400> SEQUENCE: 232
cactccgacg ctgttttcac cgaccagtac acgcgtctgc gtaaacagct ggctgttaag    60
aaatacctgc aggacatcaa gaacggcggt acc                                 93

<210> SEQ ID NO 233
<211> LENGTH: 90
<212> TYPE: DNA
<213> ORGANISM: Homo sapiens

<400> SEQUENCE: 233
cactccgacg ctgttttcac cgaccagtac acgcgtctgc gtaaacagat ggctgcaaag    60
aaatacctgc agtccatcaa gaacaagcgt                                     90

<210> SEQ ID NO 234
<211> LENGTH: 93
<212> TYPE: DNA
<213> ORGANISM: Homo sapiens

<400> SEQUENCE: 234
cactccgacg ctgttttcac cgaccagtac acgcgtctgc gtaaacagct ggctgcaaag    60
aaatacctgc agaccatcaa gaacaagcgt tac                                 93

<210> SEQ ID NO 235
<211> LENGTH: 93
<212> TYPE: DNA
<213> ORGANISM: Homo sapiens

<400> SEQUENCE: 235
cactccgacg ctgttttcac cgaccagtac acgcgtctgc gtaaacagat ggctgcaaag    60
aaatacctgc agaccatcaa gaacaagcgt tac                                 93

<210> SEQ ID NO 236
<211> LENGTH: 93
<212> TYPE: DNA
<213> ORGANISM: Homo sapiens

<400> SEQUENCE: 236
cactccgacg ctgttttcac cgaccagtac acgcgtctgc gtaaacagat ggctgcacac    60
aaatacctgc agtccatcaa gaacaagcgt tac                                 93

<210> SEQ ID NO 237
<211> LENGTH: 93
<212> TYPE: DNA
<213> ORGANISM: Homo sapiens

<400> SEQUENCE: 237
cactccgacg ctgttttcac cgaccagtac acgcgtctgc gtaaacagat ggctgcaaag    60
cactacctgc agtccatcaa gaacaagcgt tac    93

<210> SEQ ID NO 238
<211> LENGTH: 90
<212> TYPE: DNA
<213> ORGANISM: Homo sapiens

<400> SEQUENCE: 238
cactccgacg ctgttttcac cgaccagtac acgcgtctgc gtaaacagat ggctggcaag    60
aaatacctgc agtccatcaa gaacaagcgt    90

<210> SEQ ID NO 239
<211> LENGTH: 90
<212> TYPE: DNA
<213> ORGANISM: Homo sapiens

<400> SEQUENCE: 239
cactccgacg ctgttttcac cgaccagtac acgcgtctgc gtaaacagat ggctaaaaag    60
aaatacctgc agtccatcaa gaacaagcgt    90

<210> SEQ ID NO 240
<211> LENGTH: 90
<212> TYPE: DNA
<213> ORGANISM: Homo sapiens

<400> SEQUENCE: 240
cactccgacg ctgttttcac cgaccagtac acgcgtctgc gtaaacagat ggctcgtaag    60
aaatacctgc agtccatcaa gaacaagcgt    90

<210> SEQ ID NO 241
<211> LENGTH: 90
<212> TYPE: DNA
<213> ORGANISM: Homo sapiens

<400> SEQUENCE: 241
cactccgacg ctgttttcac cgaccagtac acgcgtctgc gtaaacagat ggcttccaag    60
aaatacctgc agtccatcaa gaacaagcgt    90

<210> SEQ ID NO 242
<211> LENGTH: 90
<212> TYPE: DNA
<213> ORGANISM: Homo sapiens

<400> SEQUENCE: 242
cactccgacg ctgttttcac cgaccagtac acgcgtctgc gtaaacagat ggctgcaaag    60
aaatacctgc agtccatccc caacaagcgt    90

<210> SEQ ID NO 243
<211> LENGTH: 90
<212> TYPE: DNA
<213> ORGANISM: Homo sapiens

<400> SEQUENCE: 243
cactccgacg ctgttttcac cgaccagtac acgcgtctgc gtaaacagat ggctgcaaag    60
aaatacctgc agtccatcca gaacaagcgt    90

<210> SEQ ID NO 244
<211> LENGTH: 90
<212> TYPE: DNA
<213> ORGANISM: Homo sapiens

<400> SEQUENCE: 244
cactccgacg ctgttttcac cgaccagtac acgcgtctgc gtaaacagat ggctgcaaag    60
aaatacctgc agtccatccg taacaagcgt                                     90

<210> SEQ ID NO 245
<211> LENGTH: 90
<212> TYPE: DNA
<213> ORGANISM: Homo sapiens

<400> SEQUENCE: 245
cactccgacg ctgttttcac cgaccagtac acgcgtctgc gtaaacagat ggctgcaaag    60
aaatacctgc agtccatcaa gaaccgtcgt                                     90

<210> SEQ ID NO 246
<211> LENGTH: 90
<212> TYPE: DNA
<213> ORGANISM: Homo sapiens

<400> SEQUENCE: 246
cactccgacg ctgttttcac cgaccagtac acgcgtctgc gtaaacagat ggctgcaaag    60
aaatacctgc agtccatcaa gaacaaggca                                     90

<210> SEQ ID NO 247
<211> LENGTH: 90
<212> TYPE: DNA
<213> ORGANISM: Homo sapiens

<400> SEQUENCE: 247
cactccgacg ctgttttcac cgaccagtac acgcgtctgc gtaaacagat ggctgcaaag    60
aaatacctgc agtccatcaa gaacaagttc                                     90

<210> SEQ ID NO 248
<211> LENGTH: 90
<212> TYPE: DNA
<213> ORGANISM: Homo sapiens

<400> SEQUENCE: 248
cactccgacg ctgttttcac cgaccagtac acgcgtctgc gtaaacagat ggctgcaaag    60
aaatacctgc agtccatcaa gaacaagcac                                     90

<210> SEQ ID NO 249
<211> LENGTH: 90
<212> TYPE: DNA
<213> ORGANISM: Homo sapiens

<400> SEQUENCE: 249
cactccgacg ctgttttcac cgaccagtac acgcgtctgc gtaaacagat ggctgcaaag    60
aaatacctgc agtccatcaa gaacaagatc                                     90

<210> SEQ ID NO 250
<211> LENGTH: 90
<212> TYPE: DNA
<213> ORGANISM: Homo sapiens

```
<400> SEQUENCE: 250
cactccgacg ctgttttcac cgaccagtac acgcgtctgc gtaaacagat ggctgcaaag    60
aaatacctgc agtccatcaa gaacaagaag                                     90

<210> SEQ ID NO 251
<211> LENGTH: 90
<212> TYPE: DNA
<213> ORGANISM: Homo sapiens

<400> SEQUENCE: 251
cactccgacg ctgttttcac cgaccagtac acgcgtctgc gtaaacagat ggctgcaaag    60
aaatacctgc agtccatcaa gaacaagctg                                     90

<210> SEQ ID NO 252
<211> LENGTH: 90
<212> TYPE: DNA
<213> ORGANISM: Homo sapiens

<400> SEQUENCE: 252
cactccgacg ctgttttcac cgaccagtac acgcgtctgc gtaaacagat ggctgcaaag    60
aaatacctgc agtccatcaa gaacaagatg                                     90

<210> SEQ ID NO 253
<211> LENGTH: 90
<212> TYPE: DNA
<213> ORGANISM: Homo sapiens

<400> SEQUENCE: 253
cactccgacg ctgttttcac cgaccagtac acgcgtctgc gtaaacagat ggctgcaaag    60
aaatacctgc agtccatcaa gaacaagccc                                     90

<210> SEQ ID NO 254
<211> LENGTH: 90
<212> TYPE: DNA
<213> ORGANISM: Homo sapiens

<400> SEQUENCE: 254
cactccgacg ctgttttcac cgaccagtac acgcgtctgc gtaaacagat ggctgcaaag    60
aaatacctgc agtccatcaa gaacaagcag                                     90

<210> SEQ ID NO 255
<211> LENGTH: 90
<212> TYPE: DNA
<213> ORGANISM: Homo sapiens

<400> SEQUENCE: 255
cactccgacg ctgttttcac cgaccagtac acgcgtctgc gtaaacagat ggctgcaaag    60
aaatacctgc agtccatcaa gaacaagtcc                                     90

<210> SEQ ID NO 256
<211> LENGTH: 90
<212> TYPE: DNA
<213> ORGANISM: Homo sapiens

<400> SEQUENCE: 256
cactccgacg ctgttttcac cgaccagtac acgcgtctgc gtaaacagat ggctgcaaag    60
aaatacctgc agtccatcaa gaacaagacc                                     90
```

<210> SEQ ID NO 257
<211> LENGTH: 90
<212> TYPE: DNA
<213> ORGANISM: Homo sapiens

<400> SEQUENCE: 257
cactccgacg ctgttttcac cgaccagtac acgcgtctgc gtaaacagat ggctgcaaag      60
aaatacctgc agtccatcaa gaacaaggtt                                      90

<210> SEQ ID NO 258
<211> LENGTH: 90
<212> TYPE: DNA
<213> ORGANISM: Homo sapiens

<400> SEQUENCE: 258
cactccgacg ctgttttcac cgaccagtac acgcgtctgc gtaaacagat ggctgcaaag      60
aaatacctgc agtccatcaa gaacaagtgg                                      90

<210> SEQ ID NO 259
<211> LENGTH: 90
<212> TYPE: DNA
<213> ORGANISM: Homo sapiens

<400> SEQUENCE: 259
cactccgacg ctgttttcac cgaccagtac acgcgtctgc gtaaacagat ggctgcaaag      60
aaatacctgc agtccatcaa gaacaagtac                                      90

<210> SEQ ID NO 260
<211> LENGTH: 90
<212> TYPE: DNA
<213> ORGANISM: Homo sapiens

<400> SEQUENCE: 260
cactccgacg ctgttttcac cgaccagtac acgcgtctgc gtaaacagat ggctggtaag      60
aaatacctgc agtccatcaa gaaccgtatc                                      90

<210> SEQ ID NO 261
<211> LENGTH: 90
<212> TYPE: DNA
<213> ORGANISM: Homo sapiens

<400> SEQUENCE: 261
cactccgacg ctgttttcac cgaccagtac acgcgtctgc gtaaacagat ggctaaaaag      60
aaatacctgc agtccatcaa gaaccgtatc                                      90

<210> SEQ ID NO 262
<211> LENGTH: 90
<212> TYPE: DNA
<213> ORGANISM: Homo sapiens

<400> SEQUENCE: 262
cactccgacg ctgttttcac cgaccagtac acgcgtctgc gtaaacagat ggcttccaag      60
aaatacctgc agtccatcaa gaaccgtatc                                      90

<210> SEQ ID NO 263
<211> LENGTH: 90
<212> TYPE: DNA
<213> ORGANISM: Homo sapiens

```
<400> SEQUENCE: 263
cactccgacg ctgttttcac cgaccagtac acgcgtctgc gtaaacagat ggctgcaaag      60
aaatacctgc agtccatccc caaccgtatc                                      90

<210> SEQ ID NO 264
<211> LENGTH: 90
<212> TYPE: DNA
<213> ORGANISM: Homo sapiens

<400> SEQUENCE: 264
cactccgacg ctgttttcac cgaccagtac acgcgtctgc gtaaacagat ggcttccaag      60
aaatacctgc agtccatccg taaccgtatc                                      90
```